US010981946B2

(12) United States Patent
Moriarty et al.

(10) Patent No.: US 10,981,946 B2
(45) Date of Patent: *Apr. 20, 2021

(54) METHODS FOR THE PURIFICATION OF DEOXYCHOLIC ACID

(71) Applicant: ALLERGAN SALES, LLC, Madison, NJ (US)

(72) Inventors: Robert M. Moriarty, Michiana Shores, IN (US); Achampeta Rathan Prasad, Hyderabad (IN); John Gregory Reid, Groton, MA (US); Roy A. Swaringen, Jr., Durham, NC (US)

(73) Assignee: Allergan Sales, LLC, Madison, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/591,539

(22) Filed: Oct. 2, 2019

(65) Prior Publication Data
US 2020/0095274 A1 Mar. 26, 2020

Related U.S. Application Data

(63) Continuation of application No. 15/990,135, filed on May 25, 2018, now Pat. No. 10,472,384, which is a continuation of application No. 15/603,290, filed on May 23, 2017, now Pat. No. 10,005,813, which is a continuation of application No. 14/532,940, filed on Nov. 4, 2014, now Pat. No. 9,683,007, which is a continuation of application No. 13/140,421, filed as application No. PCT/US2010/061150 on Dec. 17, 2010, now abandoned.

(60) Provisional application No. 61/288,132, filed on Dec. 18, 2009, provisional application No. 61/302,007, filed on Feb. 5, 2010, provisional application No. 61/303,816, filed on Feb. 12, 2010, provisional application No. 61/348,686, filed on May 26, 2010.

(30) Foreign Application Priority Data

May 25, 2010 (GB) .................................... 1008726

(51) Int. Cl.
    C07J 9/00       (2006.01)
    A61K 31/575     (2006.01)
    C07J 1/00       (2006.01)
    C07J 5/00       (2006.01)
    C07J 13/00      (2006.01)
    C07J 41/00      (2006.01)

(52) U.S. Cl.
    CPC ............ *C07J 9/005* (2013.01); *A61K 31/575* (2013.01); *C07J 1/0011* (2013.01); *C07J 5/0053* (2013.01); *C07J 9/00* (2013.01); *C07J 13/007* (2013.01); *C07J 41/0061* (2013.01); *Y02P 20/55* (2015.11)

(58) Field of Classification Search
    CPC ... C07J 9/00; C07J 9/005; C07J 1/0011; C07J 5/0053; C07J 13/007; C07J 21/00; C07J 21/008; C07J 41/0061; A61K 31/575; Y02P 20/55
    See application file for complete search history.

(56) References Cited

U.S. PATENT DOCUMENTS

| | | | |
|---|---|---|---|
| 2,321,598 A | 6/1943 | Hoehn et al. | |
| 2,509,248 A | 5/1950 | Hastings Sarett et al. | |
| 2,651,643 A | 9/1953 | Sifferd et al. | |
| 2,891,972 A | 6/1959 | Paterson et al. | |
| 4,158,707 A | 6/1979 | Steffen et al. | |
| 4,277,408 A | 7/1981 | Pavan et al. | |
| 4,664,910 A | 5/1987 | Caserio et al. | |
| 5,085,864 A | 2/1992 | Cannon et al. | |
| 6,348,456 B1 | 2/2002 | Mash et al. | |
| 6,417,179 B1 | 7/2002 | Burkhart et al. | |
| 7,166,299 B2 | 1/2007 | Yoo | |
| 2002/0107291 A1 | 8/2002 | De Tommaso | |
| 2005/0261258 A1 | 11/2005 | Kolodney et al. | |
| 2005/0267080 A1 | 12/2005 | Kolodney et al. | |
| 2006/0222695 A1 | 10/2006 | Zadini et al. | |
| 2008/0318870 A1 | 12/2008 | Moriarty et al. | |
| 2010/0179337 A2 | 7/2010 | Prasad et al. | |
| 2013/0085125 A1 | 4/2013 | Ganley et al. | |
| 2013/0102580 A1 | 4/2013 | Prasad et al. | |
| 2013/0137884 A1 | 5/2013 | Moriarty et al. | |

FOREIGN PATENT DOCUMENTS

| | | |
|---|---|---|
| CA | 2033725 C | 5/2001 |
| CA | 2567298 | 12/2005 |
| CN | 101148468 A | 3/2008 |
| EP | 0 336 521 B1 | 4/1992 |

(Continued)

OTHER PUBLICATIONS

"Ich Harmonised Tripartite Guideline. Impurities in New Drug Substances Q3a (R2)", International Conference on Harmonisation of Technical Requirements for Registration of Pharmaceuticals for Human Use, Oct. 25, 2006, pp. 1-11.
Arsenou et al., "Optimization of the allylic oxidation in the synthesis of 7-keto-5-steroidal substrates*," Steroids 68, (2003), 407-414.
Avissar et al., "Plasma Selenium-dependent Glutathione Peroxidase," J. Biol. Chem., (1989), 264(27):15850-15855.
Bril et al., "Fractionation of spinach chloroplasts with sodium deoxycholate," Biochim. Biophys. Acta, (1969), 172:345-348.

(Continued)

*Primary Examiner* — Barbara P Badio
(74) *Attorney, Agent, or Firm* — Foley & Lardner LLP

(57) ABSTRACT

Synthetic methods for preparing deoxycholic acid and intermediates thereof, high purity synthetic deoxycholic acid, compositions and methods of use are provided. Also, provided are processes for the synthesis of 12-keto or 12-α-hydroxysteroids from Δ-9,11-ene, 11-keto or 11-hydroxy-β-steroids. This invention is also directed to novel compounds prepared during the synthesis. This invention is also directed to the synthesis of deoxycholic acid starting from hydrocortisone.

10 Claims, 3 Drawing Sheets

(56) References Cited

FOREIGN PATENT DOCUMENTS

| | | |
|---|---|---|
| GB | 0 695 504 A | 8/1953 |
| GB | 0 716 670 A | 10/1954 |
| JP | 2004-534042 A2 | 11/2004 |
| TW | 201317258 A1 | 5/2013 |
| TW | I572616 B | 3/2017 |
| WO | WO-99/52932 A1 | 10/1999 |
| WO | WO-00/47215 | 8/2000 |
| WO | WO-02/094849 | 11/2002 |
| WO | WO-2005/112942 A1 | 12/2005 |
| WO | WO-2008/091540 A2 | 7/2008 |
| WO | WO-2008/157635 A2 | 12/2008 |
| WO | WO-2009/149392 A1 | 12/2009 |
| WO | WO-2011/075701 A2 | 6/2011 |
| WO | WO-2012/174229 A2 | 12/2012 |

OTHER PUBLICATIONS

Candeloro De Sanctis et al., "The Hexagonal Phase of the 3:2:1 Canal Complex between Deoxycholic Acid, Ethanol and Water: An Inclusion Compound with Hydrophilic Channels," Acta Crys., (1978), B34:1928-1933.

Chen et al., "Formation of Sodium Dodecyl Sulfate-stable Fibronectin Multimers," J Biol. Chem., (1996), 271 (15):9084-9089.

Cho et al., "α-Lipoic Acid Inhibits Adipocyte Differentiation by Regulating Pro-adipogenic Transcription Factors via Mitogen-activated Protein Kinase Pathways," J. Biol. Chem, (2003), 278(37):34823-34833.

Coiro et al. "The Tetragonal Phase of the 2:1:1 Canal Complex between Deoxycholic Acid, Ethanol and Water," Acta Cryst., (1979), B35:2941-2944.

Complaint for Patent Infringement, *Kythera Biopharmaceuticals, Inc.* v. *Slayback Pharma LLC*, Filed Nov. 9, 2018.

Corey, et al., "Stereospecific Total Synthesis of Gibberellic Acid. A Key Tricyclic Intermediate," J. Am. Chem. Soc., (1978), 100(25):8031-8034.

Crowley et al., "The NAD+ precursors, nicotinic acid and nicotinamide protect cells against apoptosis induced by a multiple stress inducer, deoxycholate," Cell Death and Differentiation, (2000), 7:314-326.

Dakir et al., "Optimization of Allylic Oxidation of (1S,3R,8R)-2,2-Dichloro-3,7, 7, 1 O-tetramethyltricyclo[6,4,0,0]dodec-9-ene". Synthetic Communications, vol. 34(11), pp. 2001-2008, (2004).

Duncan et al., "Lipodissolve for Subcutaneous Fat Reduction and Skin Retraction," Aesthetic Surgery Journal, (2005), 25(5):530-543.

EP Extended Search report dated Sep. 29, 2014 in EP Patent Application No. 12800614.5.

European Communication Pursuant to Article 94(3)EPC dated Jun. 11, 2012 in related European Patent Application No. 05852147.7.

FDA Guidance for Industry, Q6B Specifications: Test Procedures and Acceptance Criteria for Biotechnological/Biological Products, U.S. Department of Health and Human Services Food and Drug Administration, (Aug. 1999).

Fieser et al., "Oxidation of Steroids. III. Selective Oxidations and Acylations in the Bile Acid Series." J. Am. Chem. Soc., (1950), 72(2):5530-5536.

Gething et al., "Purification of fusion protein of Sendai virus: Analysis of the NH2-terminal sequence generated during precursor activation," Proc. Natl. Acad. Sci., (1978), 75(6):2737-2740.

Goto, et al., "Synthesis of Disulfates of Unconjugated and Conjugated Bile Acids," Chem Pharma Bulletin, (1987), 35(11):4562-4567.

Goto, et al., "Synthesis of Monosulfates of Unconjugated and Conjugated Bile Acids," Chem Pharma Bulletin, (1979), 27(6):1402-1411.

Hofmann et al., "Physicochemical properties of bile acids and their relationship to biological properties: an overview of the problem," J. Lipid Res., (1984), 25:1477-1489.

Hofmann, et al., "Bile acid solubility and precipitation in vitro and in vivo: the role of conjugation, pH, and Ca2 ions," J Lipid Res., (1992), 33:617-626.

International Search Report and Written Opinion dated Jan. 31, 2013 in related PCT Patent Application No. PCT/US2012/042440.

International Search Report dated Feb. 11, 2013 in related PCT Application No. PCT/US12/56691.

International Search Report dated May 29, 2012 in related PCT Application No. PCT/US2010/061150.

Kasal. "Hydrogenation of 12-0xo-5β-Chol-9(11)-Enates on Platinum." Collection of Czechoslovak Chemical Communication, vol. 46, (1981), pp. 1839-1849.

Kolodney et al., "Tissue-Selective Effects of Injected Deoxycholate," Dermatolog. Surg., 36, pp. 899-908 (2010).

Lardon, et al., "Uber Bestandteile der Nebennierenrinde and verwandte Stoffe," Helvetica Chimica Acta., (1947), 30:1373-1378.

Lichtenberg et al., "On the solubility of calcium deoxycholate: kinetics of precipitation and the effect of conjugated bile salts and lecithin," Chem. Phys. Lipids, (1988), 46:279-291.

Lodish, et al. "Section 3.5—Purifying, Detecting and Characterizing Proteins," Molecular Cell Biology. 4th edition. New York: W. H. Freeman; 2000 pp. 83-99, (Mar. 1, 2019).

MacLachlan I., "Liposomal Formulations for Nucleic Acid Delivery," In Antisense Drug Technology, Principles, Strategies and Applications, 2nd Edition, Crooke S.T.; Ed.; Taylor & Francis Group, (2007), 237-270 ("MacLachlin 2007") at 253.

Mahler et al.,"Protein Aggregation: Pathways, Induction Factors, and Analysis," J. Pharm. Sci., (2009), 98(9):2909-2934.

Martins et al., "Lipid-based colloidal carriers for peptide and protein delivery—liposomes versus lipid nanoparticles," Int. J Nanomedicine, (2007), 2(4):595-607.

Marwah, P. et al., "An economical and green approach for the oxidation of olefins to enones," Green Chem., 6, pp. 570-577 (Oct. 13, 2004).

Meder, et al., "Coordination Chemistry of 1,3-Bis(2-pyridylimino)- and 1,3-Bis-(2-thiazolylimino)isoindole Copper Complexes: Investigation of Their Catalytic Behavior in Oxidation Reactions," Eur. J. Inorg. Chem., (2004), 2716-2722.

Momose et al., "Calcium-Liquid Ammonia Reduction of 12-Keto Bile Acids: An Alternative route to 12alpha- and 12beta-Hydroxy Acids", The Journal of the College of Engineering Nihon University, 1987, A-28, 171-173.

Murata et al., "Study of the Micelle Formation of Sodium Deoxycholate. Concentration Dependence of Carbon-13 Nuclear Magnetic Resonance Chemical Shift," J. Phys. Chem., (1982), 86:4690-4694.

Murata et al., "Study on the Micelle Formation of Sodium Deoxycholate, In Solution Behavior of Surfactants," Eds., Mittal K.L. et al., Plenum Press, New York, (1982), 611-627.

Narain, et al.,"Lecithin Protects against Plasma Membrane Disruption by Bile Salts," J. Surg. Res., (1998), 78(2):131-136.

Nonappa et al., "Solid-State NMR, X-ray Diffraction, and Thermo analytical Studies Towards the Identification, Isolation, and Structural Characterization of Polymorphs in Natural Bile Acids", Crystal Growth & Design, (2009), 9(11):4710-4719.

Notice of Allowance on U.S. Appl. No. 15/990,135 dated Jul. 3, 2019.

Okuda, et al., "The Organic Composition of Earwax," J. Otolaryngol., (1991), 20(3):212-215.

Smith, S., "A Heated Debate on Hot Snot Fat-Zapper," The New York Post, Dec. 8, 2002, 12.

Stavroudis C., "Sorting Out Surfactants," WAAC Newsletter, (2009), 31(1):18-21.

Stoll et al., "In Vitro Dissolution and In Vivo Absorption of Nitrofurantoin from Deoxycholic Acid Coprecipitates," J Pharm. Sci., (1973), 62(1):65-68.

Su et al., "Regulation of System A Amino Acid Transport in 3T3-L1 Adipocytes by Insulin." J. Biol. Chem., (1998), 273(6):3173-3179.

Tozuka et al., "Supercritical carbon dioxide treatment as a method for polymorph preparation of deoxycholic acid", Int J Pharm., (2003), 263(1-2):45-50.

Tserng, et al., "Bile acid sulfates. III. Synthesis of 7- and 12-monosulfates of bile acids and their conjugates using a sulfur trioxide-triethylamine complex," Steroids, (1979), 33(2):167-182.

U.S. Notice of Allowance dated Oct. 3, 2019 in related U.S. Appl. No. 15/990,135.

(56) References Cited

OTHER PUBLICATIONS

U.S. Notice of Allowance on U.S. Appl. No. 14/532,940 dated Feb. 22, 2017.
U.S. Notice of Allowance on U.S. Appl. No. 15/603,290 dated Feb. 28, 2018.
U.S. Office Action dated May 5, 2014 in related U.S. Appl. No. 13/140,421.
U.S. Office Action on U.S. Appl. No. 14/532,940 dated Apr. 15, 2016.
U.S. Office Action on U.S. Appl. No. 14/532,940 dated Oct. 7, 2016.
Wendel, A., Lecithin: The First 150 Years—Part II: Evolution to a global pharmaceutical industry, Inform, (2000), 11:992-997.
Wright et al., "Formulation Development of AAV2 Vectors: Identification of Excipients That Inhibit Vector Aggregation," Mo. Therapy, (2004), 9(Supplement 1):S163, Abstract 425.
Zhang et al., "A potent small molecule inhibits polyglutamine aggregation in Huntington's disease neurons and suppresses neurodegeneration in vivo," Proc. Natl. Acad. Sci., (2005), 102(3):892-897.
Pharmaceutical Affairs bureau Notification 1216001 (with English translation) dated Oct. 25, 2006.
Reich et al. "Constituents of the adrenal cortex and related substances. LXXV. 9-Androsten-3(beta.)-ol-17-one," Helv Chim Acta., (1947), 30:329-334.
Reich, H., "Uber Bestandteile der Nebennierenrinde und verwandte Stoffe," Helvetica Chimica Acta., (1945), 28:863-872.
Rittes, P. G., "The Use of Phosphatidylcholine for Correction of Localized Fat Deposits," Aesth. Plast. Surg. (2003), 27:315-318.
Rittes, P. G., "The use of Phosphatidylcholine for Correction of Lower Lid Bulging Due to Prominent Fat Pads," Dermatol. Surg., (2001), vol. 27:4, pp. 391-392.
Rotunda et al. "Lipomas treated with subcutaneous deoxycholate injections." J. Am. Acad. Dermatol., (2005) pp. 973-978.
Rotunda et al. "Mesotherapy and Phosphatidylcholine Injections: Historical Clarification and Review" Dermatologic Surgery, (2006) 32: 465-480.
Rotunda et al., "Randomized double-blind clinical trial of subcutaneously injected deoxycholate versus a phosphatidylcholine-deoxycholate combination for the reduction of submental fat", Dermatologic Surgery, (2009), 35(5):792-803.
Rotunda, et al., "Detergent effects of sodium deoxycholate are a major feature of an injectable phosphatidylcholine formulation used for localized fat dissolution," Dermatol. Surg., (2004), 30(7):1001-1008.
Ryden et al., "The effects of pH and bile salts on the binding of MelQx to wheat bran fibre," Mutation Res., (1996), 351:45-52.
Sachs et al., "The Effect of Pyrophosphate on the Amino Acid Incorporating System of Rat Liver Microsomes," J. Biol. Chem., (1958), 233(3):650-656.
Segura, et al., "Synthetic Receptors for Uronic Acid Salts Based on Bicyclic Guanidinium and Deoxycholic Acid Subunits," Tetrahedron, (1997), 53(38):13119-13128.
Shoppee, C.W. (w-English Machine Translation) 98. Androsten-(9)-dione-(3, 17), Remarks on H. Reich and A. Lardon, Androstene (9)-ol- (3β)-one-(17), Helvetica Chimica Acta , (Jul. 8, 1947), vol. 30:766-768.
Sigma Product Information Sheet, RIP A Buffer, Product No. R0278, Sep. 2003.
Sigma Product Information Sheet, Sodium deoxycholate, Product No. D6750, May 2006.
Small, "Size and Structure of Bile Salt Micelles. Influence of Structure, Concentration, Counterion Concentration, pH, and Temperature", In Molecular Association in Biological and Related Systems; Goddard, E.; Advances in Chemistry; American Chemical Society: Washington, DC, 31-52, (1968).

METHODS FOR THE PURIFICATION OF DEOXYCHOLIC ACID

REFERENCE TO RELATED APPLICATIONS

This application is a continuation of U.S. patent application Ser. No. 15/990,135, filed May 25, 2018, which is a continuation of U.S. patent application Ser. No. 15/603,290, filed May 23, 2017, now U.S. Pat. No. 10,005,813, which is a continuation of U.S. patent application Ser. No. 14/532,940, filed Nov. 4, 2014, now U.S. Pat. No. 9,683,007, which is a continuation of U.S. patent application Ser. No. 13/140,421, filed Sep. 24, 2012, which is a U.S. national stage of PCT/US2010/061150, filed Dec. 17, 2010, which claims the benefit of U.S. provisional application Ser. No. 61/288,132, filed on 18 Dec. 2009, U.S. provisional application Ser. No. 61/302,007, filed on 5 Feb. 2010, U.S. provisional application Ser. No. 61/303,816, filed on 12 Feb. 2010, U.K. Application No. 1008726.0 filed on 25 May 2010, and U.S. provisional application Ser. No. 61/348,686, filed on 26 May 2010, all of which are incorporated by reference herein in their entirety.

BACKGROUND OF THE INVENTION

Field of the Invention

This invention is directed to the synthesis of deoxycholic acid and salts thereof as well as to intermediates useful in the synthesis of deoxycholic acid. In one embodiment, this invention provides synthetic methods for preparing deoxycholic acid or a salt thereof starting from hydrocortisone. This invention is also directed to intermediates such as 12-keto or 12-α-hydroxysteroids as well as novel processes for their preparation. This invention still further provides purified deoxycholic acid compositions and methods for purification wherein the deoxycholic acid has a purity of at least 96%.

State of the Art

Rapid removal of body fat is an age-old ideal, and many substances have been claimed to accomplish such results, although few have shown results. "Mesotherapy", or the use of injectables for the removal of fat, is not widely accepted among medical practitioners due to safety and efficacy concerns, although homeopathic and cosmetic claims have been made since the 1950's. Mesotherapy was originally conceived in Europe as a method of utilizing cutaneous injections containing a mixture of compounds for the treatment of local medical and cosmetic conditions. Although mesotherapy was traditionally employed for pain relief, its cosmetic applications, particularly fat and cellulite removal, have recently received attention in the United States. One such reported treatment for localized fat reduction, which was popularized in Brazil and uses injections of phosphatidylcholine, has been erroneously considered synonymous with mesotherapy. Despite its attraction as a purported "fat-dissolving" injection, there is little safety and efficacy data of these cosmetic treatments. See, Rotunda, A. M. and M. Kolodney, Dermatologic Surgery 32, 465-480 (2006) ("Mesotherapy and Phosphatidylcholine Injections: Historical Clarification and Review").

Recently published literature reports that the bile acid, deoxycholic acid, and salts thereof, have fat removing properties when injected into fatty deposits in vivo. See, WO 2005/117900 and WO 2005/112942, as well as US2005/0261258; US2005/0267080; US2006/127468; and US20060154906, all incorporated herein by reference in their entirety). Deoxycholate injected into fat tissue degrades fat cells via a cytolytic mechanism. Because deoxycholate injected into fat is rapidly inactivated by exposure to protein and then rapidly returns to the intestinal contents, its effects are spatially contained. As a result of this attenuation effect that confers clinical safety, fat removal therapies typically require 4-6 sessions. This localized fat removal without the need for surgery is beneficial not only for therapeutic treatment relating to pathological localized fat deposits (e.g., dyslipidemias incident to medical intervention in the treatment of HIV), but also for cosmetic fat removal without the attendant risk inherent in surgery (e.g., liposuction). See, Rotunda et al., Dermatol. Surgery 30: 1001-1008 (2004) ("Detergent effects of sodium deoxycholate are a major feature of an injectable phosphatidylcholine formulation used for localized fat dissolution") and Rotunda et al., J. Am. Acad. Dermatol. (2005: 973-978) ("Lipomas treated with subcutaneous deoxycholate injections"), both incorporated herein by reference in their entirety.

In addition, many important steroids have a 12-α-hydroxy-substituent on the C-ring of the steroid. Such compounds include, by way of example, bile acids such as deoxycholic acid, cholic acid, lithocholic acid, and the like. Heretofore, such compounds were typically recovered from bovine and ovine sources which provided a ready source of bile acids on a cost effective basis. However, with the recent discovery that pathogens such as prions can contaminate such sources, alternative methods for the synthesis of bile acids from plant sources or synthetic starting materials have become increasingly important. For example, deoxycholic acid from animals in New Zealand are a source of bile acids for human use under US regulatory regimes, as long as the animals continue to remain isolated and otherwise free of observable pathogens. Such stringent conditions impose a limitation on the amount of suitable mammalian sourced bile acids and does not preclude the possibility that the bile acid will be free of such pathogens.

There remains a need for suitable quantities of efficacious bile acids such as deoxycholic acid that are known from the outset to be free from moieties of animal origin (or pathogenic moieties capable of acting in an animal, particularly a mammal, and for human use, having a deleterious effect on a human), and other harmful agents such as animal or microbial metabolites, toxins, including bacterial toxins, such as pyrogens, for use as medicaments in humans.

In addition, there is a need to prepare a bile acid composition free of other unintended bile acids. In this regard, it is known that mammalian sourced deoxycholic acid is contaminated with cholic acid. In turn, it is further known that cholic acid is an essential component in the formation of gall stones. Accordingly, there is an ongoing need to provide methods for preparing deoxycholic acid which methods would not result in contamination with other bile acids.

Heretofore, GB2452358 discloses the synthesis of deoxycholic acid starting with 9α-hydroxyandrost-4-en-3,17-dione. In that synthesis, the intermediate 3α-hydroxy-5β-androst-9(11)-en-17-one is disclosed as being derived from 9α-hydroxyandrost-4-en-3,17-dione. While 9α-hydroxyandrost-4-en-3,17-dione is effectively converted to deoxycholic acid as disclosed in that patent, synthesis of deoxycholic acid from hydrocortisone would be of particular value as hydrocortisone is widely available.

Cortisone and hydrocortisone have an 11-keto or 11-β-hydroxy group respectively rather than the 12-α-hydroxy group of deoxycholic acid. Conversion of the 11-keto or 11-3-hydroxy group on the steroidal backbone to the corresponding 12-α-hydroxy or 12-keto group is non-trivial as not only must the conversion be made it must be made stereoselectively. International Patent Application Publication No. WO2008/157635 reports multiple reaction schemes where, in one instance, a 3-β-acetoxy-11-keto steroid is converted to a 3-β-acetoxy-12-α-hydroxysteroid via formation of a Δ-9,11-ene functionality in said steroid following by allylic oxidation at the 12-position with chromium trioxide. The use of chromium trioxide provides modest yields of the Δ-9,11-ene-12-oxo functionalities and side products generated by this reaction encumber purification of the desired product. Moreover, chromium trioxide is highly toxic, corrosive, and carcinogenic. It is the main example of hexavalent chromium, an environmental hazard. Use of chromium trioxide in the oxidation process should be limited.

In view of the above, there is a need to provide a synthetically efficient method for converting 11-β-hydroxy/11-keto steroids to the corresponding a Δ-9,11-ene, 12-α-hydroxy/12-keto steroids using environmentally compatible and less toxic oxidizing agents.

Pharmaceutical grade chemicals require consistently reproducible levels of purity. In some embodiments, purification processes should provide at least 95% purity or at least 99% purity. However, purification to at least 99% is technically challenging. For example, solvents used in the purification process can become entrapped with the product thereby reducing its purity and other contaminants can be carried over by any purification process.

This problem is particularly relevant with deoxycholic acid and salts thereof as this product is disclosed for cosmetic use in removing undesirable fat deposits. See, e.g., U.S. Pat. No. 7,622,130 which is incorporated herein by reference in its entirety. As cosmetic procedures are entirely elective, higher safety standards are typically required by regulatory authorities.

SUMMARY OF THE INVENTION

This invention provides methods and compositions useful in the preparation of bile acids or salts thereof as well as methods for purification of the so prepared bile acids.

In one embodiment, there is provided an oxidation process which either eliminates or limits the amount of chromium (VI) oxidizing agent employed during allylic oxidation at the 12-position of Δ-9,11-ene steroids. The oxidation employs an environmentally compatible co-oxidant mixture which provides compounds 1, 2, and 3:

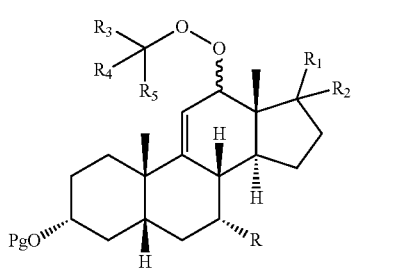

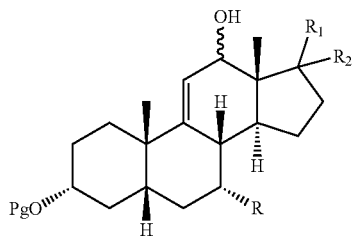

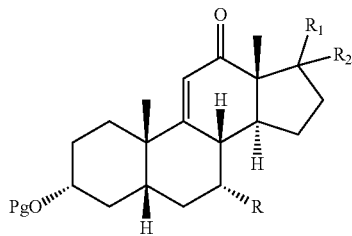

wherein Pg is a hydroxyl protecting group, R is hydrogen, hydroxyl, or —OPg, $R^1$ is the 17-side chain of a bile acid, which bile acid is selected from the group consisting of cholic acid, deoxycholic acid, taurocholic acid, and glycocholic acid, wherein the carboxyl functionality of said side chain is optionally esterified with a $C_1$-$C_6$ alkyl group, and $R^2$ is hydrogen, or $R^1$ and $R^2$ together with the carbon atom attached thereto form a keto group or a keto protecting group; and each of $R^3$, $R^4$ and $R^5$ is independently $C_1$-$C_3$ alkyl.

Optionally, in a further step, the above mixture is treated with a chromium (VI) oxidizing agent to convert the partially oxidized products at the 12-position to the corresponding ketone. In this process, the amount of chromium (VI) oxidizing agent employed is significantly less than that reported in Example 10 of U.S. Ser. No. 12/153,446 which employed chromium trioxide as the sole oxidizing agent.

Accordingly, in one embodiment, there is provided a method for effecting allylic oxidation at the 12-position of Δ-9,11-ene steroidal compound 4:

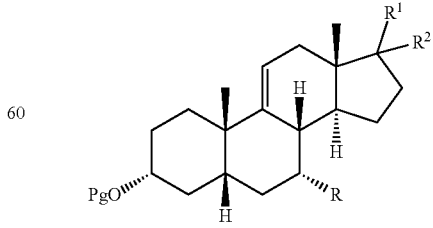

to the corresponding 12-keto compound 3:

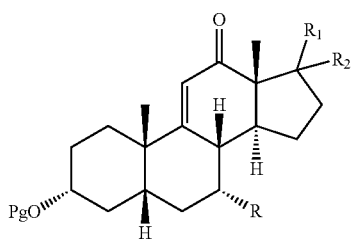

3 which method comprises contacting compound 4 with a co-oxidant mixture comprising alkali hypochlorite and t-alkyl hydrogen peroxide under oxidizing conditions to provide compound 3;

wherein Pg is a hydroxyl protecting group, R is hydrogen, hydroxyl, or —OPg, $R^1$ is the 17-side chain of a bile acid, which bile acid is selected from the group consisting of cholic acid, deoxycholic acid, taurocholic acid, and glycocholic acid, wherein the carboxyl functionality of said side chain is optionally esterified with a $C_1$-$C_6$ alkyl group, and $R^2$ is hydrogen, or $R^1$ and $R^2$ together with the carbon atom attached thereto form a keto group or a keto protecting group.

In another embodiment, oxidation of compound 4 with said co-oxidant mixture provides compounds:

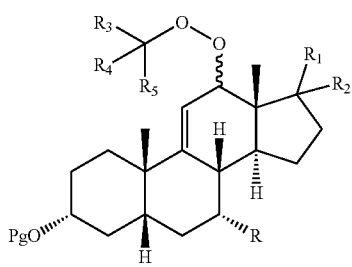

1

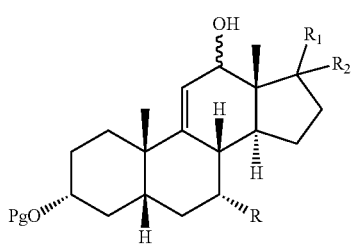

2

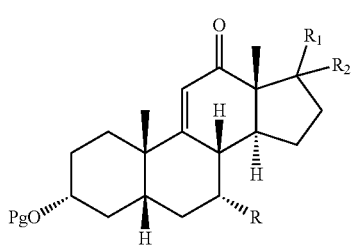

3 wherein Pg is a hydroxyl protecting group, R is hydrogen, hydroxyl, or —OPg, $R^1$ is the 17-side chain of a bile acid, which bile acid is selected from the group consisting of cholic acid, deoxycholic acid, taurocholic acid, and glycocholic acid, wherein the carboxyl functionality of said side chain is optionally esterified with a $C_1$-$C_6$ alkyl group, and $R^2$ is hydrogen, or $R^1$ and $R^2$ together with the carbon atom attached thereto form a keto group or a keto protecting group; and each of $R^3$, $R^4$ and $R^5$ is independently $C_1$-$C_3$ alkyl.

The mixture provided optionally can be treated with a slight excess of a chromium oxidizing agent to provide conversion of compound 2 and optionally compound 1 to compound 3 thereby improving the overall yield of compound 3. Accordingly, in this embodiment, there is provided a method for effecting allylic oxidation at the 12-position of Δ-9,11-ene steroidal compound 4:

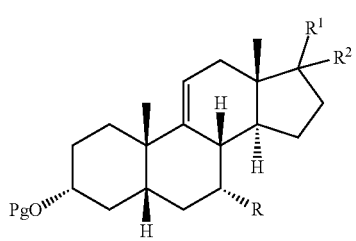

4 to the corresponding 12-keto compound 3:

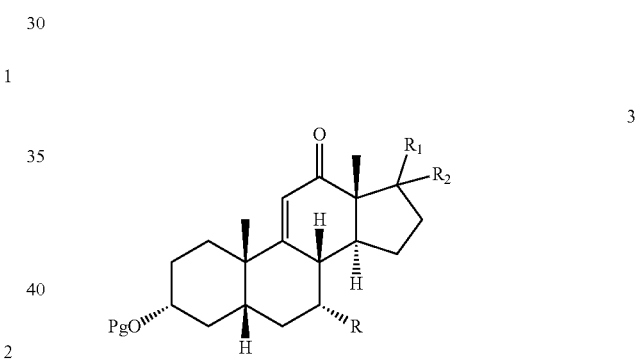

3 which process comprises contacting compound 4 with a co-oxidant mixture comprising alkali hypochlorite and t-alkyl hydrogen peroxide (TBHP) under oxidizing conditions to provide a mixture of compound 1, 2, and 3; and further oxidizing said mixture with an effective amount of a chromium (VI) oxidizing agent to provide compound 3, wherein Pg is a hydroxyl protecting group, R is hydrogen, hydroxyl, or —OPg, $R^1$ is the 17-side chain of a bile acid, which bile acid is selected from the group consisting of cholic acid, deoxycholic acid, taurocholic acid, and glycocholic acid, wherein the carboxyl functionality of said side chain is optionally esterified with a $C_1$-$C_6$ alkyl group, and $R^2$ is hydrogen, or $R^1$ and $R^2$ together with the carbon atom attached thereto form a keto group or a keto protecting group.

In one optional embodiment, the mixture of compounds 1, 2 and 3 are reacted under hydrogenation conditions to hydrogenate the Δ-9,11-ene prior to oxidation with the chromium (VI) oxidizing agent.

When said optional hydrogenation occurs prior to oxidation with the chromium (VI), there are provided novel intermediates of formula 5 and 6:

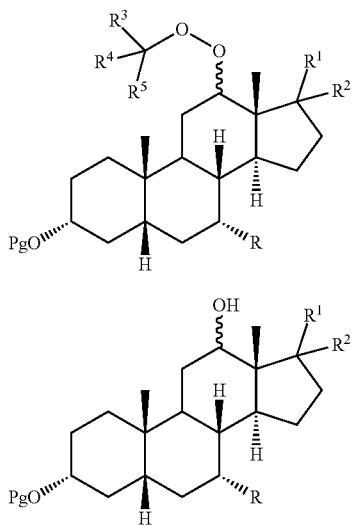

5

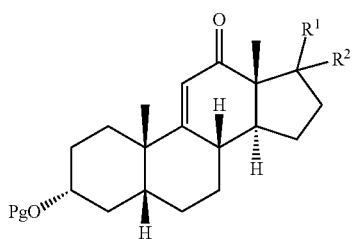

6 wherein Pg, R, R¹, R², R³, R⁴ and R⁵ are as defined above

In a preferred embodiment, hydrogenation occurs after oxidation step(s) is (are) completed.

In another embodiment, this invention provides a process for preparing Δ-9,11-ene-12-keto compound 7:

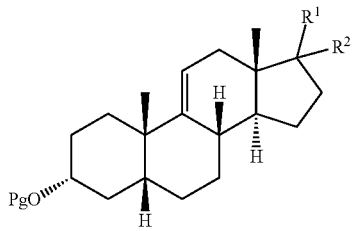

7 from the corresponding Δ-9,11-ene compound 8:

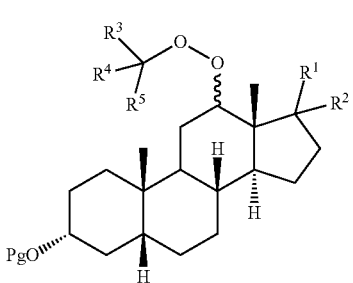

8 where Pg is a hydroxyl protecting group, R¹ is the 17-side chain of a bile acid, which bile acid is selected from the group consisting of cholic acid, deoxycholic acid, taurocholic acid, and glycocholic acid, wherein the carboxyl functionality of said side chain is optionally esterified with a $C_1$-$C_6$ alkyl group, and R² is hydrogen, or R¹ and R² together with the carbon atom attached thereto form a keto group or a keto protecting group;

wherein said process comprises:

effecting allylic oxidation at the 12-position of compound 8 by reaction with an t-alkylhydroperoxide of the formula $(R^3)(R^4)(R^5)C$—O—OH in the presence of a co-oxidant, wherein each of R³, R⁴, and R⁵ is independently $C_1$-$C_3$ alkyl, to first provide a mixture of compounds 9, 10, and 7:

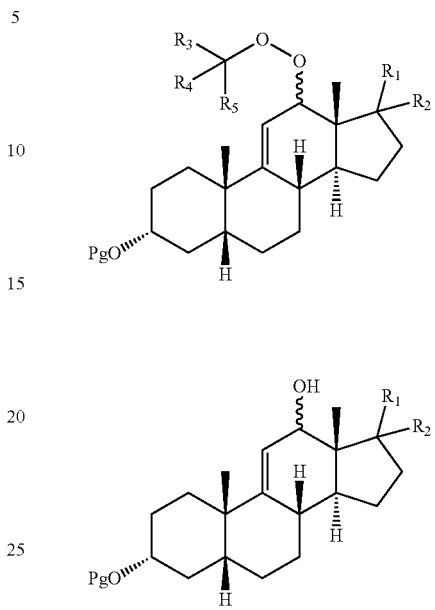

9

10

7 and optionally wherein compound 11b is then further oxidized with a chromium (VI) oxidizing agent to provide the Δ-9,11-ene-12-one compound 7.

In one optional embodiment, the mixture of compounds 9, 10, and 7 are reacted under hydrogenation conditions to hydrogenate the Δ-9,11-ene prior to oxidation with the chromium (VI) oxidizing agent.

When said optional hydrogenation occurs prior to oxidation with the chromium (VI) oxidizing agent, there are provided novel intermediates of formula 11a and 11b:

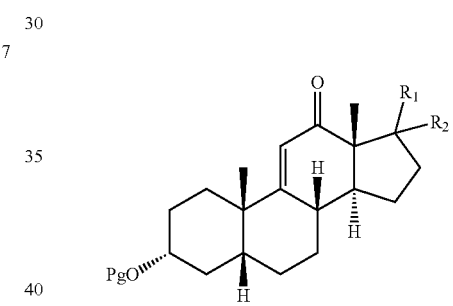

11a

-continued

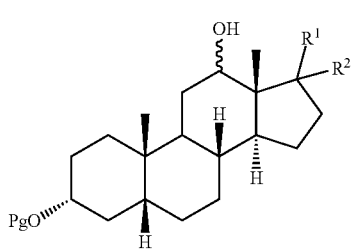

11b wherein Pg, R$^1$, R$^2$, R$^3$, R$^4$ and R$^5$ are as defined above.

In another embodiment, this invention provides a process for converting an 11-β-hydroxysteroid to the corresponding 12-ketosteroid wherein said process comprises:

a) selecting an appropriately protected 11-β-hydroxysteroid;

b) dehydrating the 11-β-hydroxysteroid to provide the Δ-9,11-ene functionality in said steroid;

c) effecting allylic oxidation at the 12-position by reacting the steroid product of b) above with t-alkylhydroperoxide in the presence of a co-oxidant; and d) hydrogenating the Δ-9,11-ene functionality to yield the 9-α-hydro-11-dihydro-12-ketosteroid; and e) optionally reducing the 12-keto functionality of the 9-α-hydro-11-dihydro-12-ketosteroid produced in d) above with an effective amount of a reducing agent to provide the 9-α-hydro-11-dihydro-12-α-hydroxysteroid.

In another embodiment, this invention provides a method for preparing compound 12

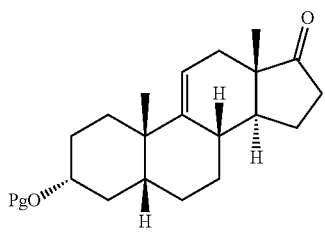

12 comprising contacting compound 13 wherein Pg is a hydroxyl protecting group:

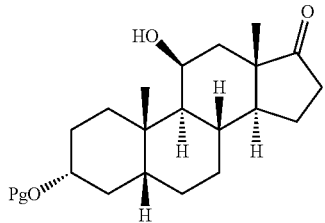

13 under dehydrating conditions to provide compound 12.

In another embodiment, this invention provides a method for preparing a compound of formula 14

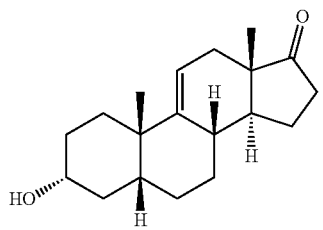

14 a) contacting hydrocortisone:

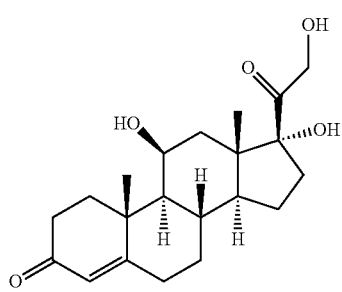

with at least a molar equivalent of hydrogen under hydrogenation conditions to provide 4,5-dihydrohydrocortisone—compound 15:

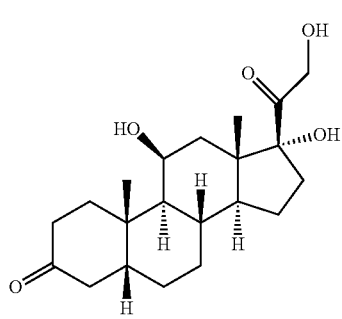

15 b) contacting compound 15 with at least 2 equivalents of a reducing agent under conditions wherein the carbonyl groups are reduced to alcohol groups to provide compound 16:

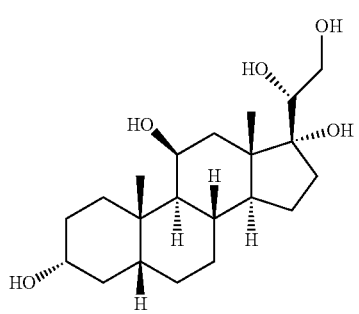

16 c) contacting compound 16 with a vicinal alcohol oxidizing agent under oxidizing conditions to provide compound 17:

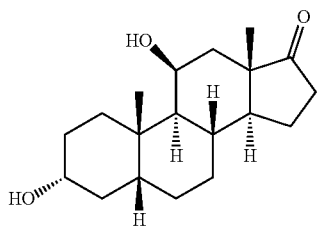

17 d) selectively protecting the 3-hydroxyl group of compound 17 to provide a compound of formula 13:

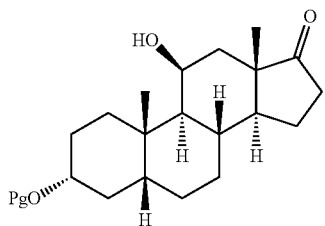

13 where Pg is a hydroxyl protecting group;

e) contacting the compound of formula 13 under dehydrating conditions to provide a compound of formula 12;

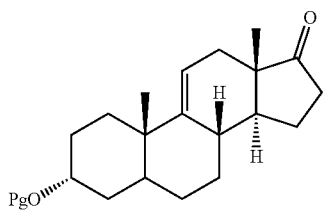

12 f) and removing the hydroxyl protecting group to provide compound 14.

In another embodiment, this invention provides a method of preparing a compound of formula 18:

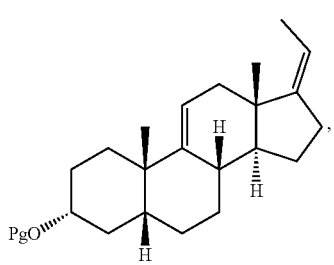

18 said method comprising:
a) contacting hydrocortisone:

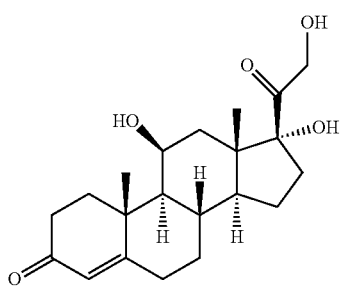

5 with at least a molar equivalent of hydrogen under hydrogenation conditions to provide 4,5-dihydrohydrocortisone—compound 15:

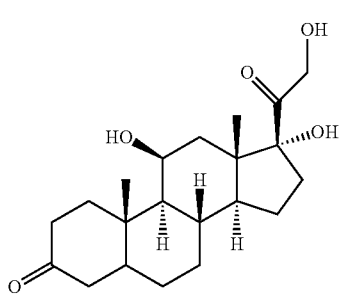

15 b) contacting compound 15 with at least 2 equivalents of a reducing agent under conditions wherein the carbonyl groups are reduced to alcohol groups to provide compound 16:

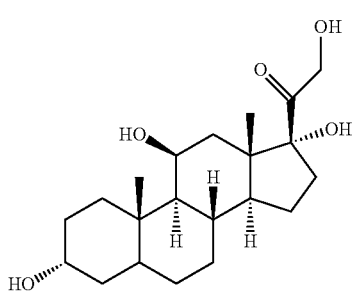

16 c) contacting compound 16 with a vicinal alcohol oxidizing agent under oxidizing conditions to provide compound 17:

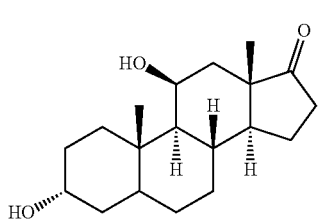

17 d) selectively protecting the 3-hydroxyl group of compound 17 to provide compound 13:

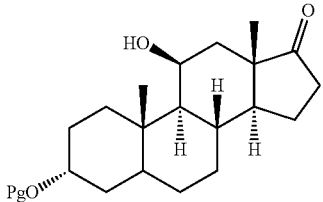

where Pg is a hydroxyl protecting group;

e) contacting the compound of formula 13 under dehydrating conditions to provide compound 12; and

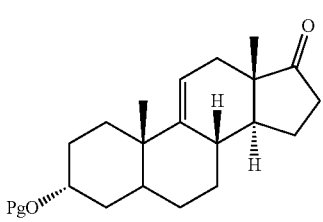

f) and converting compound 12 under olefin forming conditions to form compound 18;

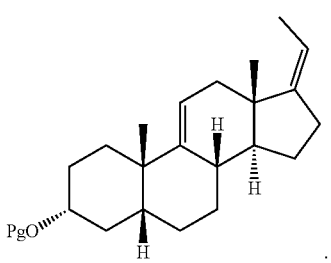

In another embodiment, this invention provides a method of preparing deoxycholic acid or a salt thereof, said method comprising:

a) following the procedures above to provide compound 18;

b) reacting compound 18 with an alkylpropiolate CH≡CC(O)OR' or an alkyl acrylate CH$_2$=CHC(O)OR' wherein R' is alkyl in the presence of a Lewis acid to form compound 19 wherein the dashed line is a single or double bond;

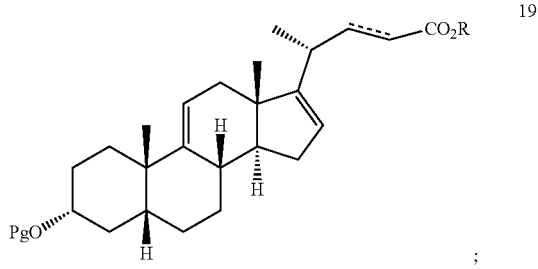

h) reacting the compound of formula 19 with H$_2$ under hydrogenation conditions to form compound 20:

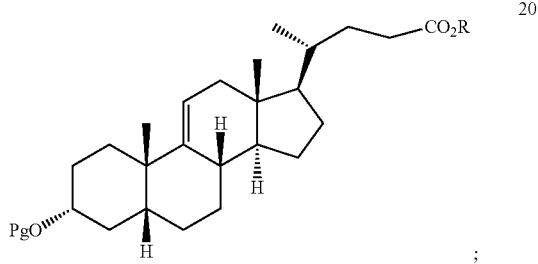

i) reacting compound 20 with an oxidizing agent to provide compound 21:

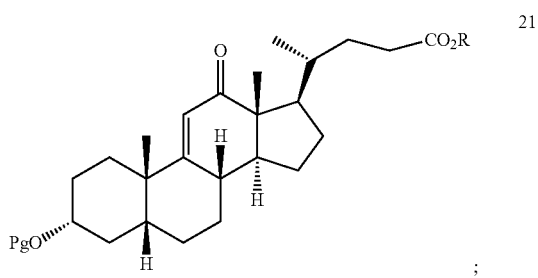

j) reacting compound 21 with H$_2$ under hydrogenation conditions to provide compound 22:

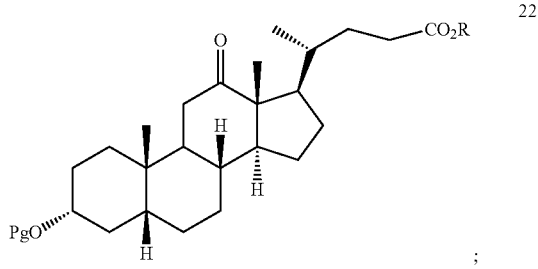

k) reacting compound 22 with a reducing agent to provide compound 23:

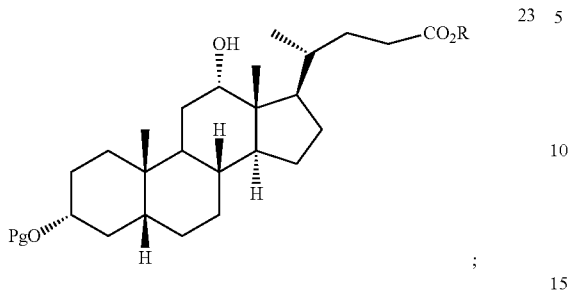

L) contacting compound 23 under deprotection and hydrolysis conditions to form deoxycholic acid or the salt thereof.

In another embodiment, this invention provides a method of preparing compound 24

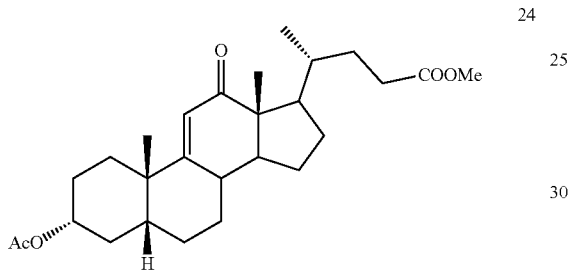

said method comprising:
a) contacting compound 25:

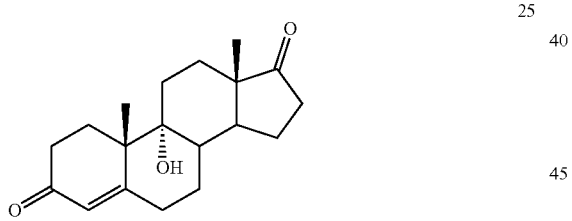

under hydrogenation conditions comprising hydrogen and at least 8% by weight of a 50% wet (with water for safety) Pd on carbon in a solvent selected from the group consisting of acetone, isopropanol, ethyl acetate, N,N-dimethylformamide, and tetrahydrofuran in an autoclave maintained at elevated pressure to provide compound 26:

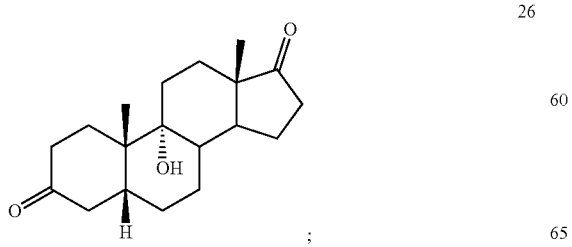

b) dehydration of compound 26 in the presence of sulfuric acid under conditions wherein water is eliminated to provide compound 27:

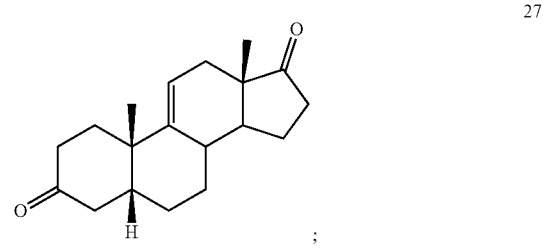 [SMILES: C[C@]12CC=C3C(CC[C@@H]4CC(=O)CC[C@]34C)C1CCC2=O]

c) contacting compound 27 with an excess of lithium tri-t-butoxyaluminum hydride under selective reducing conditions including a temperature of from −40° C. to −45° C. to provide compound 28:

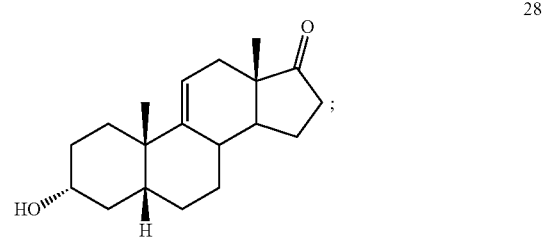 [SMILES: C[C@]12CC=C3C(CC[C@@H]4C[C@H](O)CC[C@]34C)C1CCC2=O]

d) contacting compound 28 with an excess of ethyltri-arylphosphonium halide under Wittig reaction conditions to provide compound 29:

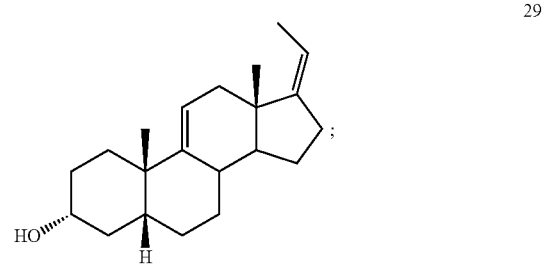 [SMILES: C/C=C1/CCC2C3CC[C@@H]4C[C@H](O)CC[C@]4(C)C3=CC[C@]12C]

e) protecting the 3-α-hydroxy group of compound 29 under acetylation conditions including an excess of anhydrous acetic anhydride to provide compound 30:

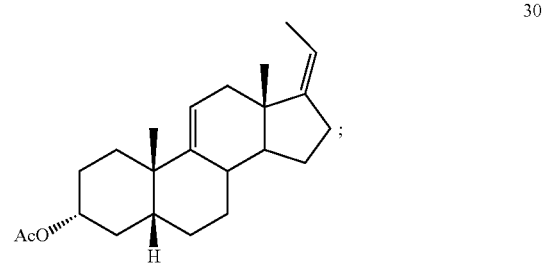 [SMILES: C/C=C1/CCC2C3CC[C@@H]4C[C@H](OC(C)=O)CC[C@]4(C)C3=CC[C@]12C]

f) contacting compound 30 with an excess of methyl acrylate in presence of an excess of $C_1$-$C_2$ alkyl aluminum dichloride under alkylating conditions to form compound 31:

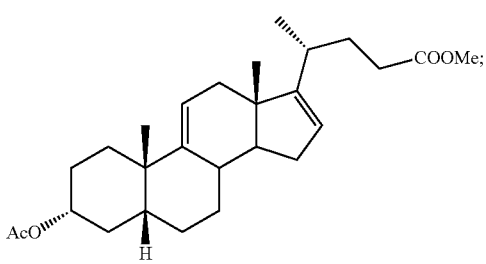

g) contacting compound 31 with hydrogen and a hydrogenation catalyst selected from platinum and dry palladium on carbon in an inert solvent under hydrogenation conditions including an autoclave maintained at an elevated pressure to provide compound 32;

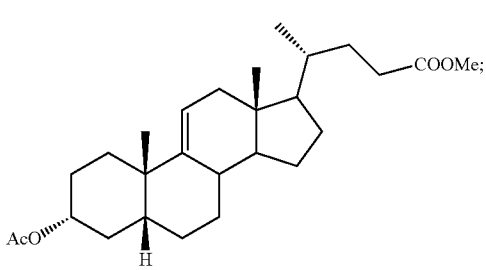

h) contacting compound 32 dissolved in an inert solvent under co-oxidizing conditions including an excess of $C_4$-$C_6$ t-alkyl hydroperoxide as a first oxidant and an excess of NaOCl as a co-oxidant under oxidizing conditions optionally followed by further oxidation with a slight excess of pyridiniumchlorochromate to provide compound 24:

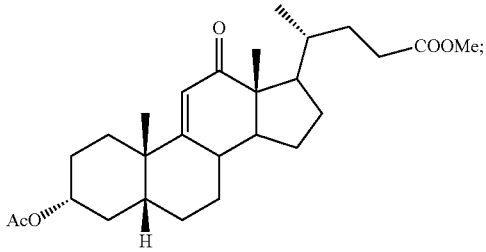

which compound is washed with methanol.

In another embodiment of this invention, there is provided a method for preparing deoxycholic acid or a salt thereof which method comprises:

a) contacting compound 24

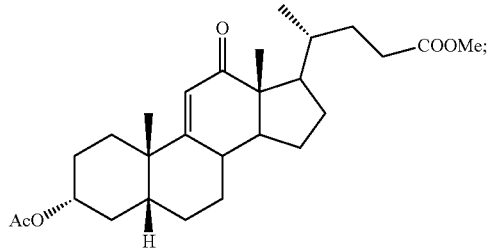

with hydrogen and Pd/C under hydrogenation conditions comprising hydrogen and Pd on carbon in an autoclave maintained at elevated pressure optionally followed by oxidizing any of the 12-hydroxyl groups formed during hydrogenation with pyridiniumchlorochromate under oxidizing conditions to provide compound 33;

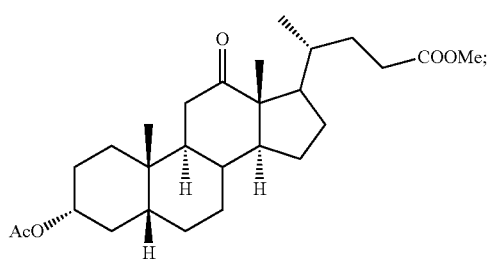

b) reacting compound 33 with lithium tri-t-alkoxyaluminum hydride under reducing conditions to provide compound 34:

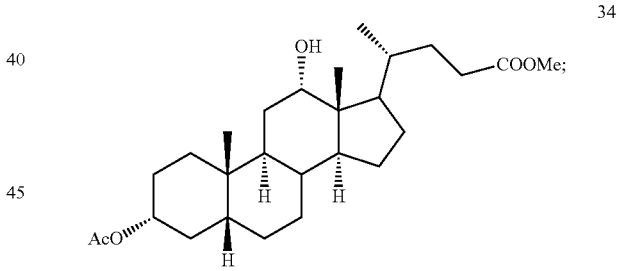

and c) exposing compound 34 to deprotection and hydrolysis conditions to form deoxycholic acid or the salt thereof.

In another embodiment, this invention provides a method of preparing compound 26

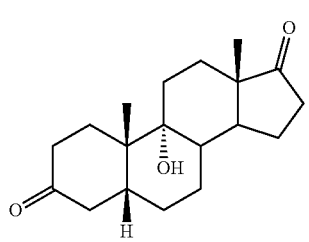

by contacting compound 25:

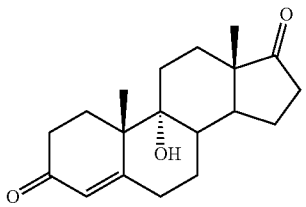

under hydrogenation conditions comprising hydrogen and 10% Pd/C using a solvent selected from the group consisting of N,N-dimethylformamide, acetone, isopropanol, ethyl acetate and aqueous acetone comprising up to 5% water.

In another embodiment, this invention provides a method for preparing deoxycholic acid (DCA) having a purity of greater than 96%, or a salt thereof, which method comprises:

(a) contacting DCA having a purity of about 95% or less with a solvent comprising dichloromethane under conditions to form a DCA solution;

(b) crystallizing the DCA from the DCA solution obtained from step (a) to provide a solution containing crystalline DCA;

(c) recovering the crystalline DCA which has a purity of greater than 96%.

In another embodiment, this invention provides a method for preparing deoxycholic acid (DCA) having a purity of greater than 96%, which method comprises:

(a) contacting DCA having a purity of about 95% or less with a solvent comprising dichloromethane and methanol under conditions to form a DCA solution;

(b) crystallizing the DCA from the DCA solution obtained from step (1) to provide a solution containing crystalline DCA;

(c) recovering the crystalline DCA and removing sufficient amounts of the dichloromethane to provide a purity of greater than 96% for the recovered crystalline DCA.

In another embodiment, this invention provides a synthetic deoxycholic acid (DCA) or a pharmaceutically acceptable salt thereof, wherein the synthetic DCA or the pharmaceutically acceptable salt thereof has a purity of at least 99%.

In another embodiment, this invention provides a composition comprising a DCA having a purity of at least 99% or a pharmaceutically acceptable salt thereof and a pharmaceutically acceptable excipient.

In another embodiment, this invention provides a composition for non-surgical removal of localized fat, said composition consisting essentially of a DCA having a purity of at least 99% or a pharmaceutically acceptable salt thereof wherein the DCA is essentially the sole fat removal component of said composition.

In another embodiment, this invention provides a composition comprising DCA and a solvent, which solvent comprises dichloromethane with or without methanol, wherein the concentration of DCA to solvent is from 40:1 to about 10:1.

DETAILED DESCRIPTION OF THE INVENTION

Figure 1:
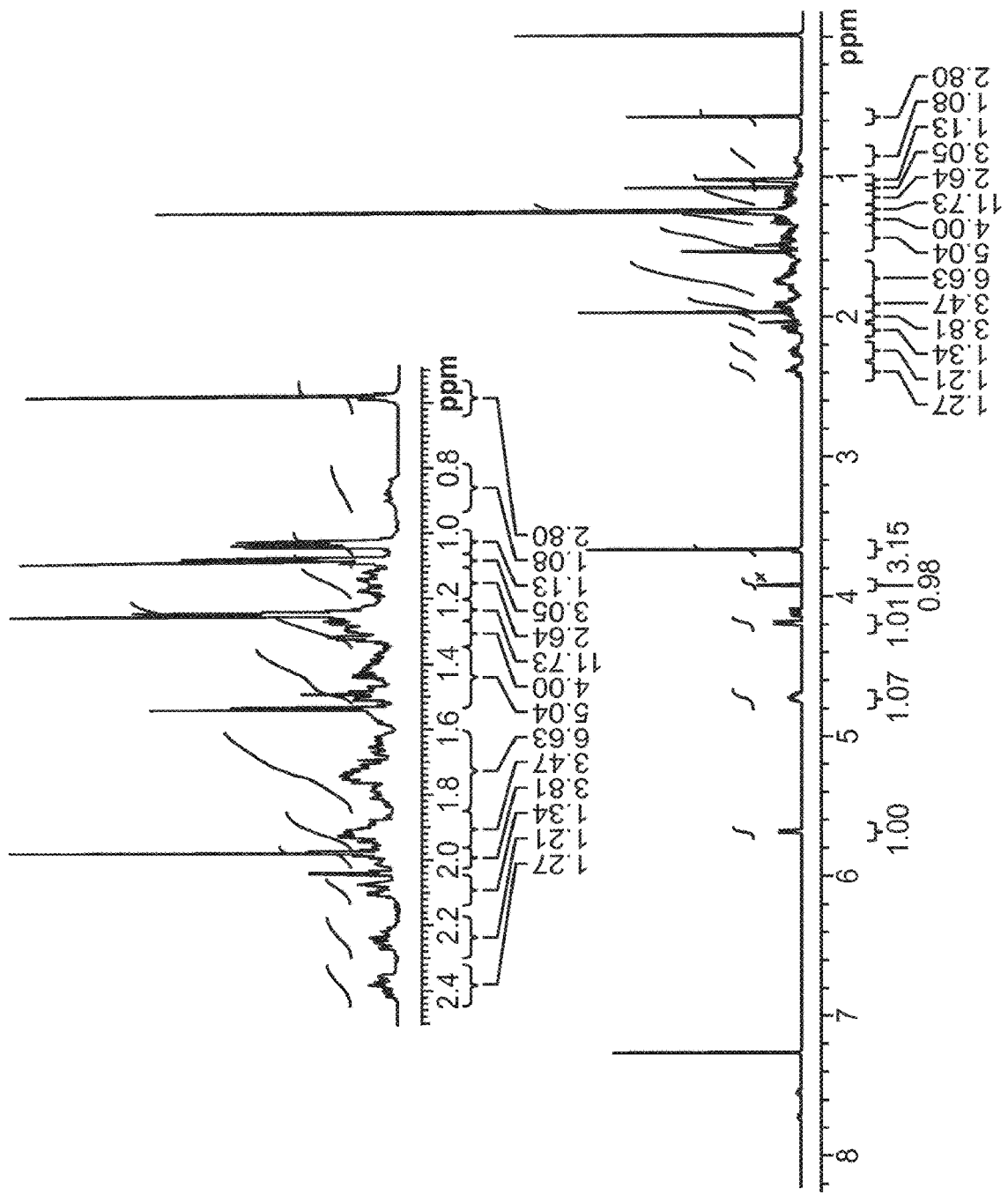
FIG. 1 provides a proton NMR spectrum of compound 9 using a 500 MHz instrument.

Throughout this disclosure, various publications, patents and published patent specifications are referenced by an identifying citation. The disclosures of these publications, patents and published patent specifications are hereby incorporated by reference into the present disclosure to more fully describe the state of the art to which this invention pertains.

As used herein, certain terms may have the following defined meanings. As used in the specification and claims, the singular form "a," "an" and "the" include singular and plural references unless the context clearly dictates otherwise.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations. Each numerical parameter should at least be construed in light of the number of reported significant digits and by applying ordinary rounding techniques.

As used herein, the term "comprising" is intended to mean that the compounds and methods include the recited elements, but not excluding others. "Consisting essentially of" when used to define compositions and methods, shall mean excluding other elements of any essential significance to the compounds or method. "Consisting of" shall mean excluding more than trace elements of other ingredients for claimed compounds and substantial method steps. Embodiments defined by each of these transition terms are within the scope of this invention. Accordingly, it is intended that the methods and compounds can include additional steps and components (comprising) or alternatively include additional steps and compounds of no significance (consisting essentially of) or alternatively, intending only the stated methods steps or compounds (consisting of).

The term "alkyl" refers to monovalent saturated aliphatic hydrocarbyl groups having from 1 to 10 carbon atoms or 1 to 6 carbon atoms. The term "lower alkyl" refers to an alkyl of 1-6 carbon atoms or 1-4 carbon atoms. This term includes, by way of example, linear and branched hydrocarbyl groups such as methyl (CH$_3$—), ethyl (CH$_3$CH$_2$—), n-propyl (CH$_3$CH$_2$CH$_2$—), isopropyl ((CH$_3$)$_2$CH—), n-butyl (CH$_3$CH$_2$CH$_2$CH$_2$—), isobutyl ((CH$_3$)$_2$CHCH$_2$—), sec-butyl ((CH$_3$)(CH$_3$CH$_2$)CH—), t-butyl ((CH$_3$)$_3$C—), n-pentyl (CH$_3$CH$_2$CH$_2$CH$_2$CH$_2$—), and neopentyl ((CH$_3$)$_3$CCH$_2$—).

The term "t-alkyl" or "tert-alkyl" refers to tertiary alkyl groups of the formula R$^1$R$^2$R$^3$C— where each of R$^1$, R$^2$ and R$^3$ are independently alkyl of from 1 to 3 carbon atoms and a total of 10 carbon atoms. Such groups preferably have no more than 4-6 carbon atoms.

The term "oxidizing agent" refers to a reagent which can accept electrons in an oxidation-reduction reaction. In this way, oxygen can be added to a molecule or hydrogen can be removed from a molecule. Oxidizing agents include by way of example only Jones reagent, tert-butyl hydroperoxide, sodium hypochlorite, pyridinium chlorochromate and CrO$_3$. In one example, the oxidizing agent is specific to vicinal (1,2) alcohols and include periodate compounds. Such oxidizing agents are sometimes referred to as "vicinal alcohol oxidizing agents".

The term "chromium oxidizing agents" refers to chromium VI compounds capable of effecting oxidation. In one embodiment, the chromium oxidizing agent is capable of oxidizing primary alcohols to aldehydes and secondary alcohols to ketones. Such selective chromium oxidizing agents are typically complexed with a base such as pyridine. One particularly preferred chromium oxidizing agent is pyridiniumchlorochromate. In another embodiment, the chromium oxidizing agent is capable of oxidizing a methylene group alpha to vinyl unsaturation to effect formation of an allylic ketone. In that embodiment, preferred chromium oxidizing agents include chromium trioxide and a co-oxidant mixture of NaOCl and t-alkyl hydrogen peroxide such as t-butyl hydrogen peroxide (TBHP).

The term "hydroxy protecting group" refers to a group capable of protecting the hydroxy (—OH) group of a compound and releasing the hydroxy group under suitable deprotection conditions. Common such groups include acyl (which forms an ester with the oxygen atom of the hydroxy group), such as acetyl, benzoyl, and groups that form an ether with the oxygen atom of the hydroxy group, such as benzyl and methoxymethyl, etc. Hydroxy protecting groups are well known in the field of organic synthesis.

The term "elimination conditions" refers to reaction conditions in which a small molecule, such as $H_2O$, HCl, or HBr, etc., is lost from a compound comprising a hydroxyl, chloro, or bromo group, etc. to form a corresponding compound comprising an alkenyl group. In one example, an elimination condition includes dehydration conditions wherein the hydroxyl group and the vicinal hydrogen atom are eliminated to form a vinyl group (an "ene") group. Dehydration conditions may include converting the hydroxyl group to a leaving group such as chloro, bromo, tosyl, mesyl, —OS(O)CL.

The term "Ac" refers to an acetyl group which has the formula $CH_3C(O)$—.

The term "keto" refers to the group (>C=O).

The term "keto protecting group" refers to a group capable of protecting a keto group of a compound and releasing the keto group under suitable deprotection conditions. Common such groups include ketals and acylals. Keto protecting groups are well known in the field of organic synthesis.

Suitable hydroxy or keto protecting groups and other protecting groups which may be employed, and the conditions for their removal, are described in books such as *Protective groups in organic synthesis,* 3 ed., T. W. Greene and P. G. M. Wuts, eds., John Wiley & Sons, Inc., New York, N.Y., U.S.A., 1999, and will be well known to a person of ordinary skill in the art, which is incorporated by reference in its entirety.

The term "ketal" refers to a group having two —$OR^{22}$ groups attached to the same carbon atom in a molecule, where $R^{22}$ represents an alkyl group or the two $R^{22}$ groups together with the carbon atom and the two oxygen atoms attached thereto form a ring structure. The two —$OR^{22}$ groups may be the same or different.

The term "acylal" refers to a group having two —$O(C=O)R^{23}$ groups attached to the same carbon atom in a molecule, where $R^{23}$ represents an alkyl group or the two $R^{23}$ groups together with the carbon atom and the two —$O(C=O)$— groups attached thereto form a ring structure. The two —$O(C=O)R^{23}$ groups may be the same or different.

The term "reducing agent" refers to a reagent which can donate electrons in an oxidation-reduction reaction, allowing hydrogen to be added to a molecule. Suitable reducing agents include lithium aluminum hydride, sodium borohydride, sodium cyanoborohydride, and the like.

The term "acetylating reagent" refers to a reagent in which can add an acetyl (Ac) group $CH_3C(O)$— to an alcohol moiety of a molecule.

The term "acid" refers to regents capable of donating $H^+$.

The term "Lewis acid" refers to an electron pair acceptor. Lewis acids include oraganometallic reagents such as alkyl aluminum halides (e.g. $Et_2AlCl$ and $MeAlCl_2$).

The term "hydrogenation conditions" refers to suitable conditions and catalysts for introducing $H_2$ across one or more double bonds. Hydrogenation catalysts include those based on platinum group metals (platinum, palladium, rhodium, and ruthenium) such as Pd/C and $PtO_2$.

The term "olefination reagent" refers to regents that react with ketones to form the corresponding olefins. The term "olefin forming conditions" refers to suitable conditions for carryout such transformations. Examples of such reagents include Wittig reagents and Wittig olefination conditions.

The term "reflux conditions" refers to conditions wherein a liquid boils, and the vapor of the boiling liquid condenses and runs back down into the liquid below.

The term "pharmaceutically acceptable salt" refers to pharmaceutically acceptable salts of deoxycholic acid, which salts are derived from a variety of organic and inorganic counter ions well known in the art and include, by way of example only, sodium, potassium, calcium, magnesium, ammonium, and tetraalkylammonium.

The numbering of the steroidal scaffold as used herein follows the general convention:

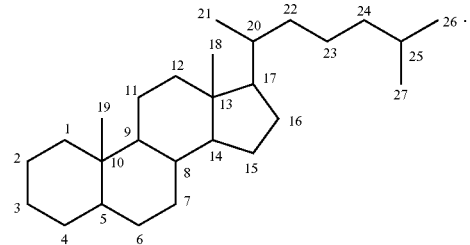

It is to be understood that unless otherwise specified, the scaffolds only represents the position of carbon atoms. One or more bonds between two adjacent carbon atoms may be a double bond and one or more of carbon atoms be may optionally substituted.

The term "Δ-9,11-ene steroidal" or "Δ-9,11-ene compound" as used herein refers to a steroidal compound having a double bond between the 9 and 11 carbon atoms which can be represented by the scaffold of:

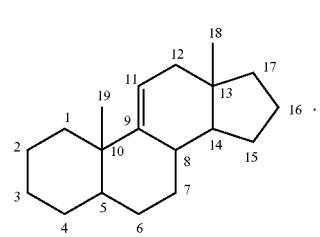

the term "11-β-hydroxy steroidal" or "11-β-hydroxy compound" as used herein refers to a steroidal compound having a hydroxy substituent on the 11-position carbon atom which can be represented by the scaffold of:

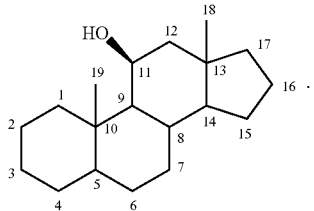

The term "11-keto steroidal" or "11-keto compound" as used herein refers to a steroidal compound having a keto substituent on the 11-position carbon atom which can be represented by the scaffold of:

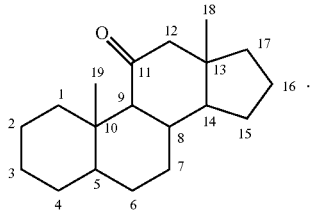

The term "12-keto steroidal" or "12-keto compound" as used herein refers to a steroidal compound having a keto substituent on the 12-position carbon atom which can be represented by the scaffold of:

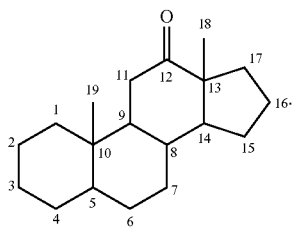

The term "12-alpha-hydroxy steroidal" or "12-alpha-hydroxy compound" as used herein refers to a steroidal compound having a hydroxy substituent on the 12-position carbon atom which can be represented by the scaffold of:

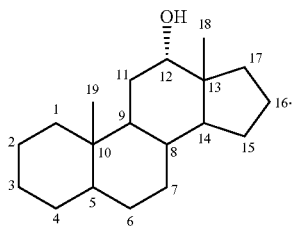 [SMILES: CC12CCCCC1CCC1C2C[C@H](O)C2(C)CCCC12]

The term "17-side chain of a bile acid" refers the substituent on the 17-position carbon atom.

Synthetic Processes
A. Synthesis of DCA from Hydrocortisone

In one embodiment, this invention provides a synthesis of compound 14 which is an intermediate for synthesizing deoxycholic acid (DCA), or a pharmaceutically acceptable salt thereof.

Scheme 1. Synthese of 3α-hydroxy-5β-androst-9(11)-en-17-one (14) from Hydrocortisone

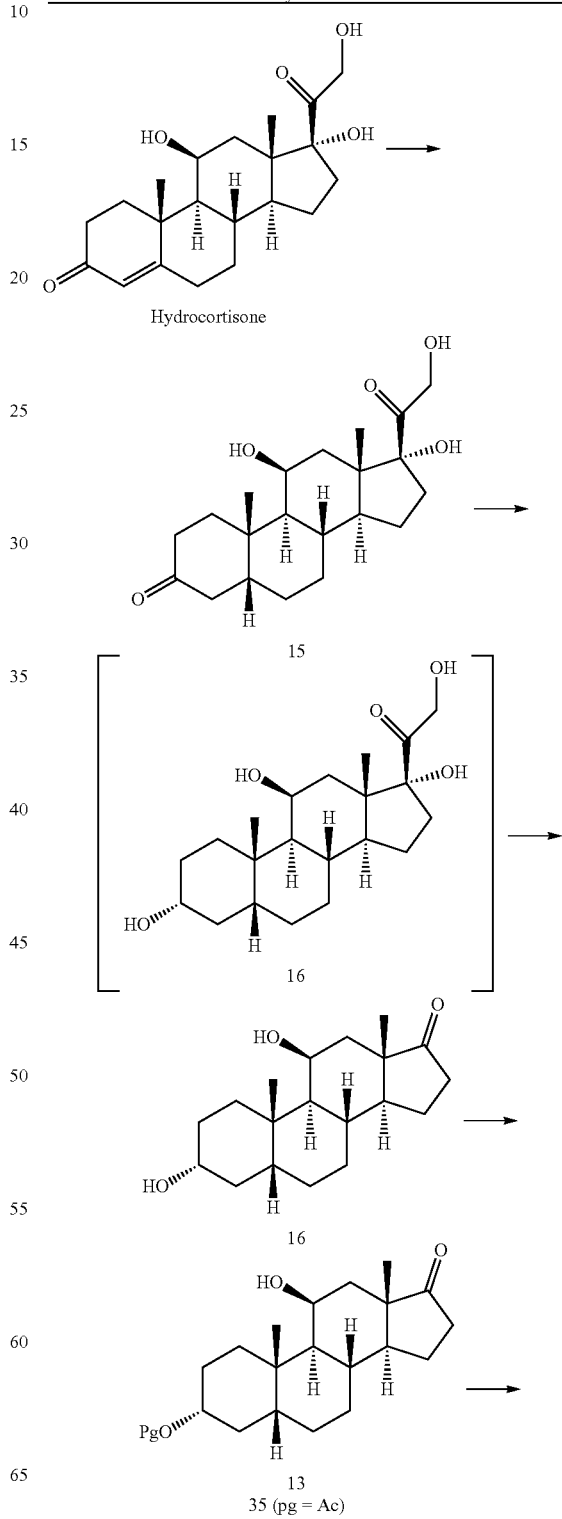

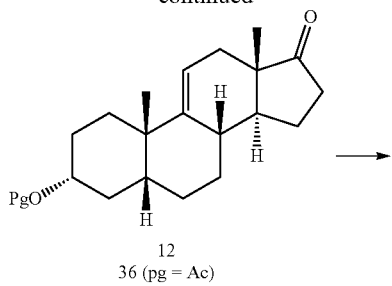

12
36 (pg = Ac)

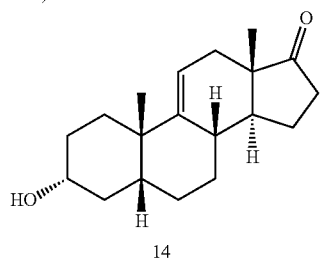

14 where Pg is a protecting group.

This method comprises exposing compound 13 (the synthesis of which is described below):

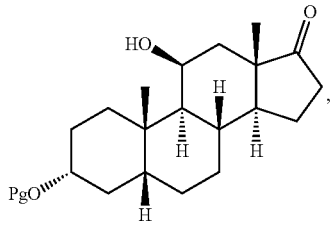

13 where Pg is a hydroxyl protecting group, to dehydrating conditions to provide compound 12

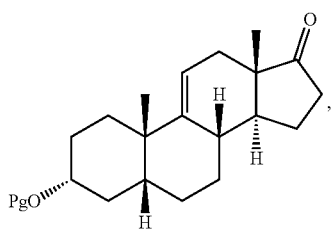

12 and removing the hydroxyl protecting group.

In some embodiments, Pg is —C(O)R$^1$, wherein R$^1$ is lower alkyl. In some embodiments, Pg is —C(O)CH$_3$.

In one embodiment, the dehydration conditions comprise converting the hydroxyl group of the compound of formula 13 to -L, where -L is a leaving group, such as —OS(O)CL, —OSO$_2$R$^2$ (wherein R$^2$ is lower alkyl or phenyl or phenyl substituted with alkyl, for example, —CH$_3$ or —C$_6$H$_5$CH$_3$), or —OPX$_2$ (wherein X is bromo or OR$^3$, wherein R$^3$ is lower alkyl). In some embodiments, the dehydration conditions comprise thionyl chloride and pyridine.

In some embodiments, compound 13 is prepared by a method comprising selectively protecting the 3-hydroxyl group of compound 17:

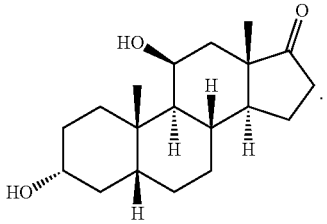

17

In one embodiment, the protecting group Pg is —C(O)-lower alkyl, for example, —C(O)CH$_3$. In some embodiments, compound 17 is exposed to acylation conditions to form 35, such as by treatment of 17 with acetic anhydride and an organic base such as triethylamine (Et$_3$N), pyridine, and/or dimethylaminopyridine.

In some embodiments, compound 17 is prepared by a method comprising contacting compound 16

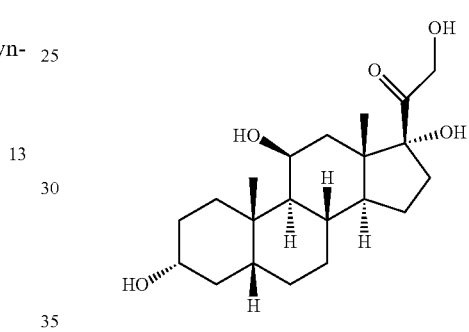

16 with a vicinal alcohol oxidizing agent under oxidizing conditions.

In some embodiments, the vicinal alcohol oxidizing agent is lead tetraacetate (Pb(OAc)$_4$) or sodium periodate (NaIO$_4$).

In some embodiments, compound 16 is prepared by a method comprising contacting compound 15

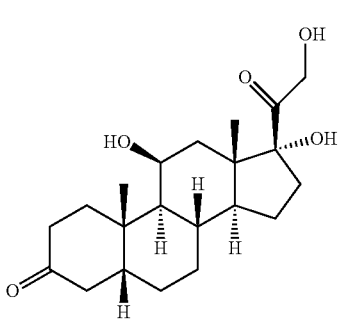

15 with at least 2 equivalents of a reducing agent under conditions wherein the carbonyl groups are reduced to alcohol groups.

In some embodiments, the reducing agent comprises sodium borohydride, sodium cyanoborohydride, lithium aluminum hydride and the like.

In some embodiments, compound 15 is prepared by a method comprising reacting hydrocortisone:

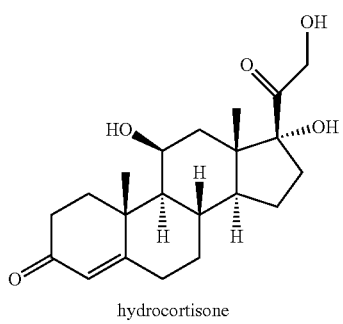

hydrocortisone with at least a molar equivalent of hydrogen under hydrogenation conditions.

In some embodiments, the hydrogenation conditions comprise Pd/C as a catalyst. In some embodiments, the hydrogenation conditions comprise DMF as a solvent.

In some embodiments, the method of preparing compound 12 comprises:

a) contacting hydrocortisone:

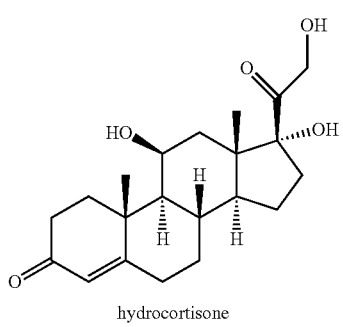

hydrocortisone with at least a molar equivalent of hydrogen under hydrogenation conditions to provide 4,5-β-dihydrohydrocortisone—compound 15:

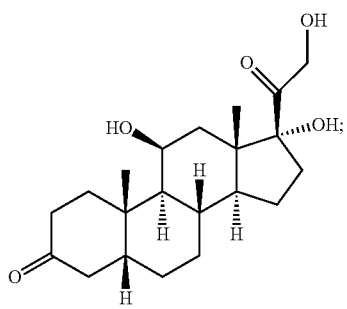

15 b) contacting compound 15 with at least 2 equivalents of a reducing agent under conditions wherein the carbonyl groups are reduced to alcohol groups to provide compound 16:

c) contacting compound 16 with a vicinal alcohol oxidizing agent under oxidizing conditions to provide compound 17:

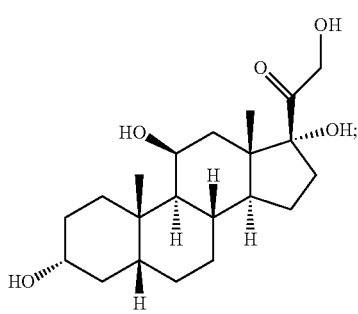

16

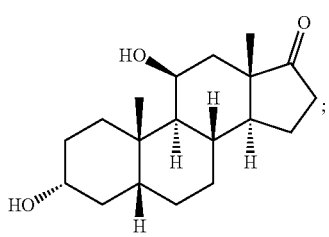

17 d) selectively protecting the 3-hydroxyl group of compound 17 to provide compound 13:

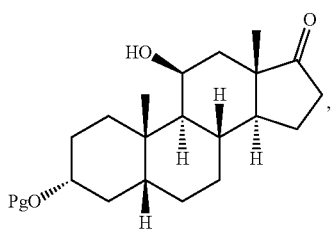

13 where Pg is a hydroxyl protecting group;

e) subjecting compound 13 to dehydrating conditions to provide compound 12:

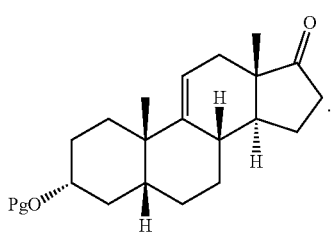

12

In another aspect, this invention provides a method of preparing compound 28 comprising exposing compound 12 to deprotection conditions. In some embodiments, Pg is —C(O) lower alkyl and the deprotection conditions comprise hydrolysis conditions. In some embodiments, the hydrolysis conditions comprise alkaline metal hydroxide or alkaline metal alkoxide and water.

In some embodiments, this invention provides a method of preparing DCA or a salt thereof, said method comprising:
a-e) preparing compound 12 as described above

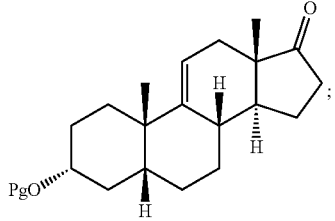

12 f) converting compound 12 under olefin forming conditions to form compound 18

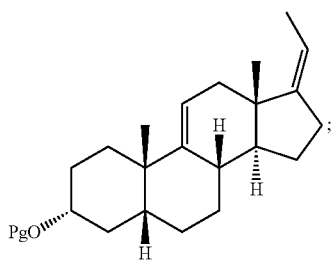

18 g) reacting compound 18 with an alkylpropiolate CH≡CC(O)OR or an alkyl acrylate CH$_2$=CHC(O)OR wherein R is alkyl in the presence of a Lewis acid to form compound 19 wherein the dashed line ⹀ is a single or double bond

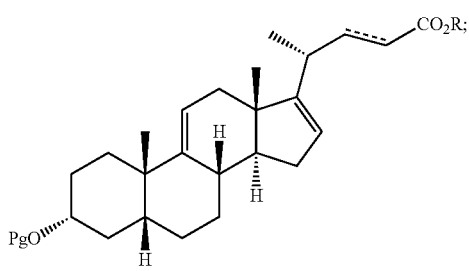

19 h) reacting the compound of formula 19 with H$_2$ under hydrogenation conditions to form compound 20

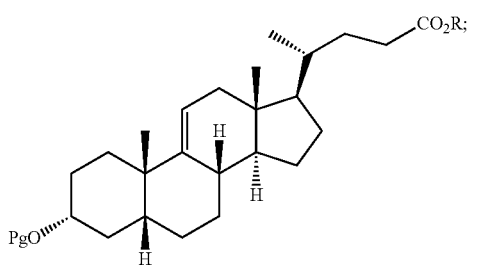

20 i) reacting compound 20 with an oxidizing agent to form compound 21

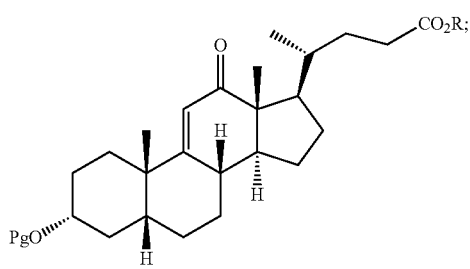

21 j) reacting compound 21 with H$_2$ under hydrogenation conditions to form compound 22

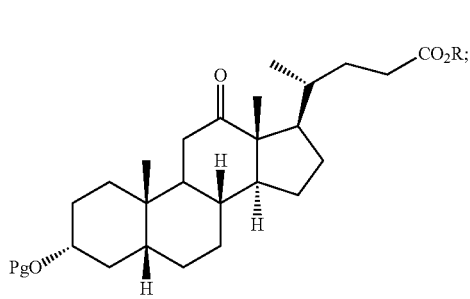

22 k) reacting compound 22 with a reducing agent to form compound 23

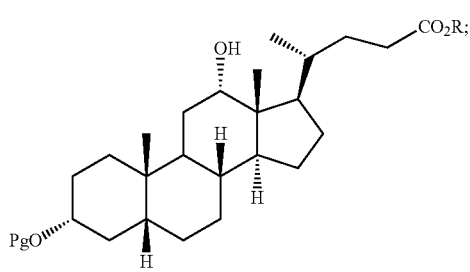

23 and l) exposing compound 23 to deprotection and hydrolysis conditions to form deoxycholic acid or the salt thereof.

In one embodiment, the hydrogenation conditions of part a) comprise a Pd/C catalyst. In some embodiments, the hydrogenation conditions comprise a solvent DMF as a solvent.

In one embodiment, the reducing agent of part b) is NaBH$_4$.

In one embodiment, the vicinal alcohol oxidizing agent of part c) is NaIO$_4$.

In one embodiment, the protecting group Pg of the compound of formulas 13-23 is —C(O)-lower alkyl, for example, —C(O)CH$_3$. In some embodiments, compound 17 is exposed to acylation conditions to form 35, such as by treatment of 17 with acetic anhydride and an organic base such as Et$_3$N, pyridine, and/or dimethylaminopyridine.

In one embodiment, the dehydrating conditions of step e) comprise converting the hydroxyl group of the compound of formula 13 to -L, where -L is a leaving group, such as —OS(O)C₁, —OSO₂R² (wherein R² is lower alkyl or phenyl or phenyl substituted with alkyl, for example, —CH₃, —C₆H₅CH₃), —OPX₂ (wherein X is bromo or OR³, wherein R³ is lower alkyl). In some embodiments, the dehydrating conditions comprise thionyl chloride and pyridine.

In one embodiment, the olefin forming conditions of part f) comprise a Wittig agent such as Ph₃PCH₂CH₃⁺Br⁻.

In one embodiment, the Lewis acid of part g) is EtAlCl₂.

In one embodiment, the alkylpropiolate of part g) is methylpropriolate.

In one embodiment, the alkyl acrylate of part g) is methylacrylate.

In one embodiment, the hydrogenation conditions of part h) comprise a PtO₂ or Pd/C catalyst.

In one embodiment, the oxidizing agent of part i) is CrO₃.

In one embodiment, the oxidizing agent of part i) comprises tert-butyl hydroperoxide. In one embodiment, the oxidizing agent of part i) comprises an excess of tert-butyl hydroperoxide (e.g. about 35 equivalents) and an excess of sodium hypochlorite (e.g. about 7 equivalents) at a low temperature (e.g. about 0-5° C.). In another embodiment, the oxidizing agent of part i) comprises a palladium reagent (e.g. Pd/C), an excess of tert-butyl hydroperoxide (e.g. about 5 equivalents) and potassium carbonate in dichloromethane (DCM).

In one embodiment, the hydrogenation conditions of part j) comprise a Pd/C catalyst.

In one embodiment, the reducing agent of part k) is LiAl(OtBu)₃H.

In one embodiment, the deprotection and hydrolysis conditions of part l) when Pg is —C(O)CH₃ comprise reacting compound 38 with an alkali metal hydroxide, alkali metal alkoxide, or a mixture of both.

In one embodiment, the alkali metal hydroxide is LiOH or NaOH.

In one embodiment, salts of deoyxcholic acid can be prepared by reaction with an alkali metal alkoxide or hydroxide. Salts of deoxycholic acid include the sodium (Na⁺), potassium (K⁺), and lithium (Li⁺) salts.

In one embodiment, this invention provides side products as shown in Example 3 which can be recycled by chemical modification to be used as intermediates in the methods described herein.

B. Conversion of 11-β-hydroxy/11-keto steroids to the corresponding 12-α-hydroxy/12-ketosteroids In another embodiment, this invention provides synthetic processes for the efficient conversion of 11-β-hydroxy/11-keto steroids to the corresponding 12-α-hydroxy/12-ketosteroids which compounds are useful in the synthesis of bile acids. The processes preferably employ steroids such as 9-HAD, cortisone or hydrocortisone, which may also be prepared synthetically and converted to compound 4 by methods described, for example, in U.S. Provisional Patent Application No. 61/303,816, filed on Feb. 12, 2010, titled "Preparation of Deoxycholic Acid and Intermediates Thereof," which is incorporated herein by reference in its entirety.

In one of its process aspects, this invention is directed to a process for converting a Δ-9,11-ene compound 4:

to the corresponding 12-keto compound 3:

where Pg is a hydroxyl protecting group, R is hydrogen, hydroxyl, or —OPg, R¹ is the 17-side chain of a bile acid, which bile acid is selected from the group consisting of cholic acid, deoxycholic acid, taurocholic acid, and glycocholic acid, wherein the carboxyl functionality of said side chain is optionally esterified with a C₁-C₆ alkyl group, and R² is hydrogen, or R¹ and R² together with the carbon atom attached thereto form a keto group or a keto protecting group, such as a ketal;

wherein said process comprises:

effecting allylic oxidation at the 12-position of compound 4 by reaction with an t-alkylhydroperoxide of the formula (R³)(R⁴)(R⁵)C—O—OH in the presence of a co-oxidant, wherein each of R³, R⁴, and R⁵ is independently C₁-C₃ alkyl, to first provide a mixture of compounds 1, 2 and 3:

-continued

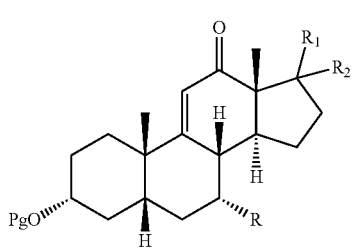
3 and wherein compound 1 and/or 2 is optionally further converted to provide the Δ-9,11-ene-12-one compound 3.

In some embodiments, the t-alkylhydroperoxide is tert-butylhydroperoxide.

The co-oxidant is typically any oxidizing agent which works in concert with the alkylhydroperoxide to effect oxidation at the 12-position albeit whether the oxidation provides an allylic keto, an allylic alcohol or an allylic peroxide as shown above in formulas 1, 2, and 3. In some embodiments, the co-oxidant is aqueous sodium hypochlorite (NaOCl). In one embodiment, the allylic oxidation at the 12-position of compound 4 is effected by an excess of tert-butyl hydroperoxide (e.g. at or above 1.5 equivalents, at or above 6 equivalents, at or above 10 equivalents or about 35 equivalents) and an excess of sodium hypochlorite (e.g. about 7 equivalents) at a low temperature (e.g. at or below 22° C., at or below 10° C., and about 0-5° C.). The tert-butyl hydroperoxide may be added as an aqueous solution in a concentration of, for example, about 70%. The sodium hypochlorite may be added as an aqueous solution in a concentration of, for example, about 2.5% to 13%, about 5%, or 10%. In some embodiments, the allylic oxidation is effected in a solvent selected from the group consisting of water, ethyl acetate, hexane, heptanes, toluene, t-butyl alcohol, dimethoxypropane, petroleum ether, and dicholoroethane, or combinations thereof. In some embodiments, a phase transfer catalyst can be employed. The use of these co-oxidants provides for oxidation without the use of the toxic chromium VI oxidants.

In some embodiments, the co-oxidant is a metal compound such as CuI.

In some embodiments, the allylic oxidation is effected in the presence of palladium on charcoal and a base. In another embodiment, the allylic oxidation at the 12-position of compound 4 is effected by a palladium reagent (e.g. Pd/C, Pd(OAc)$_2$-BINAP, Pd(OCOCF$_3$)$_2$ or Pd(OAc)$_2$ on charcoal), an excess of tert-butyl hydroperoxide (e.g. about 5 equivalents) and potassium carbonate or sodium biphosphate in a solvent, such as DCM.

In some embodiments, the conversion of compound 1 to compound 3 comprises addition a palladium reagent (e.g. Pd/C, Pd(OAc)$_2$ BINAP, Pd(OCOCF$_3$)$_2$ or Pd(OAc)$_2$ on charcoal), an excess of tert-butyl hydroperoxide (e.g. about 5 equivalents) and potassium carbonate or sodium biphosphate in a solvent, such as DCM.

In some embodiments, the oxidation of compound 2 comprises addition of an oxidizing agent capable of oxidizing an alcohol functionality (—OH) to a keto functionality (═O), which are known in the art, for example, pyridinium chlorochromate (PCC). When so used, the amount of pyridinium chlorochromate employed is significantly less than use of chromium [VI] trioxide. For example, in a preferred embodiment, the pyridinium chlorochromate is employed at a molar ratio of about 1 to 1.5 to compound 2 and preferably at about a molar ratio of 1.1. This compares favorably with the amount of chromium trioxide used previously to effect oxidation—about 4 times more.

In some embodiments, compound 1 is first isolated from the mixture and then converted to compound 2 by reduction with, for example, a reducing agent such as aluminum amalgam or catalytic hydrogenation.

In another of its process aspects, this invention is directed to a two-step process of converting a mixture of compounds 1, 2 and 3:

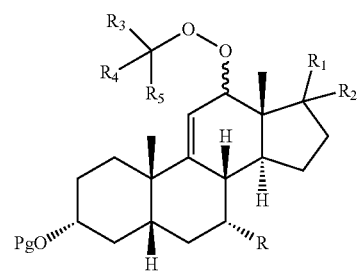
1

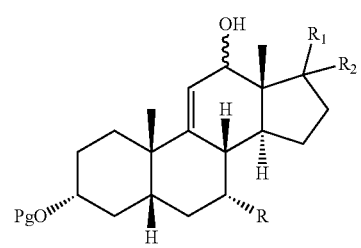
2

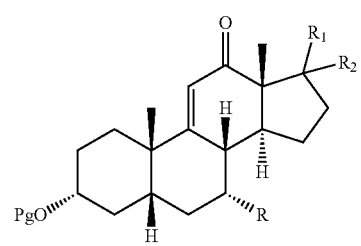
3 to the corresponding 12-keto compound 39:

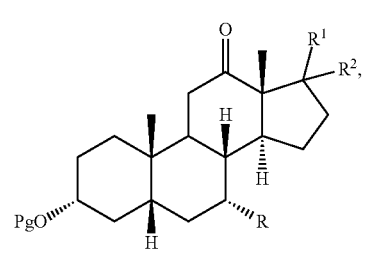
39 where each of Pg, R, $R^1$, $R^2$, $R^3$, $R^4$, and $R^5$ are as defined above, wherein said process comprises first reacting said mixture under hydrogenation conditions; and then reacting the product formed thereby under oxidation conditions.

In some embodiments, the hydrogenation of the mixture of compounds 1, 2 and 3 forms a mixture of compounds comprising compounds 5, 6 and 39:

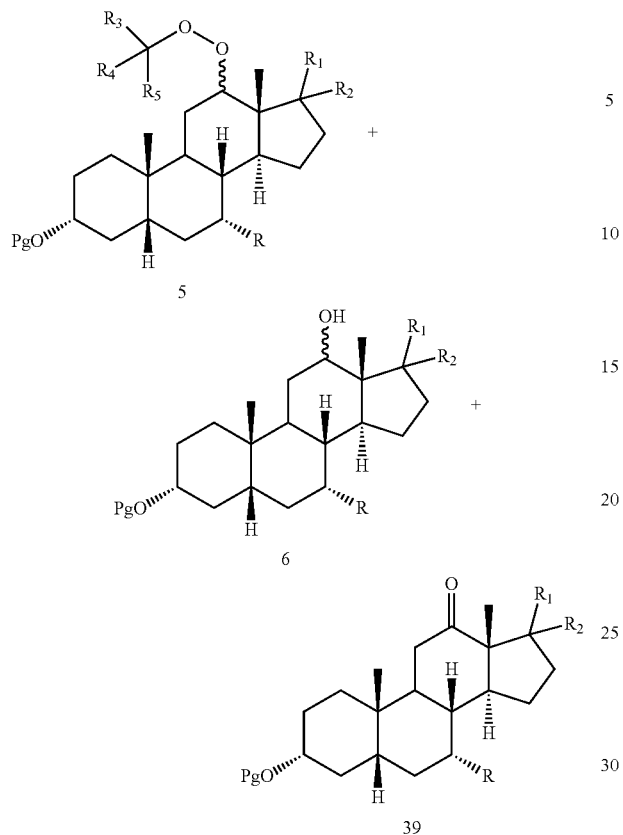

5

6

39

In some embodiments, the hydrogenation conditions comprise hydrogen gas, a catalyst and a solvent. In some embodiments, the catalyst is selected from the group consisting of platinum (Pt), palladium (Pd), rhodium (Rh), and ruthenium (Ru) based catalysts, such as Pd/C, RhCl(PPh$_3$)$_3$ and PtO$_2$. In some embodiments, the solvent is ethyl acetate (AcOEt).

In some embodiments, the oxidation conditions comprises an oxidizing agent capable of oxidizing an alcohol functionality (—OH) to a keto functionality (=O) which are known in the art.

Oxidation conditions known in the art include, but are not limited to, Corey-Kim oxidation (using N-chlorosuccinimide and dimethyl sulfide), Dess-Martin oxidation (using 2-iodoxybenzoic acid or Dess-Martin periodinane), Jones oxidation (using CrO$_3$), and Swern Oxidation (using dimethyl sulfoxide and oxalyl chloride).

In some embodiments, the oxidizing agent is pyridinium chlorochromate (PCC). Other oxidizing agent may include, but are not limited to, pyridinium dichromate, sodium percarbonate, iodoxybenzoic acid, V$_2$O$_5$, Na$_2$Cr$_2$O$_7$, CrO$_3$, sodium percarbonate, urea hydrogen peroxide, and oxone, etc.

When R$^1$ and R$^2$ together with the carbon atom attached thereto form a keto group, the keto group can be converted to the 17-position side chain of a bile acid by methods known in the art, such as those described in WO2008/157635, which is incorporated herein by reference in its entirety.

In one of its process aspects, the process further comprises reducing compound 39 to provide compound 40:

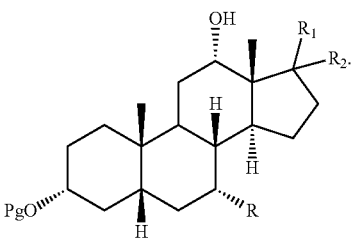

40

In some embodiments, the reduction of compound 39 to provide compound 40 comprises addition of reduction agent capable of stereoselectively, preferably stereospecifically, reducing a keto functionality (=O) to an alcohol functionality (—OH), for example lithium tri-tert-butoxyaluminum hydride.

In some embodiments, R$^1$ and R$^2$ together with the carbon atom attached thereto form a keto group.

In some embodiments, R$^1$ and R$^2$ together with the carbon atom attached thereto form a keto protecting group, such as:

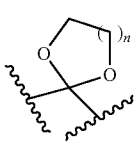

wherein n is 1, 2, or 3 and the wavy line ∿ represents the point of connection to the rest of the molecule.

In some embodiments, R$^1$ is the 17-side chain of a bile acid, which bile acid is selected from the group consisting of cholic acid, deoxycholic acid, taurocholic acid, and glycocholic acid. In some embodiments, the carboxyl functionality of said side chains is optionally esterified with a C$_1$-C$_6$ alkyl group, for example a C$_1$-C$_4$ alkyl group, such as a methyl group.

In some embodiments, R$^1$ is selected from the group consisting of

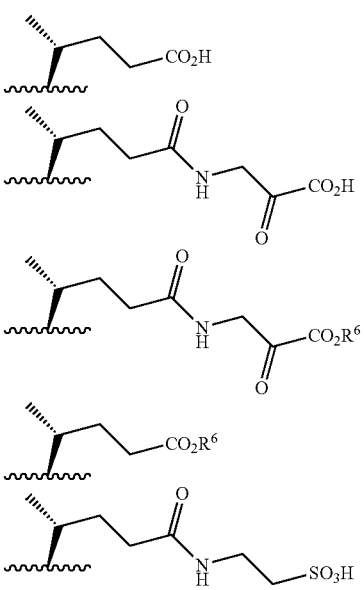

-continued

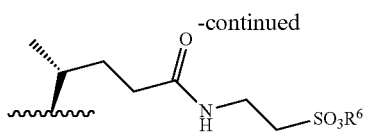

wherein $R^6$ is lower alkyl and the wavy line ∼∼∼ represents the point of connection to the 17-position of steroidal scaffold.

In some embodiments, Pg is —C(O)$R^{12}$, wherein $R^{12}$ is lower alkyl optionally substituted with one to five substituents selected from the group consisting of halo, —O$R^{13}$; and phenyl optionally substituted with one to five substituents selected from the group consisting of halo, lower alkyl, and —O$R^{13}$; wherein $R^{13}$ is hydrogen or lower alkyl. In some embodiments, Pg is —C(O)CH$_3$ or —C(O)CH$_2$CH$_3$. In some embodiments, Pg is:

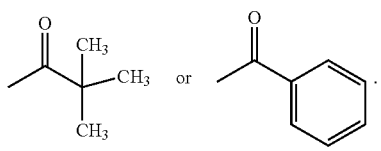

In some embodiments, Pg is —$R^{14}$, wherein $R^{14}$ is selected from the group consisting of lower alkyl optionally substituted with phenyl, —O$R^{13}$ or vinyl (—CH=CH$_2$); —Si($R^{15}$)$_3$; heterocycloalkyl; and phenyl optionally substituted with one to five substituents selected from the group consisting of halo, lower alkyl, and —O$R^{13}$; wherein $R^{13}$ is hydrogen or lower alkyl and each $R^{15}$ is independently selected from the group consisting of lower alkyl and phenyl. In some embodiments, Pg is selected from the group consisting of:

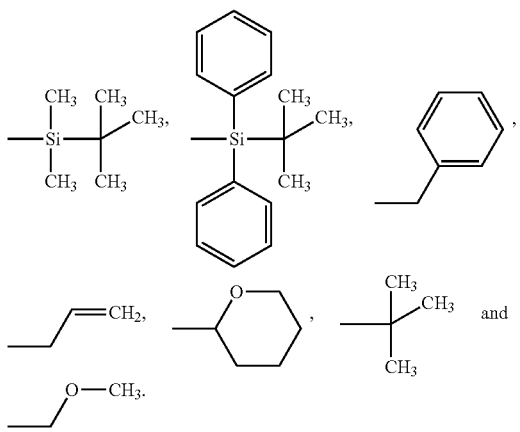

The process of this invention employs conversion of an 11-β-hydroxy steroid (which may be prepared from a corresponding 11-ketosteroid by conventional reduction reaction of the keto group) followed by dehydration to provide a Δ-9,11-ene steroid, which is oxidized to the corresponding 12-keto steroid by an alkylhydroperoxide. This process provides unexpectedly high yields as compared with previously known processes using oxidizing agent such as CrO$_3$ to convert the Δ-9,11-ene steroid to the 12-keto steroid. As shown in the table in Example 2 below, the yield of using CrO$_3$ during the preparation of deoxycholic acid was typically less than 50% or less than 40%. Using the process of this invention, unexpectedly high yields of over 60% were obtained consistently. Moreover, the use of NaOCl (bleach) and TBHP is significantly more environmentally compatible than chromium (VI) oxidizing agents.

In another of its process aspects, this invention is directed to a process for converting an 11-β-hydroxysteroid to the corresponding 12-ketosteroid wherein said process comprises:

a) selecting an appropriately protected 11-β-hydroxysteroid;

b) dehydrating the 11-β-hydroxysteroid to provide the Δ-9,11-ene functionality in said steroid;

c) effecting allylic oxidation at the 12-position by reacting the steroid product of b) above with alkylhydroperoxide in the presence of a co-oxidant; and d) hydrogenating the Δ-9,11-ene functionality to yield the 9-α-hydro-11-dihydro-12-ketosteroid; and e) optionally reducing the 12-keto functionality of the 9-α-hydro-11-dihydro-12-ketosteroid produced in d) above with an effective amount of a reducing agent to provide the 9-α-hydro-11-dihydro-12-α-hydroxysteroid.

In some embodiments, the alkylhydroperoxide is tert-butyl hydroperoxide. The co-oxidant may be one of those described herein.

In some embodiments, the 11-β-hydroxysteroid is prepared by reducing a corresponding 11-ketosteroid with at least a stoichiometric amount of a reducing agent to provide the 11-β-hydroxysteroid.

In some embodiments, the 11-β-hydroxysteroid is hydrocortisone or a hydrocortisone derivative, such as a protected hydrocortisone.

It is to be understood that individual steps in the processes described herein can be done sequentially as described but are not necessarily performed sequentially. One or more of the steps can be performed as part of a larger scheme. One skilled in the art can readily react other parts of the compounds described herein to make analogues of these compounds.

C. Synthesis of Compound 24 from Compound 25

In another embodiment, this invention provides a method of preparing compound 24

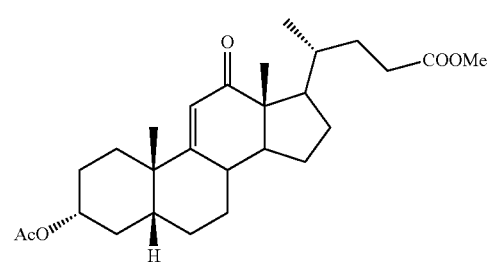

said method comprising:

a) contacting compound 25:

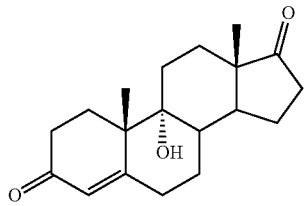

under hydrogenation conditions comprising hydrogen and at least 8% by weight of a 50% wet Pd on carbon in a solvent selected from the group consisting of acetone, isopropanol, ethyl acetate, N,N-dimethylformamide, and tetrahydrofuran in an autoclave maintained at elevated pressure to provide compound 26:

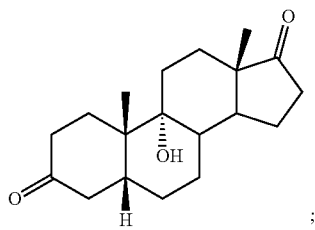

b) dehydration of compound 26 in the presence of sulfuric acid under conditions wherein water is eliminated to provide compound 27:

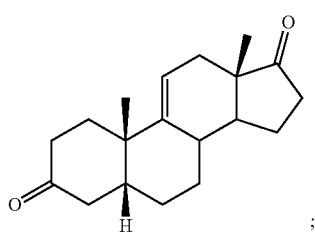

c) contacting compound 27 with an excess of lithium tri-t-butoxyaluminum hydride under selective reducing conditions including a temperature of from −40 to −45° C. to provide compound 28:

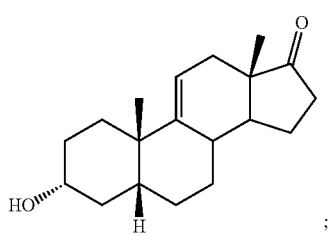

d) contacting compound 28 with an excess of ethyltriarylphosphonium halide under Wittig reaction conditions to provide compound 29:

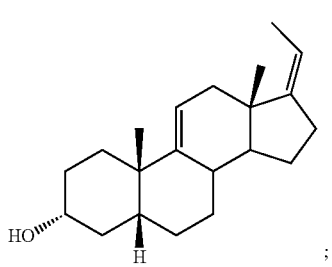

e) protecting the 3-α-hydroxy group of compound 29 under acetylation conditions including an excess of anhydrous acetic anhydride to provide compound 30:

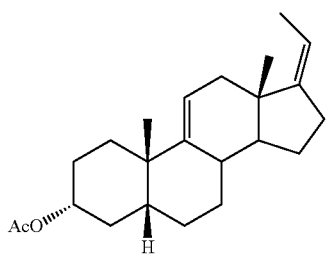

f) contacting compound 30 with an excess of methyl acrylate in presence of an excess of $C_1$-$C_2$ alkyl aluminum dichloride under alkylating conditions to form compound 31:

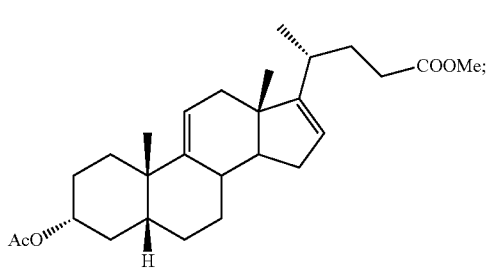

g) contacting compound 31 with hydrogen and a hydrogenation catalyst selected from platinum and dry palladium on carbon in an inert solvent under hydrogenation conditions including an autoclave maintained at an elevated pressure to provide compound 32;

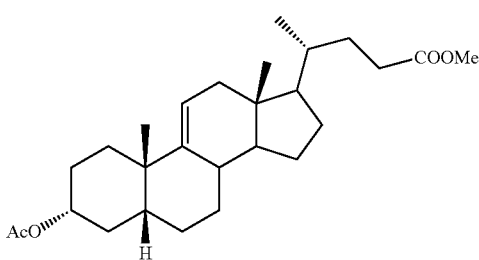

32 h) contacting compound 32 dissolved in an inert solvent under co-oxidizing conditions including an excess of $C_4$-$C_6$ t-alkyl hydroperoxide as a first oxidant and an excess of NaOCl as a co-oxidant under oxidizing conditions optionally followed by further oxidation with a slight excess of pyridiniumchlorochromate to provide compound 24:

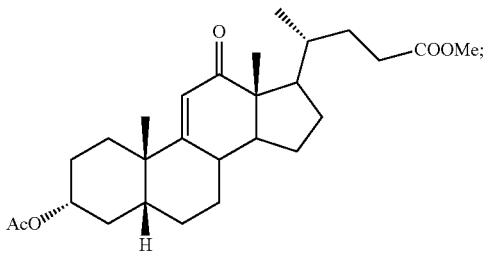

24 which compound is washed with methanol.

In an alternative embodiment, this invention provides a method of preparing compound 31

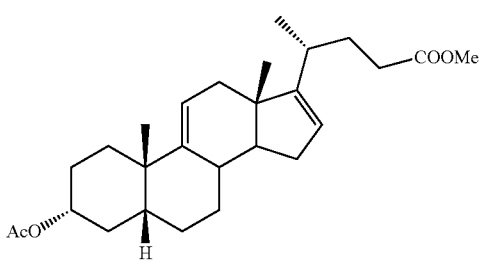

31 by contacting compound 30

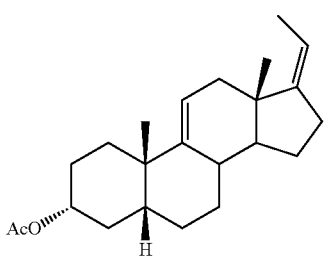

30 with methyl acrylate in presence of a Lewis acid.

In another embodiment, the Lewis acid is $EtAlCl_2$.

In another embodiment, this invention provides a method of preparing compound 26

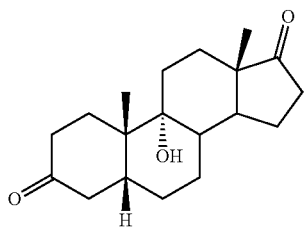

26 by contacting compound 25:

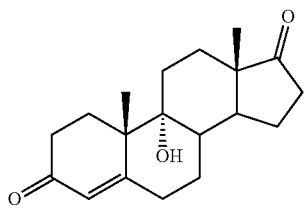

25 under hydrogenation conditions comprising hydrogen and 10% Pd/C wherein hydrogenation occurs in presence of N,N-dimethylformamide or acetone.

In another embodiment, hydrogenation occurs in presence of acetone.

In another embodiment, this invention provides a method for preparing compound 24 which method comprises:

a) contacting compound 25:

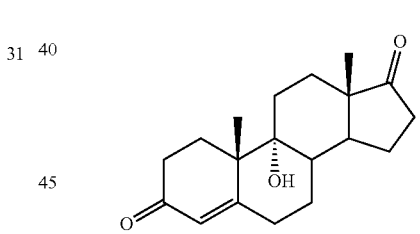

25 under hydrogenation conditions comprising hydrogen and at least 8% by weight of a 50% wet Pd on carbon in a solvent selected from the group consisting of acetone, isopropanol, ethyl acetate, N,N-dimethylformamide, and tetrahydrofuran in an autoclave maintained at elevated pressure to provide compound 26:

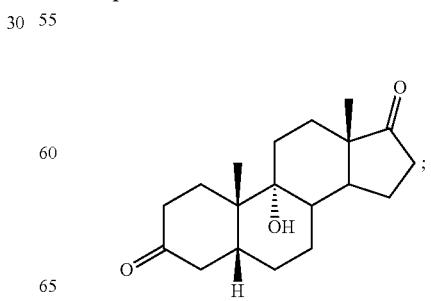

26

;

b) dehydration of compound 26 in the presence of sulfuric acid under conditions wherein water is eliminated to provide compound 27:

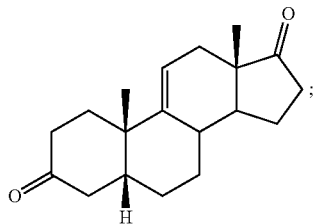

27 c) contacting compound 27 with an excess of lithium tri-t-butoxyaluminum hydride under selective reducing conditions including a temperature of from −40° C. to −45° C. to provide compound 28:

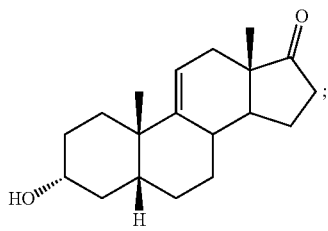

28 d) contacting compound 28 with an excess of ethyltri-arylphosphonium halide under Wittig reaction conditions to provide compound 29:

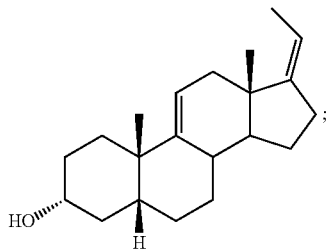

29 e) protecting the 3-α-hydroxy group of compound 29 under acetylation conditions including an excess of anhydrous acetic anhydride to provide compound 30:

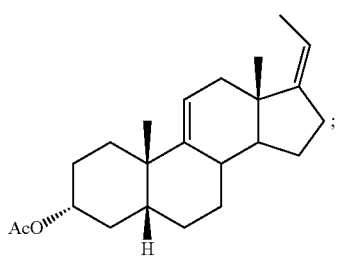

30 f) contacting compound 30 with an excess of methyl acrylate in presence of an excess of $C_1$-$C_2$ alkyl aluminum dichloride under alkylating conditions to form compound 31:

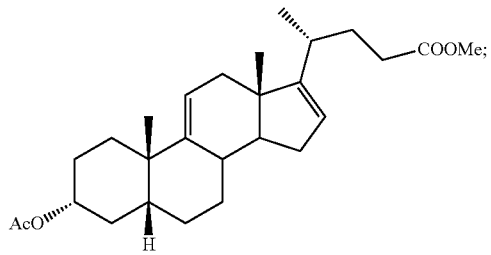

31 g) contacting compound 31 with hydrogen and a hydrogenation catalyst selected from the group consisting of: platinum and dry palladium on carbon; in an inert solvent under hydrogenation conditions including an autoclave maintained at an elevated pressure to provide compound 32;

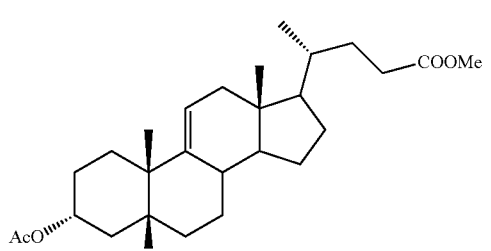

32 h) contacting compound 32 dissolved in an inert solvent under co-oxidizing conditions including an excess of $C_4$-$C_6$ t-alkyl hydroperoxide as a first oxidant and an excess of NaOCl as a co-oxidant under oxidizing conditions optionally followed by further oxidation with a slight excess of pyridiniumchlorochromate to provide compound 24:

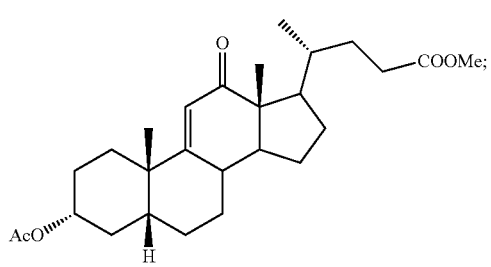

24 and
i) optionally, washing compound 24 with methanol.
In a further embodiment,
step a) comprises acetone as a solvent;
step b) comprises dichloromethane as a solvent;
step c) comprises anhydrous tetrahydrofuran as a solvent in an inert atmosphere;
Wittig reaction conditions of step d) comprise potassium tert-butoxide in anhydrous tetrahydrofuran as a solvent in an inert atmosphere;

step e) comprises triethylamine and 4-dimethylaminopyridine;

$C_1$-$C_2$ alkyl aluminum dichloride of step f) comprises ethylaluminum dichloride in anhydrous dichloromethane as a solvent in an inert atmosphere at 0-5° C.;

the hydrogenation catalyst of step g) comprises dry palladium on carbon in ethyl acetate as a solvent; and the $C_4$-$C_6$ t-alkyl hydroperoxide of step h) comprises t-butyl hydroperoxide in water as a solvent at a temperature below 5° C.

In another embodiment, this invention provides a method for preparing deoxycholic acid or a salt thereof which method comprising:

a) contacting compound 24

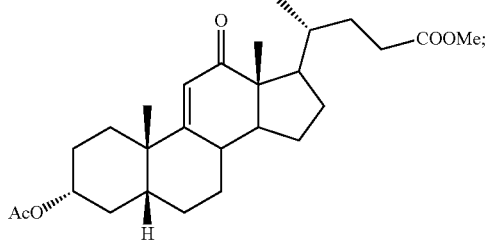

with hydrogen and Pd/C under hydrogenation conditions comprising hydrogen and Pd on carbon optionally followed by oxidizing any of the 12-hydroxyl groups formed during hydrogenation with pyridiniumchlorochromate under oxidizing conditions to provide compound 33;

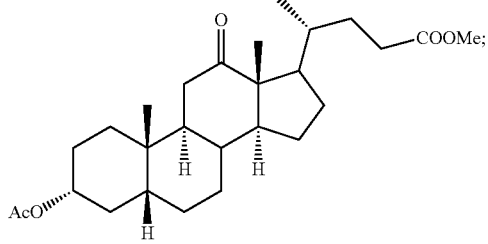

b) reacting compound 33 with lithium tri-t-alkoxyaluminum hydride under reducing conditions to provide compound 34:

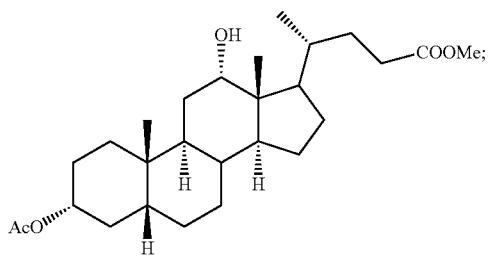

and
c) exposing compound 34 to deprotection and hydrolysis conditions to form deoxycholic acid or the salt thereof.

Compounds

In another aspect, this invention is directed to a compound of formula 1 or 5:

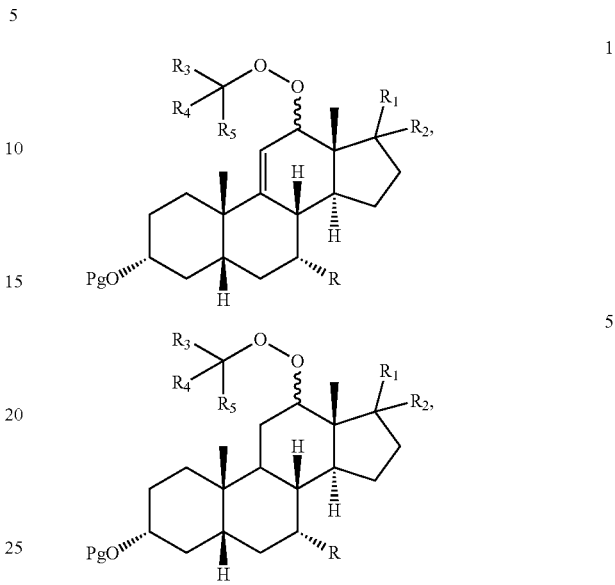

wherein

Pg is a hydroxyl protecting group;

R is hydrogen, hydroxyl, or —OPg;

$R^1$ is the 17-side chain of a bile acid selected from the group consisting of cholic acid, deoxycholic acid, taurocholic acid, wherein the carboxyl functionality of said side chain is optionally esterified with a $C_1$-$C_6$ alkyl or benzyl group, and glycocholic acid and $R^2$ is hydrogen, or $R^1$ and $R^2$ together with the carbon atom attached thereto form a keto or a keto protecting group; and each of $R^3$, $R^4$ and $R^5$ is independently $C_1$-$C_3$ alkyl.

In some embodiments, $R^1$ is selected from the group consisting of

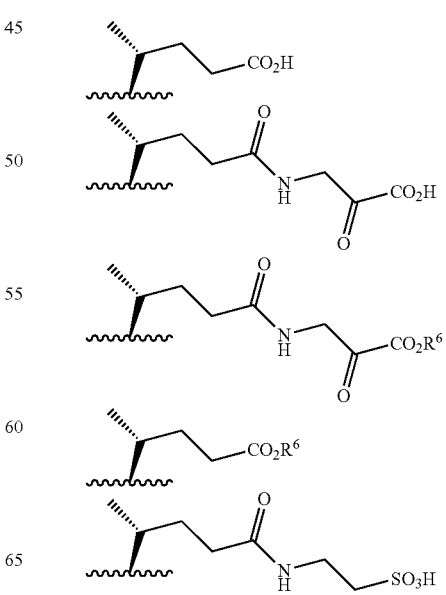

47

-continued

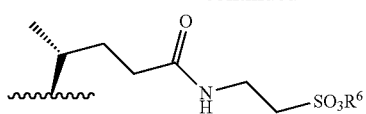

wherein $R^6$ is lower alkyl and the wavy line ⌇ represents the point of connection to the 17-position of steroidal scaffold.

In some embodiments, $R^1$ is the 17-side chain of a bile acid selected from the group consisting of cholic acid, deoxycholic acid, taurocholic acid, and glycocholic acid. In some embodiments, the carboxyl functionality of said side chain is optionally esterified with a $C_1$-$C_6$ alkyl group, such as a methyl, ethyl, or tert-butyl.

In some embodiments, $R^1$ and $R^2$ together with the carbon atom attached thereto form a keto group.

In some embodiments, $R^1$ and $R^2$ together with the carbon atom attached thereto form a keto protecting group, such as:

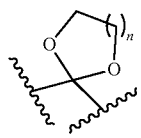

wherein n is 1, 2, or 3 and the wavy line ⌇ represents the point of connection to the rest of the molecule.

In some embodiments, the compound of formula 1 is compound 41:

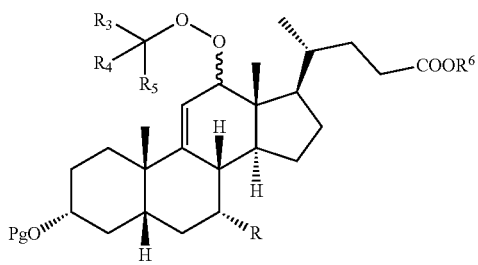

41

In some embodiments, the compound of formula 1 is selected from the group consisting of compound 42, 43, 44, 45 or 46:

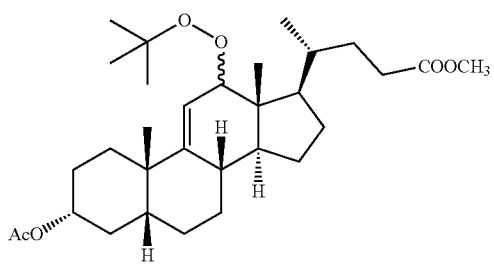

42

48

-continued

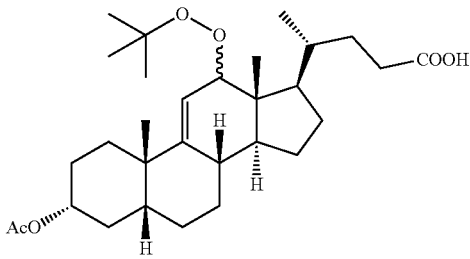

43

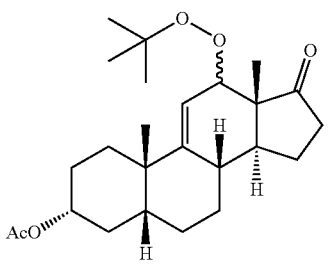

44

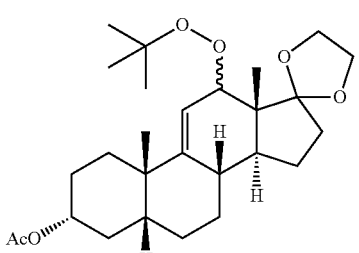

45

, and

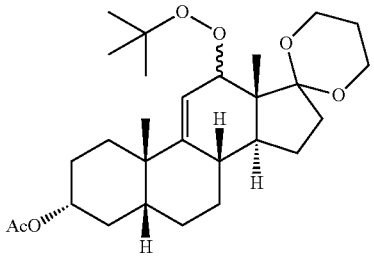

46

In some embodiments, the compound of formula 5 is compound 47:

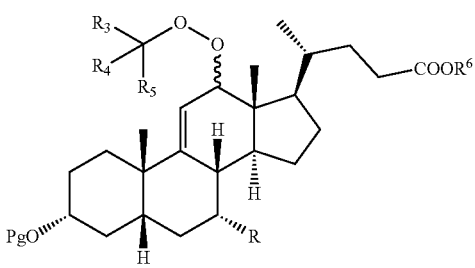

47

In some embodiments, the compound of formula 5 is selected from the group consisting of compound 48, 49, 50, 51 or 52:

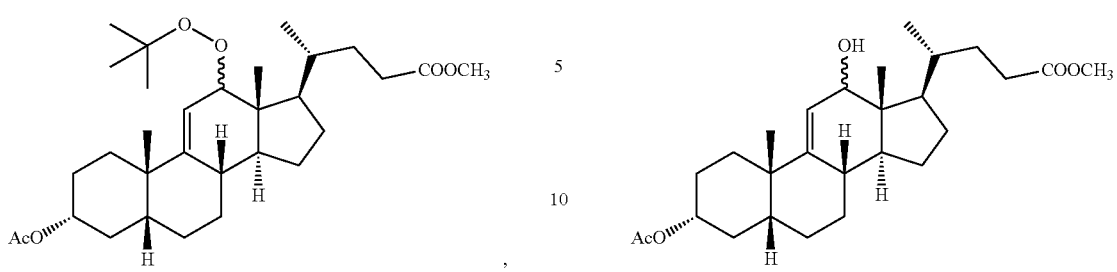
48
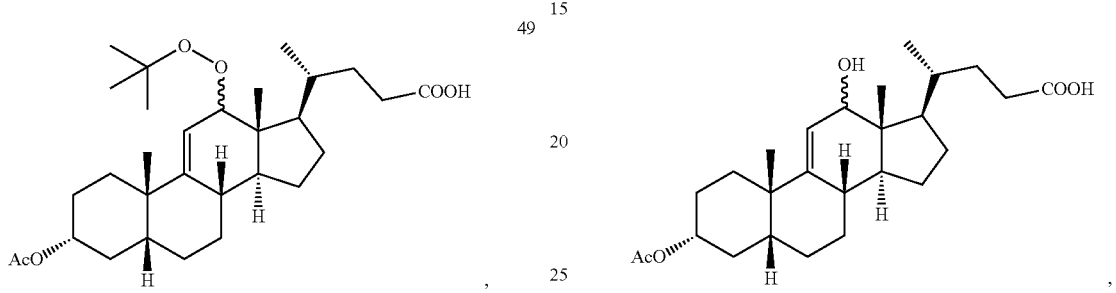
49
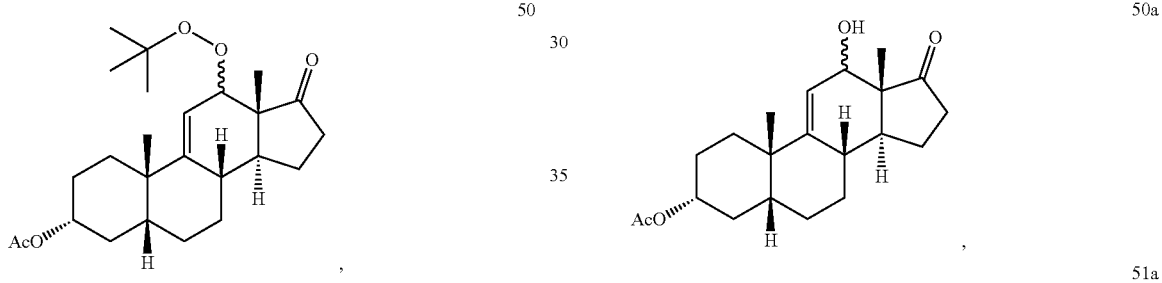
50
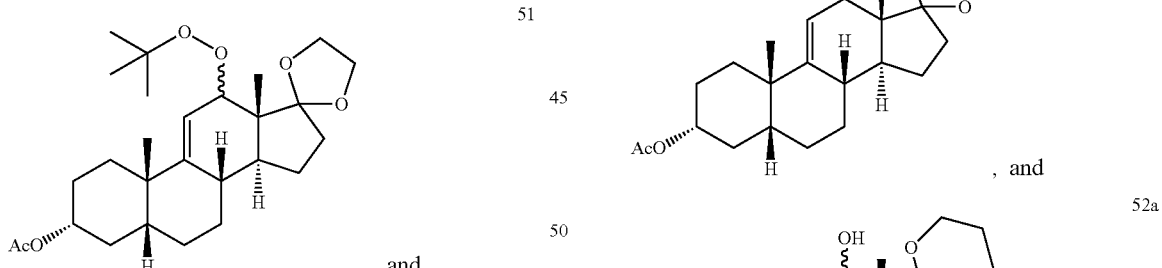
51
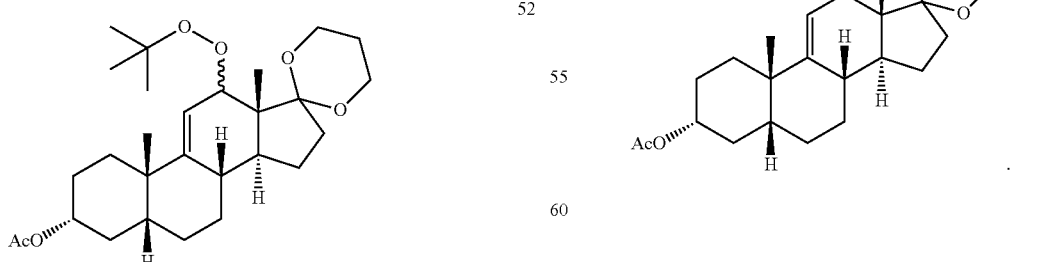
52
, and
, and
48a
49a
50a
51a
52a
D. Synthesis of DCA from Compound 53
In some embodiments, the compound of formula 6 is selected from the group consisting of compound 48a, 49a, 50a, 51a or 52a:
In another embodiment, provided is a method for preparing deoxycholic acid (DCA) or a pharmaceutically acceptable salt thereof, said method comprises:

(1) reacting a compound of formula 53

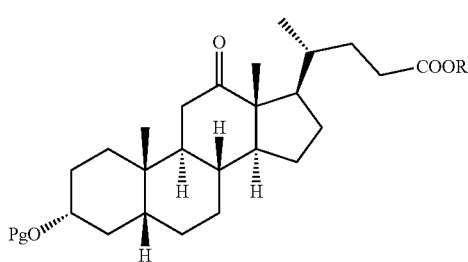

with a reducing agent to form a compound of formula 54 wherein Pg is a protecting group and R is alkyl

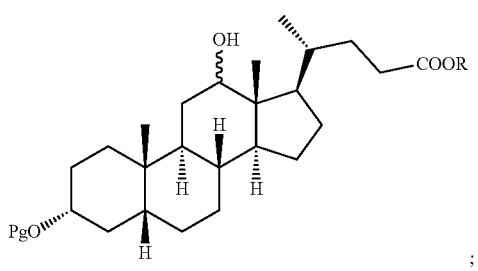

and (2) exposing the compound of formula 54 to deprotection and hydrolysis conditions to form deoxycholic acid or the pharmaceutically acceptable salt thereof.

In some embodiments, Pg is —C(O)R$^1$, wherein R$^1$ is lower alkyl. In some embodiments, Pg is —C(O)CH$_3$. In some embodiments, the hydrolysis conditions comprise an alkali metal hydroxide, alkali metal alkoxide or a mixture thereof. In some embodiments, the alkali metal hydroxide is LiOH or NaOH.

In some embodiments, the compound of formula 53 is a compound of formula 33, which is methyl 3α-acetoxy-5β-cholan-12-one-24-oate:

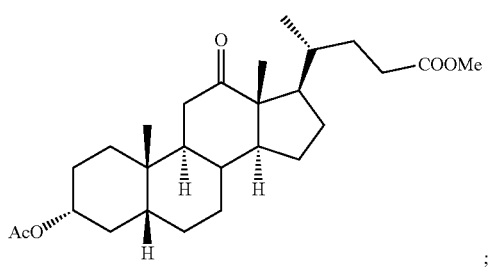

and the compound of formula 54 is a compound of formula 34, which is methyl 3α-acetoxy-12α-hydroxy-5β-cholan-24-oate:

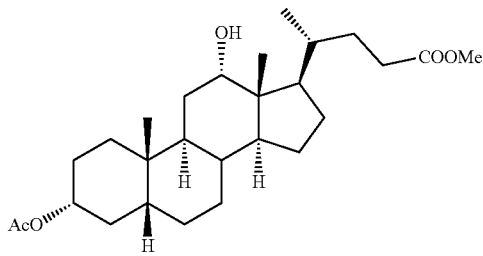

In some embodiments, this invention provides a method for preparing a compound of formula 26, which is 9α-hydroxy-5β-androstan-3,17-dione:

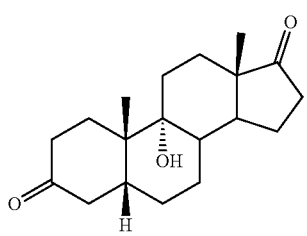

which method comprises reacting 9α-hydroxyandrost-4-en-3,17-dione 120

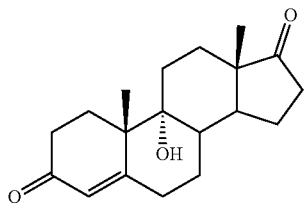

with H$_2$ under hydrogenation conditions to form 9α-hydroxy-5β-androstan-3,17-dione.

In some embodiments, the hydrogenation conditions comprise a solvent which solvent is DMF, acetone, ethyl acetate, and the like.

In some embodiments, this invention provides a method for preparing a compound of formula 27, which is 5β-androst-9(11)-en-3,17-dione:

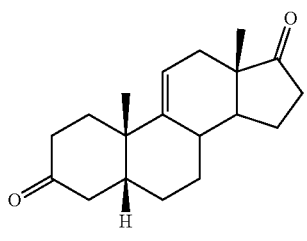

which method comprises reacting a compound of formula 26

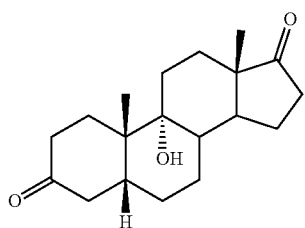

26 with an acid to form the compound of formula 27.

In some embodiments, this invention provides a method for preparing a compound of formula 29, which is (Z)-3α-hydroxy-5β-pregna-9(11),17(20-diene:

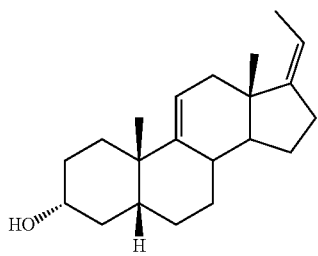

29 and the method comprises reacting a compound of formula 28

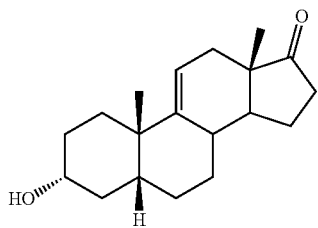

28 with a two-carbon olefination reagent under olefin forming conditions to form (Z)-3α-hydroxy-5β-pregna-9(11),17(20)-diene.

In some embodiments, the compound of formula 28 is prepared by reacting a compound of formula 27

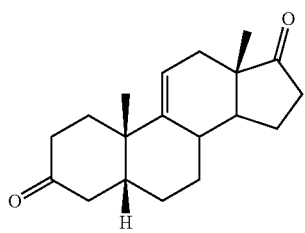

27 with a reducing agent to form the compound of formula 28.

In some embodiments, this invention provides a method for preparing a compound of formula 18:

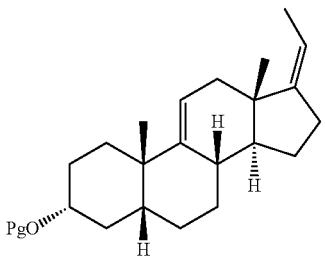

18 comprising converting a compound of formula 29

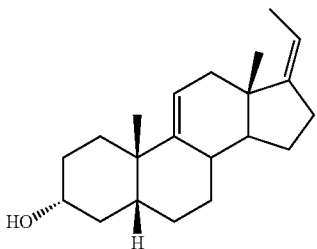

29 to the compound of formula 18 wherein Pg is a protecting group.

In some embodiments, Pg is —C(O)R$^1$, wherein R$^1$ is lower alkyl. In some embodiments, Pg is —C(O)CH$_3$.

In some embodiments, the compound of formula 18 is a compound of formula 30, which is (Z)-3α-acetoxy-5β-pregna-9(11), 17(20)-diene:

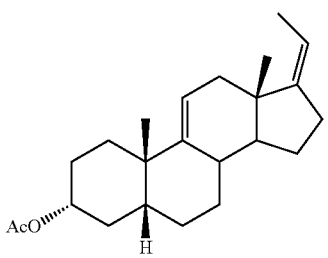

30 wherein the method comprises exposing the compound of formula 55 to acylation conditions to form (Z)-3α-acetoxy-5β-pregna-9(11),17(20)-diene.

In some embodiments, this invention provides a method for preparing a compound of formula 19:

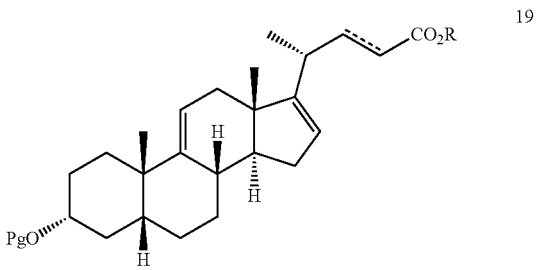

19 wherein R is alkyl, Pg is a protecting group, and the dashed line ═ is a single or double bond, which method comprises reacting a compound of formula 18

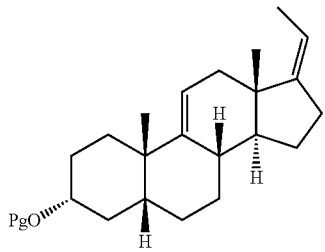

with an alkylpropiolate CH≡CC(O)OR or an alkyl acrylate CH$_2$═CHC(O)OR in the presence of a Lewis acid to form the compound of formula 19.

In some embodiments, Pg is —C(O)R$^1$, wherein R$^1$ is lower alkyl. In some embodiments, Pg is —C(O)CH$_3$. In some embodiments, Pg is CH$_3$C(O) and R is CH$_3$.

In some embodiments, the compound of formula 19 is a compound of formula 31 which is methyl 3α-acetoxy-5β-chol-9(11), 16-dien-24-oate:

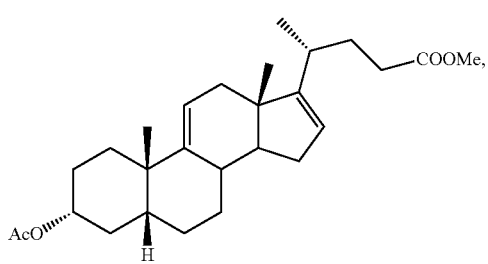

and wherein the method comprises reacting a compound of formula 30

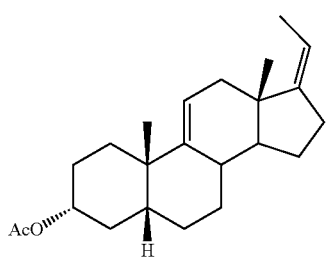

with CH$_2$CHC(O)OCH$_3$ in the presence of the Lewis acid to form methyl 3α-acetoxy-5β-chol-9(11), 16-dien-24-oate.

In some embodiments, this invention provides a method for preparing a compound of formula 21:

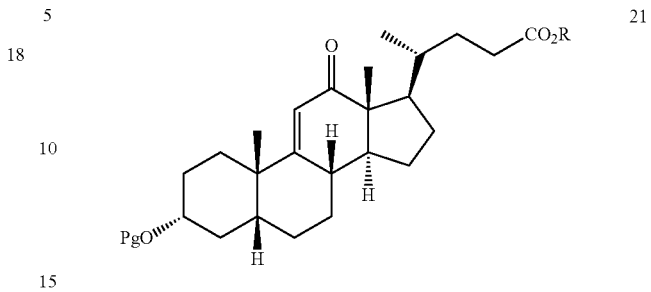

wherein Pg is a protecting group and R is alkyl, which method comprises reacting the compound of formula 20

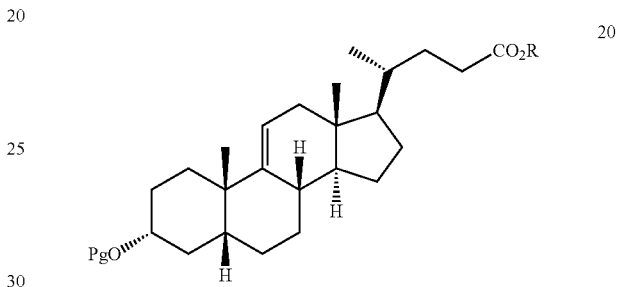

with an oxidizing agent to form the compound of formula 21.

In some embodiments, the compound of formula 20 is prepared by reacting a compound of formula 19

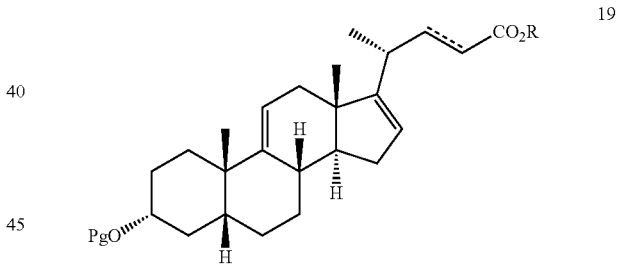

with H$_2$ under hydrogenation conditions to form the compound of formula 20, wherein the dashed line ═ is a single or double bond.

In some embodiments, the compound of formula 21 is a compound of formula 24, which is methyl 3α-acetoxy-5β-chol-9(11)-en-12-one-24-oate:

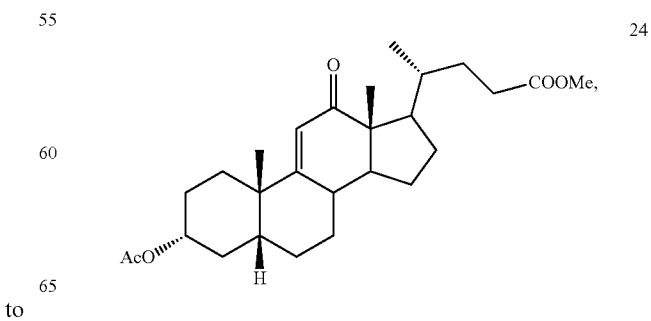

and the method comprises reacting a compound of formula 56

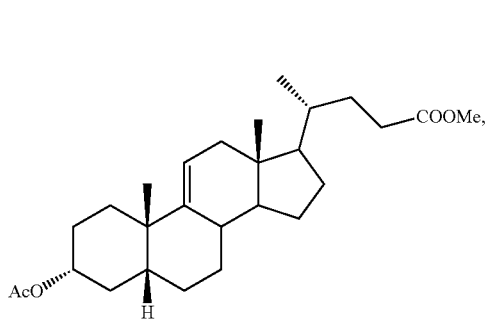

with an oxidizing agent to form the compound of formula 24.

In some embodiments, this invention provides a method for preparing a compound of formula 53:

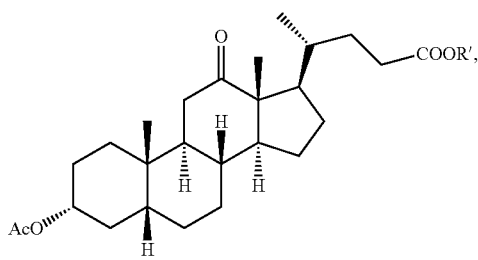

wherein Pg is a protecting group and R is alkyl, which method comprises reacting a compound of formula 57

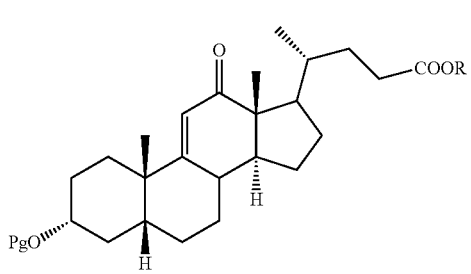

with $H_2$ under hydrogenation conditions to form the compound of formula 53.

In some embodiments, Pg is —C(O)R$^1$, wherein R$^1$ is lower alkyl. In some embodiments, Pg is —C(O)CH$_3$.

In some embodiments, the compound of formula 53 is a compound of formula 33, which is methyl 3α-acetoxy-5β-cholan-12-one-24-oate:

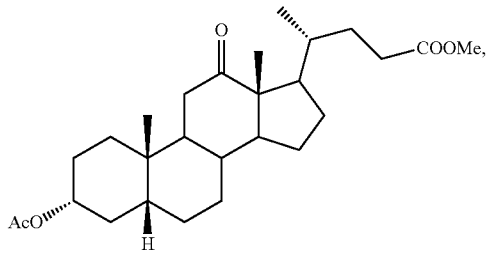

and the method comprises reacting a compound of formula 58

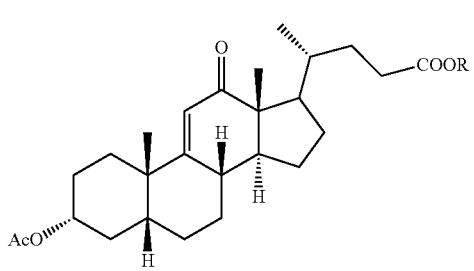

with $H_2$ under hydrogenation conditions to form methyl 3α-acetoxy-5β-cholan-12-one-24-oate.

In some embodiments, the method comprises (a) reacting a compound of formula 21

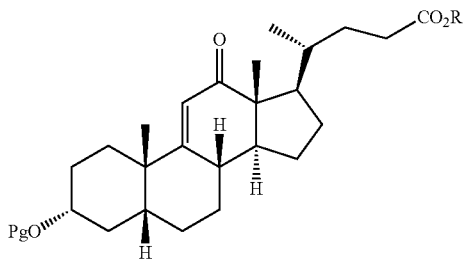

with $H_2$ under hydrogenation conditions to form a mixture of the compound of formula 53 and a compound of formula 59:

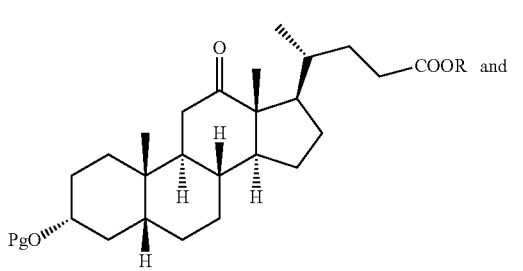

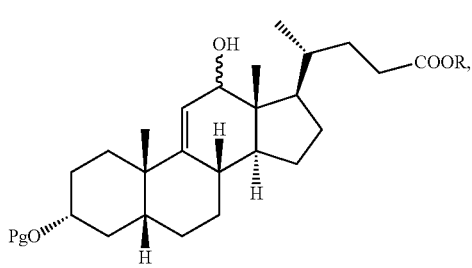

(b) contacting the mixture of the compound of formula 53 and the compound of formula 59 with an oxidizing reagent under conditions to form a mixture of the compound of formula 57 and the compound formula 53, and (c) contacting the mixture of the compound of formula 57 and the compound of formula 53 with H$_2$ under hydrogenation conditions to form the compound of formula 53.

In some embodiment, the oxidizing agent is pyridinium chlorochromate.

The compounds of preferred embodiments can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts, *Protecting Groups in Organic Synthesis*, Third Edition, Wiley, New York, 1999, and references cited therein.

The starting materials and reagents for the reactions described herein are generally known compounds or can be prepared by known procedures or obvious modifications thereof. For example, many of the starting materials and reagents are available from commercial suppliers such as Aldrich Chemical Co. (Milwaukee, Wis., USA), Bachem (Torrance, Calif., USA), Emka-Chem or Sigma (St. Louis, Mo., USA). Others may be prepared by procedures, or obvious modifications thereof, described in standard reference texts such as Fieser and Fieser's *Reagents for Organic Synthesis*, Volumes 1-15 (John Wiley and Sons, 1991), Rodd's *Chemistry of Carbon Compounds*, Volumes 1-5 and Supplementals (Elsevier Science Publishers, 1989), *Organic Reactions*, Volumes 1-40 (John Wiley and Sons, 1991), March's *Advanced Organic Chemistry*, (John Wiley and Sons, 4$^{th}$ Edition), and Larock's *Comprehensive Organic Transformations* (VCH Publishers Inc., 1989). For example, hydrocortisone can be prepared from cortisone using conventional reduction techniques.

The various starting materials, intermediates, and compounds of the preferred embodiments may be isolated and purified where appropriate using conventional techniques such as precipitation, filtration, crystallization, evaporation, distillation, and chromatography. Characterization of these compounds may be performed using conventional methods such as by melting point, mass spectrum, nuclear magnetic resonance, and various other spectroscopic analyses.

Methodology

The purification methods of this invention employ deoxycholic acid (DCA) having a purity of about 95% or less and, in some cases, a purity of about 80% or less. These methods enhance the purity of these DCA compositions to at least about 96% or at least 99%.

In one aspect, this invention provides for a method for purifying deoxycholic acid (DCA) to provide DCA having a purity of greater than 96% or at least 99%. In one embodiment, the method comprises:

(a) contacting DCA having a purity of about 95% or less with a solvent comprising dichloromethane under conditions to form a DCA solution;

(b) crystallizing the DCA from the DCA solution obtained from step (a) to provide a solution containing crystalline DCA;

(c) recovering the crystalline DCA and removing sufficient amounts of the dichloromethane to provide a purity of greater than 96% for the recovered crystalline DCA.

In some embodiments, this invention provides for a method for purifying deoxycholic acid (DCA) to provide DCA having a purity of greater than 96% or at least 99%. In one embodiment, the method comprises:

(a) contacting DCA having a purity of about 95% or less with a solvent comprising dichloromethane and methanol under conditions to form a DCA solution;

(b) crystallizing the DCA from the DCA solution obtained from step (a) to provide a solution containing crystalline DCA;

(c) recovering the crystalline DCA and removing sufficient amounts of the dichloromethane to provide a purity of greater than 96% for the recovered crystalline DCA.

In some embodiments, either of the above process is repeated.

In one embodiment, DCA having a purity of about 95% or less is dissolved in a mixture of dichloromethane and methanol. If necessary, dissolution can be facilitated by heating the solvent to reflux. Furthermore, as necessary, any insoluble impurities can be removed by filtration typically filtering the solution at an elevated temperature, for example, using a filter having a pore size of about 5 μm or less.

The amount of dichloromethane and methanol initially employed in the solvent systems of the methods of this invention is best defined by a weight ratio of dichloromethane to methanol of from about 100:1 to about 3:1, or from about 50:1 to about 4:1, or from about 20:1 to 10:1.

The amount of DCA employed relative to the total amount of solvent initially employed is best defined by a ratio of solvent to DCA of from about 40:1 to about 10:1, or about 30:1 to about 15:1 or about 19:1.

In another embodiment, additional dichloromethane is added at the reflux temperature. The amount of additional dichloromethane ranges from about 20 to 100 volume percent of the initial amount of dichloromethane incorporated into the solvent system. In some embodiments, the amount of additional dichloromethane is from about 30-70 volume percent or about 50 volume percent of the initial amount of dichloromethane used.

Upon dissolution and optional filtration, substantially all of the methanol is then removed by azeotropic distillation at atmospheric pressure leaving a solution comprising primarily dichloromethane. Crystallization of the DCA from the dichloromethane provides for DCA having a purity of at least 96% or at least 99%.

In one embodiment, the DCA is derived from mammalian sources, which is generally commercially available.

In another embodiment, the DCA is derived synthetically. Methods for preparing synthetic DCA are described herein and in U.S. patent application Ser. No. 12/035,339, published as US 2008-0318870 A1, and U.S. patent application Ser. No. 12/153,446, published as US 2009-0270642 A1, which are hereby incorporated by reference in its entirety.

Compositions

In one of its composition aspects, this invention provides a compound that is synthetic deoxycholic acid (DCA) or a pharmaceutically acceptable salt thereof, wherein the synthetic DCA or the pharmaceutically acceptable salt thereof has a purity of at least 99%.

In another of its composition aspects, this invention provides for a solution comprising DCA and a solvent which comprises dichloromethane and methanol wherein the concentration of solvent to DCA is from 40:1 to about 10:1 and further wherein the ratio of dichloromethane to methanol is from about 100:1 to about 3:1.

The invention also provides a composition comprising a DCA having a purity of at least 99% or a pharmaceutically acceptable salt thereof and an acceptable excipient. The invention also provides a composition consisting essentially of a DCA having a purity of at least 99% or a pharmaceutically acceptable salt thereof wherein DCA is essentially the sole fat removal component of said composition.

The compositions can be comprised of the DCA of this invention in combination with at least one acceptable excipient or pharmaceutically acceptable excipient. Such excipient may be any solid, liquid, semi-solid or, in the case of an aerosol composition, gaseous excipient that is generally available to one of skill in the art.

Solid excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, vegetable or synthetic origin, e.g., peanut oil, soybean oil, mineral oil, sesame oil, etc. Examples of liquid carriers, particularly for injectable solutions, include water, saline, aqueous dextrose, and glycols.

The DCA in the compositions can be at a concentration of about 0.001 to 10, 0.01 to 5, or 0.1 to 2% w/w, w/v, or v/v. In some embodiments, the DCA can be at a concentration of about 0.1-5% w/w or about 1% w/w. In some embodiments, the fat dissolving solution comprises up to 100, 50, 20, 10, 5, 2, 1, 0.5, 0.2, 0.05, 0.02, or 0.01 grams of the one or more detergents, bile acids and/or bile salts, deoxycholic acid or salts thereof or sodium deoxycholate.

In some embodiments, the compositions herein include no lipids, phospholipids, or phosphatidylcholine. In some embodiments, the compositions herein include up to 5% w/w, w/v, or v/v lipids, phospholipids, or phosphatidylcholine.

In some embodiments, the compositions can further comprise a second therapeutic agent selected from the group consisting of: anti-microbial agents, vasoconstrictors, anti-thrombotic agents, anti-coagulation agents, suds-depressants, anti-inflammatory agents, analgesics, dispersion agents, anti-dispersion agents, penetration enhancers, steroids, tranquilizers, muscle relaxants, and anti-diarrhea agents. In some embodiments, a solution is in a container that contains up to 500 mL of solution. Such container can be a syringe or syringe-loadable container.

Methods of Use

The DCA of this invention preferably with at least 99% purity or a pharmaceutically acceptable salt or compositions thereof are useful in various pharmaceutical or cosmetic applications, form example as described in U.S. Pat. No. 7,622,130, and U.S. Patent Application Nos. 2005-0267080 A1 and 2006-0127468 A1, which are incorporated herein by reference in their entirety.

In one embodiment, the present invention relates to methods for reducing a subcutaneous fat deposit in a subject. Such methods comprise the step of administering locally to a subcutaneous fat deposit in the subject a composition comprising: (i) a fat-dissolving effective amount of deoxycholic acid preferably having a purity of at least 99% or a salt thereof, for example, sodium deoxycholate; (ii) a pharmaceutical, veterinary, or cosmetic excipient; and wherein the DCA or salt thereof is essentially the only fat removing component of the composition. In some embodiments, the fat deposit is cosmetically unappealing and the removal of it is to improve the appearance of the subject. In some embodiments, the fat deposit is associated with a condition selected from the group consisting of obesity, fat redistribution syndrome, eyelid fat herniation, lipomas, Dercum's disease, lipodystrophy, buffalo hump lipodystrophy, dorsocervical fat, visceral adiposity, breast enlargement, hyperadiposity, diffused body fat around trunk and arms, and fat deposits associated with cellulite. In some embodiments, the above method does not include performing surgery on said subject.

The foregoing and other aspects of the embodiments disclosed herein may be better understood in connection with the following examples.

EXAMPLES

In the examples below and elsewhere in the specification, the following abbreviations have the indicated meanings. If an abbreviation is not defined, it has its generally accepted meaning.

| | |
|---|---|
| Ac$_2$O | Acetic anhydride |
| ACN | Acetonitrile |
| AcOH | Acetic acid |
| CAD | Charged aerosol detector |
| CONC | Concentrated |
| CrO$_3$ | Chromium trioxide |
| DCA | Deoxycholic acid |
| DCM (CH$_2$Cl$_2$) | Dichloromethane |
| DMAP | 4-Dimethylaminopyridine |
| DMF | N,N-Dimethylformamide |
| EtAlCl$_2$ | Ethyl aluminum dichloride |
| EtOAc | Ethyl acetate |
| H or h | Hour |
| H$_2$SO$_4$ | Sulphuric acid |
| HCl | Hydrochloric acid |
| HClO$_4$ | Perchloric acid |
| HPLC | High pressure liquid chromatography |
| HPLC-RI | High pressure liquid chromatography with refractive index detection |
| Hz | Hertz |
| KBr | Potassium bromide |
| K-O$^t$Bu | Potassium tert-butoxide |
| LiAl(O$^t$Bu)$_3$H | Lithium tri-tert-butoxyaluminum hydride |
| LiOH | Lithium hydroxide |
| LOD | Loss on drying |

| | |
|---|---|
| MeOH | Methanol |
| MHz | Megahertz |
| Min | Minutes |
| mL | Milliliter |
| Mmol | Millimole |
| Mol | Mole |
| MTBE | Methyl tert-butyl ether |
| $Na_2SO_4$ | Sodium sulfate |
| NaOH | Sodium hydroxide |
| NMT | Not more than |
| Obs | Observed |
| PCC | Pyridinium chlorochromate |
| Pd/C | Palladium on carbon |
| $PtO_2$ | Platinum oxide |
| Rep | Reported |
| TEA | Triethylamine |
| TFA | Trifluoroacetic acid |
| THF | Tetrahydrofuran |
| TLC | Thin layer chromatography |
| UV | Ultraviolent |
| Wt | Weight |

General:

All manipulations of oxygen- and moisture-sensitive materials were conducted with standard two-necked flame dried flasks under an argon or nitrogen atmosphere. Column chromatography was performed using silica gel (60-120 mesh). Analytical thin layer chromatography (TLC) was performed on Merck Kiesinger 60 $F_{254}$ (0.25 mm) plates. Visualization of spots was either by UV light (254 nm) or by charring with a solution of sulfuric acid (5%) and p-anisaldehyde (3%) in ethanol.

Apparatus:

Proton and carbon-13 nuclear magnetic resonance spectra ($^1$H NMR and $^{13}$C NMR) were recorded on a Varian Mercury-Gemini 200 ($^1$H NMR, 200 MHz; $^{13}$C NMR, 50 MHz) or a Varian Mercury-Inova 500 ($^1$H NMR, 500 MHz; $^{13}$C NMR, 125 MHz) spectrometer with solvent resonances as the internal standards ($^1$H NMR, $CHCl_3$ at 7.26 ppm or DMSO at 2.5 ppm and DMSO-$H_2O$ at 3.33 ppm; $^{13}$C NMR, $CDCl_3$ at 77.0 ppm or DMSO at 39.5 ppm). $^1$H NMR data are reported as follows: chemical shift (δ, ppm), multiplicity (s=singlet, d=doublet, t=triplet, q=quartet, br=broad, m=multiplet), coupling constants (Hz), and integration. Infrared spectra (FT-IR) were run on a JASCO-460+ model. Mass spectra were obtained with a Perkin Elmer API-2000 spectrometer using ES+ mode. Melting points were determined using a LAB-INDIA melting point measuring apparatus and are uncorrected. HPLC chromatograms were recorded using a SHIMADZU-2010 model with a PDA detector. Specific optical rotations were determined employing a JASCO-1020 at 589 nm and are uncorrected.

Chemicals:

Unless otherwise noted, commercially available reagents were used without purification. Diethyl ether and THF were distilled from sodium/benzophenone. Laboratory grade anhydrous DMF, commercially available DCM, ethyl acetate and hexane were used.

Example 1

Synthesis of 3α-Acetoxy-5β-androstane-9,11-ene-17-one (36) from Hydrocortisone

Step 1

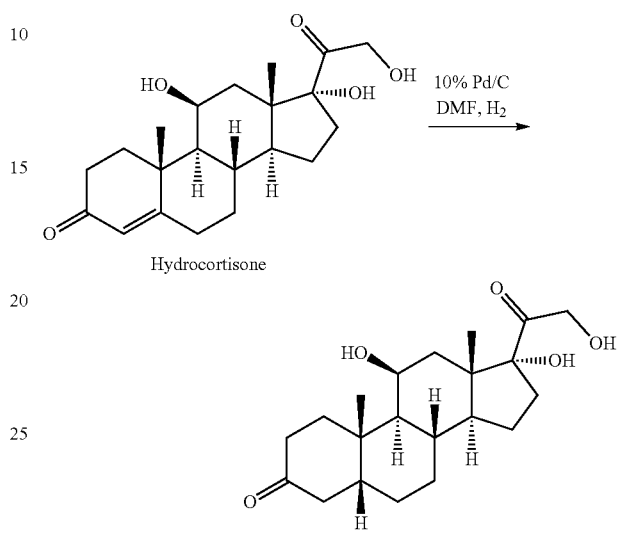

To a solution of hydrocortisone (25.0 g) in DMF (150 mL) was added 10% of Pd/C (1.5 g, 6-wt %) and the resulting slurry was hydrogenated in an autoclave (60 psi) for 6 h at 25-35° C. Upon complete disappearance of starting material, as evidenced by TLC (30% EtOAc in DCM), the crude reaction mixture was filtered through a CELITE® (diatomaceous earth) (8 g) bed and washed with DMF (100 mL). The solvent was completely removed by distillation under vacuum at below 65° C., which afforded compound 15 as a white solid (23.0 g, 91.5%).

Step 2

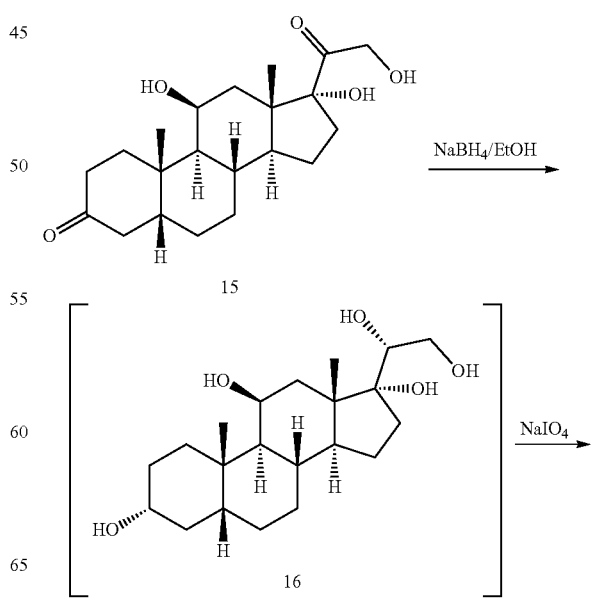

-continued

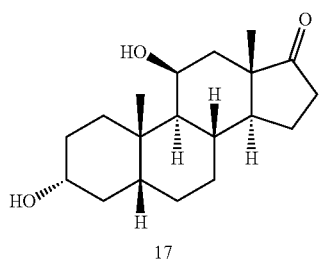
17

To a solution of compound 15 (23.0 g) in ethanol (350 mL) and DCM (350 mL) was added sodium borohydride (2.4 g), and the resulting solution was stirred for 3 h at 25-35° C. At this point, 50% aqueous acetone (200 mL) was added to quench the excess reagent and then sodium periodate (33.7 g) was added. The resulting solution was stirred for 16 h at 25-35° C. TLC showed complete disappearance of the intermediate (40% EtOAc in DCM). Water (400 mL) was added to the reaction mixture. The phases were separated and the aqueous layer was extracted with DCM (600 mL). The organic layers were combined and then washed with saturated brine solution (200 mL). The solvent was evaporated under vacuum to provide crude compound 16 as a white solid (23.0 g). The crude product was stirred in hexane (200 mL) at 30° C. for 1 h, filtered and washed with hexane (50 mL) to afford compound 16 as a white solid (19.0 g, 98%).

Step 3

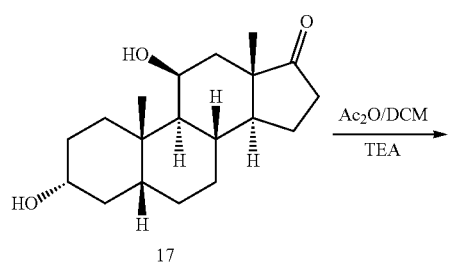
17 → Ac₂O/DCM, TEA

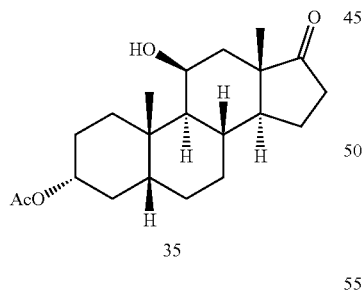
35

To a solution of compound 16 (19.3 g) in DCM (340 mL) was added triethylamine (12.7 g), DMAP (0.76 g) and acetic anhydride (12.9 g) at 25-35° C. After stirring for 2 hr at 25-35° C., TLC analysis (60% EtOAc in hexanes) showed the reaction to be complete. The reaction mixture was washed with saturated sodium bicarbonate solution (200 mL) followed by a second wash with brine solution (100 mL). The organic layer was dried over Na₂SO₄ (50 g) and filtered. The filtrate was concentrated by vacuum distillation to afford compound 35 as an off-white solid (18.0 g, 82%).

Step 4

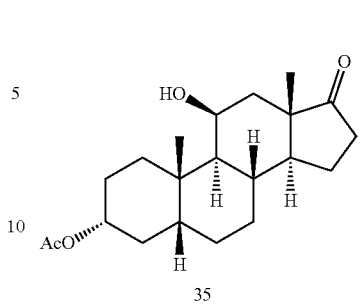
35 → SOCl₂/pyridine

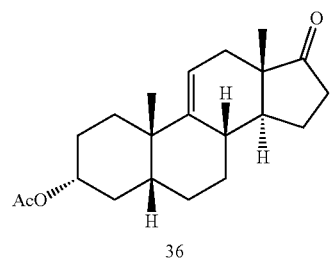
36

To a solution of compound 35 (18.0 g) in pyridine (100 mL) was added thionyl chloride (6.0 mL) at 25-35° C. and the resulting solution was stirred for 1 hr at 25-35° C. At this point the reaction was determined by TLC (30% EtOAc in hexanes) to be complete. Pyridine was removed by evaporation under vacuum at below 60° C. The crude material was dissolved in a mixture of water (100 mL) and ethyl acetate (180 mL) and the phases were separated. The aqueous phase was extracted with ethyl acetate (180 mL) and the organic phases were combined. The combined organic phase was washed with 2N HCl (100 mL) and saturated brine solution (100 mL). After drying over anhydrous Na₂SO₄ (40 g), the mixture was filtered and the filtrate was concentrated to dryness by vacuum distillation to provide compound 36 as a white solid (15.0 g, 88%).

Example 2

(Z)-3α-Acetoxy-5β-pregna-9(11), 17(20)-diene (30)

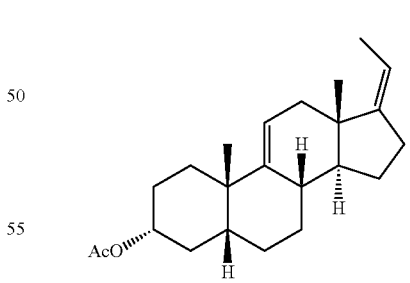
30

Compound 30 can be prepared by procedures similar to that described in Example 8, converting compound 28 to compound 30.

Methods and examples for preparing and purifying DCA from compound 60 are described in GB2452358 and U.S. Provisional Application 61/288,132, titled "METHODS FOR THE PURIFICATION OF DEOXYCHOLIC ACID", filed on Dec. 18, 2009, both of which are incorporated by reference hereby in their entirety.

Example 3
Impurities Isolated During the Preparation of DCA or Intermediates Thereof
The following compounds were recovered as impurities during the synthesis described herein:
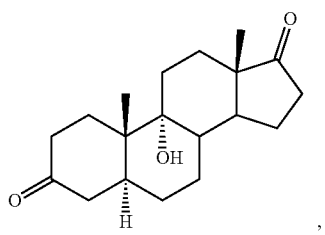
61
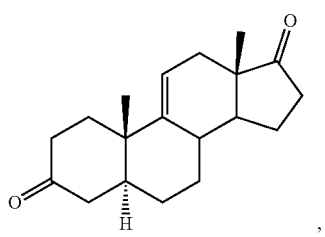
62
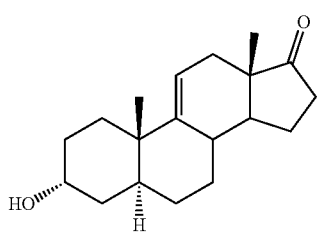
63
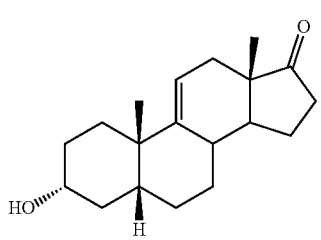
64
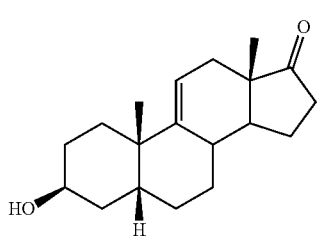
65
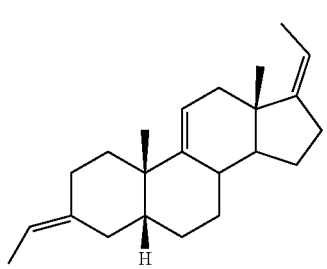
66
-continued
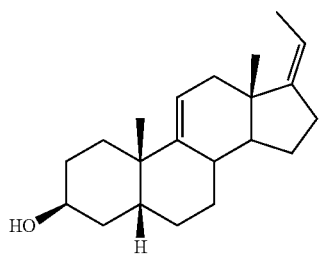
67
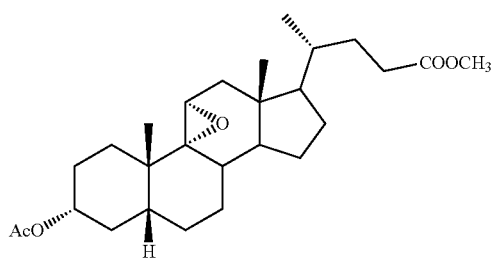
68
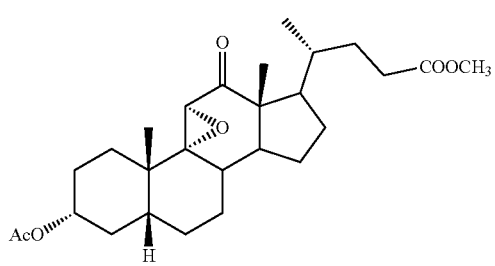
69
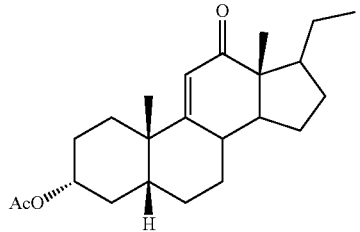
70
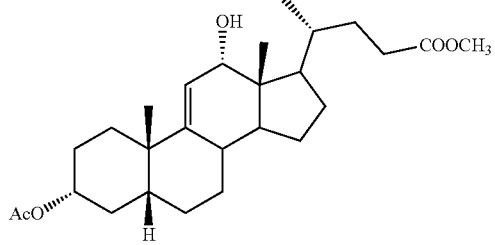
71
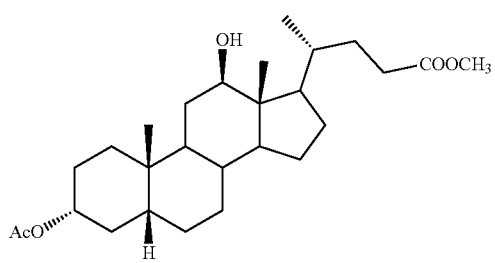
72

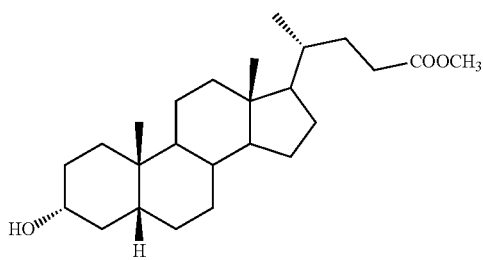

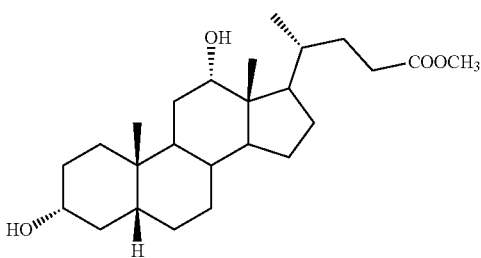

The compounds set forth above have utility as intermediates that can be recycled into a reaction scheme leading to compound 18. For example, compounds 61 and 62 and be dehydrogenated by conventional means to provide the 4,5-ene compound which can be rehydrogenated to provide the proper stereochemistry at 5-position.

The 17-keto group of compound 63 and 65 can be protected by conventional means such as ketal formation. The 3-hydroxyl group of both compounds 63 and 65 can then be oxidized to form the 3-keto group. For compound 63, dehydrogenation at the 4,5 position followed by hydrogenation will provide proper stereochemistry at the 5-position. For both compounds 63 and 65, reduction of the 3-keto group followed by deprotection of the 17-keto group provides for compound 18.

compound 64 can be selectively protected at the 3-hydroxyl group and the 17-hydroxyl group can then be oxidized followed by deprotection at the 3-hydroxyl to provide compound 18.

The 3,17 di-allyl compound 66 can be oxidized to provide the 3,17 di-keto compound which can be reduced by conventional means to provide the 3,17-dihydroxyl compound such as compound 64.

compound 67 can be oxidized at the 3-position and then reduced and the 3-hydroxyl group protected to provide compound 18.

Similarly, the remaining compounds can likewise be modified to generate one or more intermediates used in the methods of this invention.

Example 4

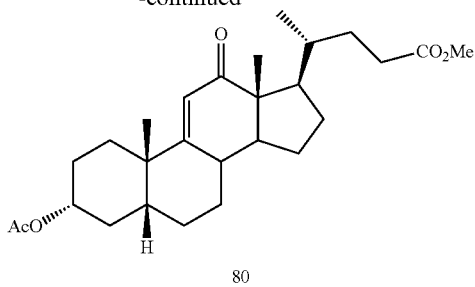

80

Synthesis of Compound 80 from Compound 79 by a Method of this Invention compound 79 (120.0 g) was oxidized using 70% tert-butyl hydroperoxide (($CH_3$)$_3$C—O—OH) in water (35 equiv) and 10% sodium hypochlorite (NaOCl) (7.0 equiv; added in 7 hours duration) in ethyl acetate at 0-5° C. After work up, the organic layer was treated with sodium sulfite followed by PCC (1.0 equiv.,) treatment provided 185 g of residue. The residue on slurry purification in 20% aq., methanol (2 vol) provided 75.2 g (60.6% yield) pure compound 80.

Comparison Procedure of Synthesis of Compound 80 from Compound 79 Using $CrO_3$ $CrO_3$ (65 g, 599 mmol) was added in two lots (40 g and 25 g) to a solution of compound 79 (65 g, 139 mmol) in AcOH (975 mL) in a clean and dry flask. (Caution: Highly exothermic, control the temperature below 50° C. with ice water cooling as needed). The resulting mixture was heated at 30-35° C. for 3 h. Lower temperatures of 25-35° C. may be used. Upon reaction completion by TLC (30% EtOAc in hexane, NMT 2% of compound 79), isopropyl alcohol (108 mL) was added and the mixture was stirred for 15 min before the solvent was evaporated under vacuum below 60° C. To the residue material was added water (1200 mL) and MTBE (650 mL). The two phases were separated and the aqueous layer was extracted with MTBE (2×650 mL). The combined organic layer was washed with water (750 mL) and brine solution (332 mL). The solvent was completely removed under vacuum below 50° C. To the residue was added methanol (195 mL) and the solvent was completely removed via vacuum distillation below 50° C. Methanol (130 mL) was added again and the mixture was cooled to 10-15° C., stirred for 1 h at 10-15° C., filtered and the cake was washed with chilled (0-5° C.) methanol (65 mL). The white solid was dried in a hot air drier at 50-55° C. until the LOD is NMT 0.5% to afford compound 80 (36 g, 53.7% yield).

$^1$H NMR (500 MHz, CDCl$_3$): δ=5.71 (s, 1H), 4.71-4.75 (m, 1H), 3.66 (s, 3H), 2.37-2.42 (m, 3H), 2.02-2.31 (m, 2H), 2.0 (s, 3H), 1.67-1.98 (m, 9H), 1.24-1.56 (m, 9H), 1.19 (s, 3H), 1.01-1.02 (d, J=6.5 Hz, 3H), 0.90 (s, 3H).

$^{13}$C NMR (500 MHz, CDCl$_3$): δ=204.9, 174.5, 170.4, 163.8, 123.6, 73.7, 53.4, 53.0, 51.3, 47.2, 41.7, 39.8, 37.7, 35.2, 35.0, 33.9, 31.4, 30.5, 29.6, 27.6, 27.3, 26.4, 26.1, 24.1, 21.2, 19.4, 10.6.

Mass (m/z)=445.0 [M$^+$+1], 462.0 [M$^+$+18].

IR=3437, 3045, 2946, 2870, 1729, 1680, 1252, 1168, 1020, cm$^{-1}$.

m.p.=137-139° C. (from EtOAc/hexanes mixture).

[α]$_D$=+93 (c=1% in CHCl$_3$).

Example 5

The following table shows the results of the preparation of compound 80 from compound 79 using either $CrO_3$ or ($CH_3$)$_3$C—O—OH and NaOCl as the oxidizing agent.

| Reagent | INPUT | OUTPUT | YIELD | HPLC-RI (PURITY)* | HPLC-RI (ASSAY)** |
|---|---|---|---|---|---|
| $CrO_3$ | 2.5 Kg | 1.0 Kg | 38.70% | 82.75% | 73.90% |
| $CrO_3$ | 12.2 Kg | 6.2 Kg | 49.20% | 80.29% | 75.30% |
| ($CH_3$)$_3$C—O—OH and NaOCl | 20.0 g | 13.0 g | 63% | 96.62% | 90.20% |
| ($CH_3$)$_3$C—O—OH and NaOCl | 20.0 g | 12.8 g | 62% | 97.06% | 89.60% |
| ($CH_3$)$_3$C—O—OH and NaOCl | 50.0 g | 32.0 g | 62% | 95.35% | 87.30% |
| ($CH_3$)$_3$C—O—OH and NaOCl | 50.0 g | 31.5 g | 61% | 93.50% | 86.00% |
| ($CH_3$)$_3$C—O—OH and NaOCl | 120.0 g | 75.2 g | 61% | 96.00% | 86.20% |

*purity based on ratio of compound peak area to total peak area
**purity based on ratio of compound peak area to the peak area of a known reference standard Example 6

Identification of Peroxide Compound 81

Figure 2:
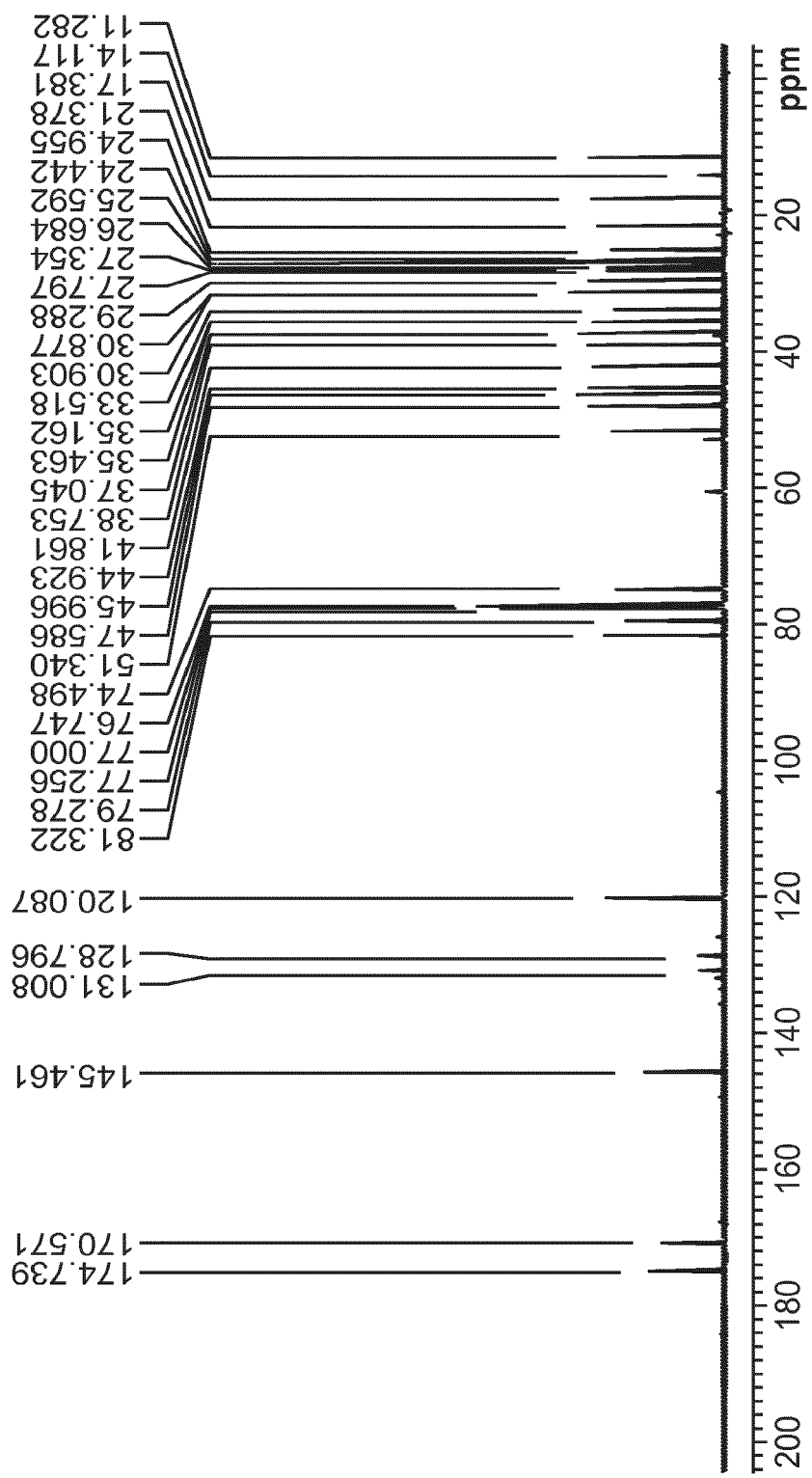
FIG. 2 provides a $^{13}$C NMR spectrum of compound 9 using a 125 MHz instrument.
Figure 3:
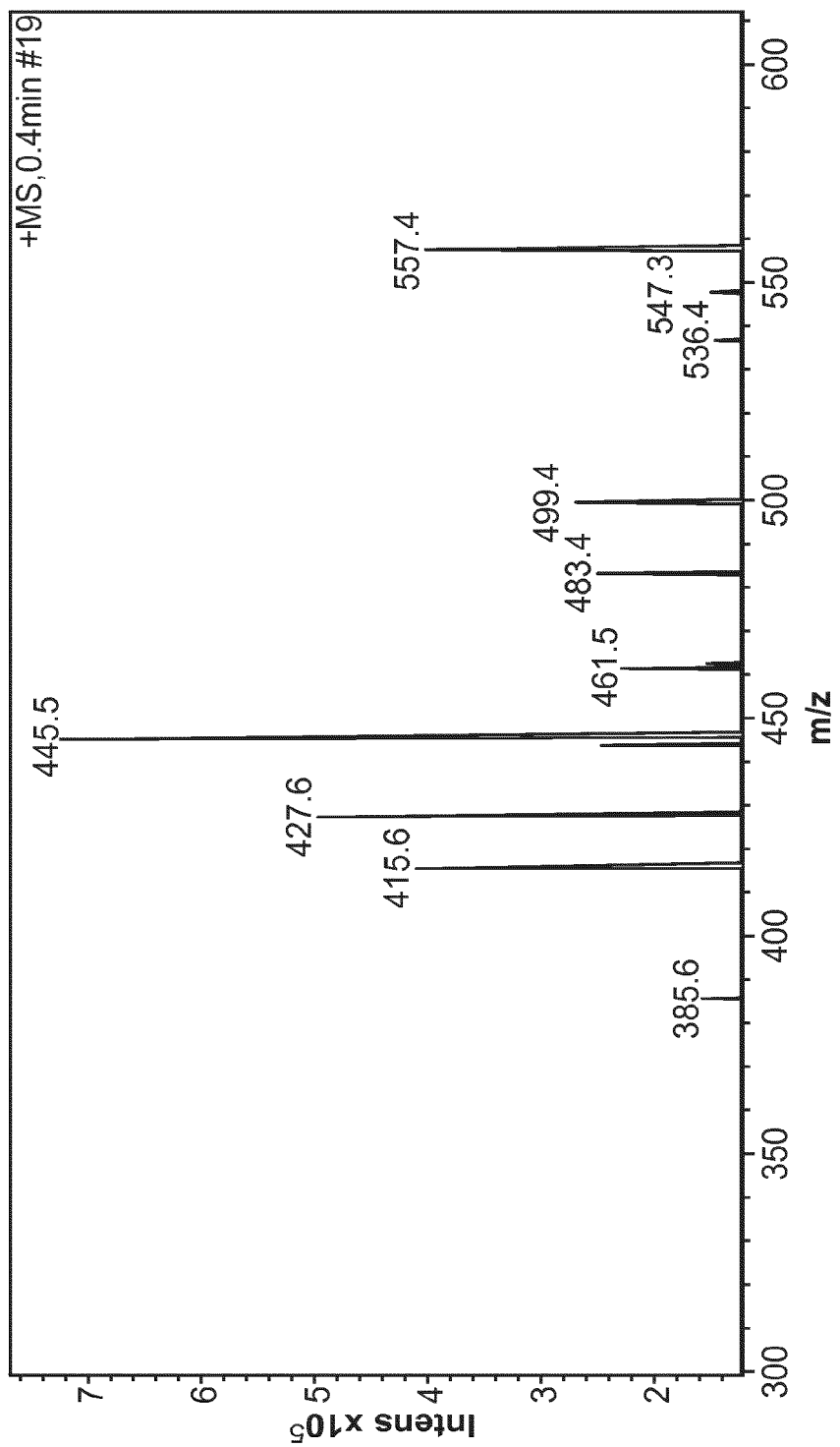
FIG. 3 provides a mass spectrum of compound 9.

After filtration of pure compound 80, the filter mother liquor (enriched with impurity ~30% at with a retention time of 3.14 minutes) was collected. The 3.14 minute impurity was isolated by column chromatography, which provided 100 mg of a pure product as an oil. NMR & Mass data revealed that the impurity is 12-tert-butylperoxy compound 81, which are provided in FIGS. 1-3.

Example 7

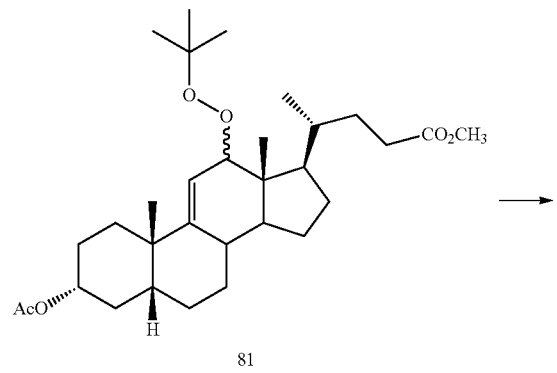

81

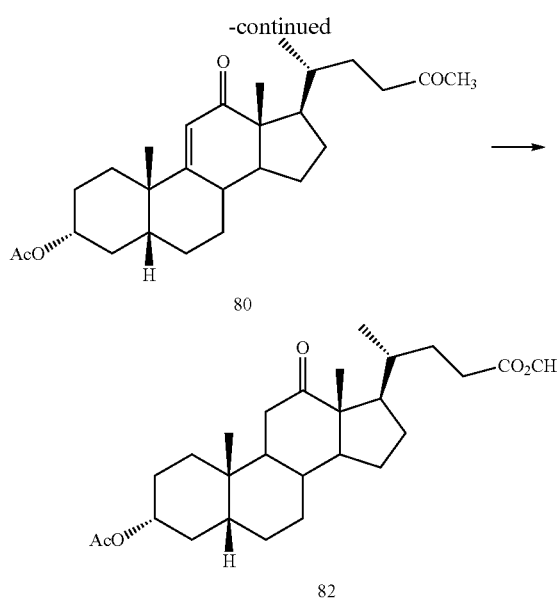

The 12-tert-butylperoxycompound 81 (50 mg) was treated with Pd/C (12 wt %), tert-butyl hydroperoxide (5 equiv) and potassium carbonate (0.025 equiv) in dichloromethane (10 parts) at room temperature for 24 hours, HPLC analysis revealed still presence of 89% of un-reacted compound 12-tert-butylperoxy 81 and observed only 11% of compound 80.

Compound 80 (10.0 g) was hydrogenated using commercial dry 10% Pd/C (25 wt %) in ethyl acetate (25 parts) at 45-50° C. under hydrogen pressure for 18 hours provided ~25% of allylicalcohol which was treated with PCC (1.2 equiv) at room temperature for 2 hours, then washed with water & brine solution. A half of the organic layer was distilled under vacuum and then re-subjected for hydrogenation using fresh Pd/C (25 wt %) at 45-50° C. under 50 psi hydrogen pressure for 18 hours, which provided 9.5 g of compound 82 (95% yield with 87% HPLC-RI purity).

Example 8

In Scheme 2 below, there is provided a scheme for the total synthesis of deoxycholic acid.

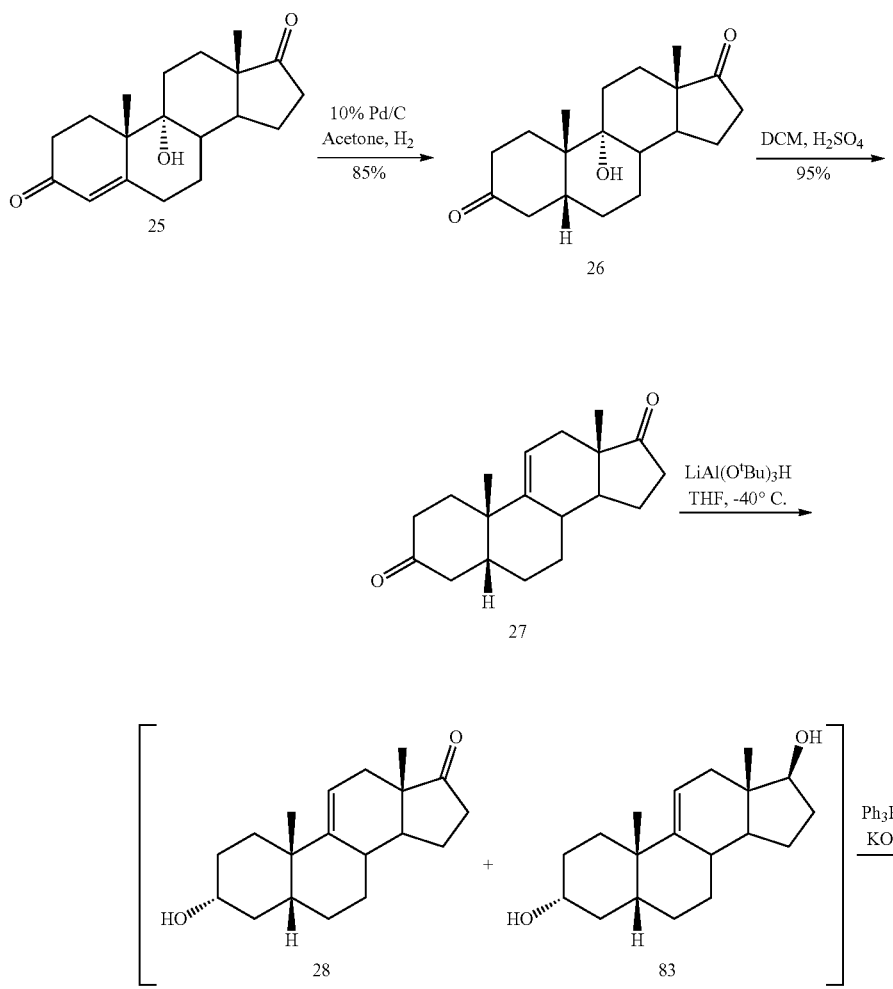

-continued
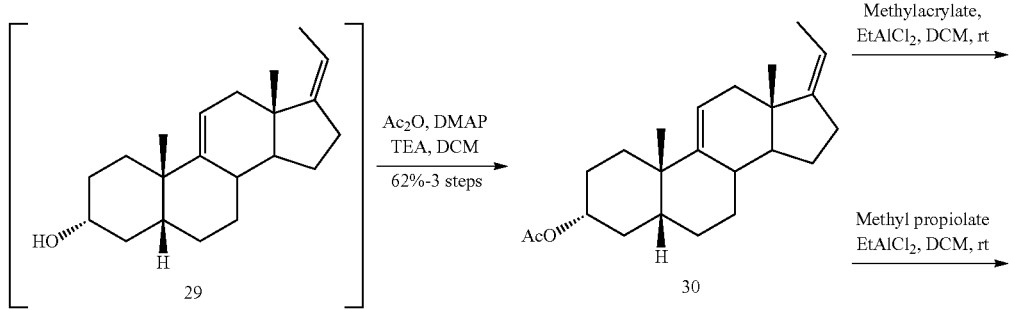
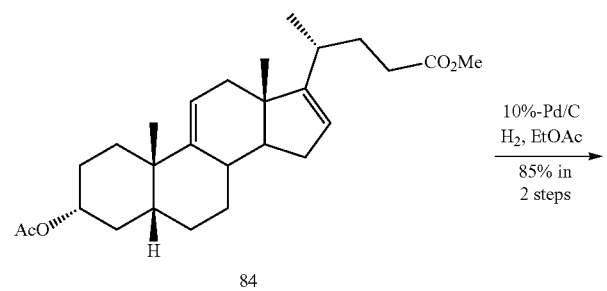
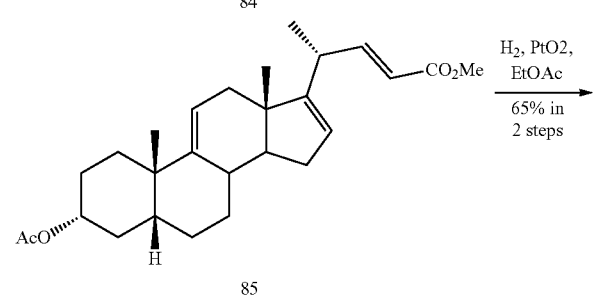
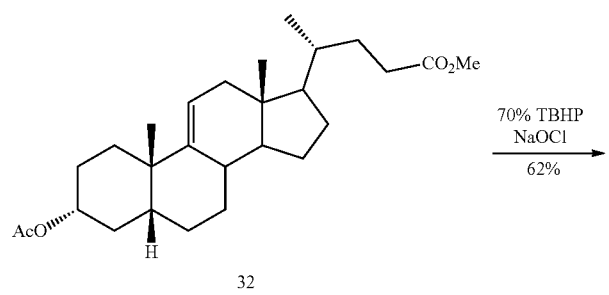
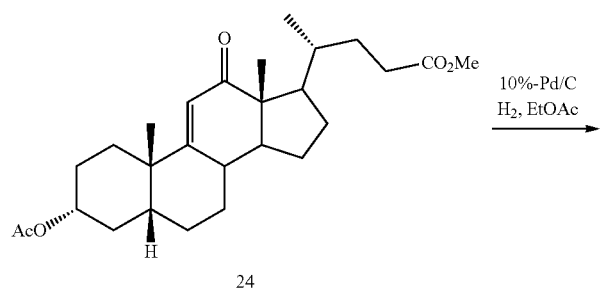

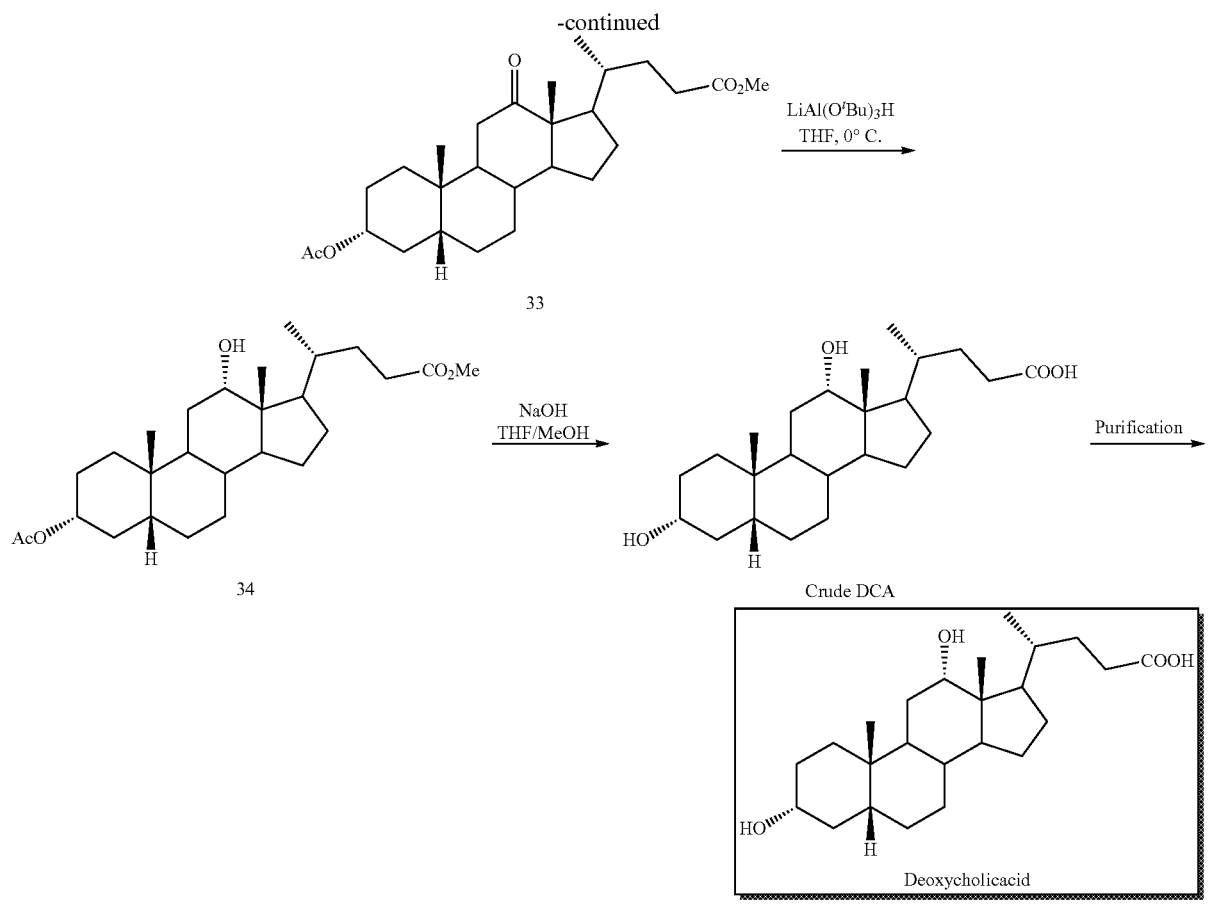

Conversion of Compound 25 to Compound 26:
Selection of Solvent

Several solvents were studied in the modification of this step: The following experiments were conducted using the above solvents and the results are tabulated below.

| S. No. | Input (g) | Solvent | Output (g) | Remarks |
|---|---|---|---|---|
| 1 | 1.0 | DMF | 0.9 | 5β-product: 85.8% by HPLC-RI<br>5α-product: 8.6% |
| 2 | 0.5 | Acetone | 0.45 | 5β-product: 88.5%<br>5α-product: 7.8% |
| 3 | 0.3 | IPA | 0.25 | 5β-product: 81.5%<br>5α-product: 11.8% |
| 4 | 0.3 | Ethanol | 0.25 | 5β-product: 68.6%<br>5α-product: 14.3% |
| 5 | 0.3 | 3% Aq acetone | 0.25 | 5β-product: 86.9%<br>5α-product: 8.5% |
| 6 | 0.3 | DCM | 0.25 | 5β-product: 47.2%<br>5α-product: 32.7% |
| 7 | 0.3 | EtOAc | 0.25 | 5β-product: 78.7%<br>5α-product: 13.2% |
| 8 | 0.3 | MeOH | 0.25 | Observed 3-methoxy 3,9-single bond |
| 9 | 0.3 | Hexane | 0.25 | 5β-product: 50.5%<br>5α-product: 12.9% |
| 10 | 0.3 | n-Butanol | 0.25 | 5β-product: 58.1%<br>5α-product: 34.9% |
| 11 | 0.3 | THF | 0.25 | 5β-product: 77.7%<br>5α-product: 13.9% |
| 12 | 0.3 | MTBE | 0.25 | 5β-product: 57.5%<br>5α-product: 34.0% |
| 13 | 5.0 | 1,4-Dioxane | 4.5 | 5β-product: 43.8%<br>5α-product: 1.1%, rxn not completed. |

When dichloromethane, methanol or ethyl acetate was used as a solvent as solvent in the hydrogenation of compound 25, complete consumption of the starting material was observed (by TLC). After isolation of the product and analysis by HPLC-RI, both 5α- and 5β-isomers of compound 26 were formed in an about 1:1 ratio. When acetone was used as solvent in the hydrogenation of compound 25, complete consumption of the starting material was observed (by TLC). After isolation of the product and analysis by HPLC-RI, 5β-isomer of compound 26 was almost exclusively formed and less than 10% formation of 5α-isomer. Thus, acetone provided more than 90% selectivity and more than 85% yield in this step.

To a solution of 9α-Hydroxyandrost-4-ene-3,17-dione (150.0 g) in acetone (3600 mL) was added 10% of Pd/C (12 g, 8 wt %, 50% wet) and the resulting slurry was hydrogenated in autoclave (50 psi) for 5 h at 25-25° C. Upon complete disappearance of the starting material, as evidenced by TLC (30% EtOAc in DCM), the crude reaction mixture was filtered through a CELITE® bed (20 g) and washed with dichloromethane (1500 mL). The filtrate was removed under vacuum and the crude product (145.0 g) was obtained as a white solid. This crude product was combined with (145.0 g) acetone (300 mL.) at 0° C., stirred for 1 h, then filtered and washed with chilled acetone (150 mL) and dried under vacuum at 50° C. This provided compound 26 (129 g, 85%) as a white solid.

TLC: p-Anisaldehyde charring. $R_f$ for compound 26=0.48 and $R_f$ for compound 25=0.3. Eluent was 30% EtOAc in DCM.

$^1$H NMR (500 MHz, CDCl$_3$): δ=2.40-2.37 (m, 1H), 2.11-.2.02 (m, 2H), 1.91-1.31 (m, 19H), 0.96 (s, 3H), 0.84 (s, 3H).

$^{13}$C NMR (125 MHz, CDCl$_3$): δ=221.0, 95.7, 80.1, 47.0, 43.6, 38.6, 38.5, 37.1, 35.9, 33.41, 32.9, 32.0, 27.9, 26.9, 21.5, 20.2, 20.0, 12.6.

Mass (m/z)=305.0[M$^+$+1], 322.0 [M$^+$+18].

IR (KBr)=3443, 2938, 1722, 1449, 1331, 1138 cm$^{-1}$.

m.p=213-216° C. (from acetone).

$[α]_D$=+116 (c=1% in CHCl$_3$).

HPLC/RI Purity: 99.0%.

Conversion of Compound 26 to Compound 27:

To a solution of compound 26 (121 g) in DCM (1815 mL) was added sulfuric acid (19.1 mL) over 15 minutes under an inert atmosphere at 5-10° C. The temperature was raised to 25-35° C., and the mixture was stirred for 2 h. At this point the reaction was determined to be complete (TLC, 30% EtOAc in DCM). The mixture was washed with water (600 mL) and then washed with 10% aqueous NaHCO$_3$ solution (600 mL). The organic layer was again washed with water (200 mL) followed by saturated brine solution (200 mL). The solvent was then distilled under vacuum, providing compound 27 (108.2 g, 95%) as an off-white solid. The crude product was used in the next step without further purification.

TLC: p-Anisaldehyde charring, $R_f$ for compound 27=0.76 and $R_f$ for compound 25=0.44. Eluent was 30% EtOAc in DCM.

$^1$H NMR (500 MHz, CDCl$_3$): δ=5.61 (s, 1H), 2.57-2.47 (m, 2H), 2.42-2.24 (m, 4H), 2.20-2.05 (m, 3H), 1.99-1.86 (m, 2H), 1.85-1.84 (d, J=6 Hz 1H), 1.63-1.57 (m, 5H), 1.40-1.37 (d, J=13.5 Hz, 1H) 1.28-1.25 (dd, J=4.0, 13.5 Hz, 1H), 1.17 (s, 3H) 0.85 (s, 3H).

$^{13}$C NMR (125 MHz, CDCl$_3$): δ=221.3, 212.8, 140.1, 118.5, 48.5, 45.9, 44.3, 43.5, 39.0, 38.0, 37.3, 36.1, 35.8, 33.3, 28.8, 26.0, 25.5, 22.5, 13.9.

Mass (m/z)=287 [M$^+$+1], 304 [M$^+$+18].

IR (KBr)=3450, 2913, 1737, 1707,1413, 1403,1207 cm$^{-1}$.

m.p.=143.4-145.9° C. (from DCM).

$[α]_D$=+142 (c=1% in CHCl$_3$).

HPLC/RI Purity: 96.7%.

Conversion of Compound 27 to Compound 30:

To a solution of compound 27 (108.0 g) in THF (1080 mL) was added lithium tri-tert-butoxyaluminum hydride (700 mL) at −40 to −45° C. under an inert atmosphere. The resulting reaction mixture was stirred for 2 h at −40 to −45° C. Upon completion of the reaction, as evidenced by TLC (30% EtOAc in DCM), the reaction mixture was quenched by the addition of 2N HCl solution. The phases were separated and the resulting aqueous layer was extracted with dichloromethane (648 mL). The organic fractions were combined and washed with water (648 mL), followed by saturated brine solution (540 mL). The organic layer was evaporated under vacuum which afforded compound 28, dissolved in THF (540 mL).

To a solution of ethyltriphenylphosphonium bromide (417 g) in THF (216 mL) was added potassium tert-butoxide (1086 mL, 1 M solution in THF) drop wise over 20 min under nitrogen at 25-35° C. The resulting dark red reaction mixture was stirred for an additional 1 h at the same temperature. The above solution of compound 28 was added slowly in 30-40 minutes to the above suspension at 25-35° C. The reaction mixture was stirred for an additional 3-5 h, leading to complete consumption of the starting material (as evidenced by TLC; 30% EtOAc in DCM). The reaction mixture was quenched with into ice water (1.080 L). The aqueous layer was extracted with MTBE (2×540 mL) and the combined organic extracts were washed with saturated brine solution (540 mL) organic layer was concentrated under vacuum and the crude material was purified by using MTBE (2×540 mL) filtered, take filtrate distilled off solvent 25% under vacuum, To a solution of compound 29 was cool to 25° C. added triethylamine (105.2 mL), DMAP(4.5 g) and acetic anhydride (53.5 mL) at 25-35° C. under nitrogen. After stirring for 2 hr at 25-35° C., the reaction was determined to be complete by TLC (10% EtOAc in hexanes). The reaction mixture was washed with water (1080 mL) followed by brine solution (324 mL). The organic layer was concentrated under vacuum to afford Crude compound 30 (225 g), the residue was re-crystallized in 2% aq methanol provided 85 g of pure compound 30 (63.5% yield with 96% HPLC-RI purity).

TLC: p-Anisaldehyde charring, $R_f$ for compound 30=0.5 and $R_f$ for compound 29=0.15. Eluent=10% EtOAc in hexanes.

$^1$H NMR (500 MHz, CDCl$_3$): δ=5.38 (s, 1H), 5.20-5.18 (d, J=6.5 Hz, 1H), 4.76-4.72 (m, 1H), 2.40-2.35 (m, 3H), 2.25-2.22 (m, 1H), 2.09-2.03 (m, 3H), 2.01 (s, 3H), 1.98-1.49 (m, 10H), 1.41-1.31 (m, 2H), 1.27-1.16 (m, 3H), 1.07 (s, 3H), 0.79 (s, 3H).

$^{13}$C NMR (125 MHz, CDCl$_3$): δ=170.5, 150.0, 140.4, 119.6, 114.3, 74.7, 53.5, 42.0, 41.7, 39.6, 38.6, 35.6, 35.3, 33.8, 31.9, 29.5, 27.8, 26.7, 26.6, 25.5, 21.3, 16.9, 13.2 Mass (m/z)=342.9 [M$^+$+1], 360 [M$^+$+18].

IR (CHCl$_3$)=3440, 3035, 1730, 1451, 1367, 1258, 1028 cm$^{-1}$.

Mp=93.9-97.8° C.

$[α]_D$=+109 (c=1% in CHCl$_3$).

HPLC/RI Purity: 96.0%.

Conversion of Compound 30 to Compound 32 via compound 84:

To a solution of compound 30 (56 g) in DCM (560 mL) was added methyl acrylate (35.13 mL) at 0-5° C. under an inert atmosphere stirring for 60 min, solution was cool to 0-5° C., ethylaluminum dichloride (272.9 mL; 1.8 M in toluene), was added over period of 60 min. The temperature was then raised to 25-35° C. and the mixture was stirred for ~18 hr. At this point analysis by TLC (10% EtOAc in hexanes) showed the reaction to be complete, so the mixture was poured into ice cold water (1120 mL). The phases were separated and the aqueous layer was extracted with DCM (2×255 mL). The organic layers were combined and washed sequentially with water (560 mL) and brine solution (560 mL), the organic layer was evaporated under vacuum, which provided compound 84 (66 g) as an oil.

To a solution of compound 84 in ethyl acetate (550 mL), Pd/C (6.7 g) slurry in ethyl acetate (110 mL) was added at 25-35° C. The resulting slurry was stirred under −70 psi hydrogen pressure for ~16 h. The progress of the reaction was monitored by HPLC. The catalyst was filtered on a CELITE® bed (25 g) and the cake was washed with ethyl acetate (990 mL). The filtrate was evaporated under vacuum, which provided compound 32 (59 g, 85%) as a solid.

TLC: p-Anisaldehyde charring, $R_f$ for compound 32=0.32 and $R_f$ for compound 84=0.30 Eluent=10% EtOAc in hexanes.

¹H NMR (500 MHz, CDCl₃): δ=5.31 (s, 1H), 4.73 (m, 1H), 3.66 (s, 3H), 2.37-2.03 (m, 7H), 2.01 (s, 3H), 1.98-1.09 (m, 18H), 1.06 (s, 3H), 0.92-0.91 (d, J=6.0 Hz, 3H), 0.59 (s, 3H).

¹³C NMR (125 MHz, CDCl₃): δ=174.6, 170.5, 139.8, 119.5, 74.8, 56.0, 53.3, 51.4, 41.9, 41.7, 40.9, 38.5, 36.4, 35.4, 35.2, 33.8, 31.0, 30.9, 29.5, 28.2, 27.8, 26.8, 26.7, 25.2, 21.4, 17.9, 11.5

Mass (m/z)=448.2 [M⁺+18].

IR (KBr)=3435, 3039, 2941, 1729, 1448, 1435, 1252, 1022 cm⁻¹.

m.p.=122.1-123.9° C.

[α]$_D$=+56 (c=1% in CHCl₃).

HPLC/RI Purity: 93.0%.

Conversion of Compound 30 to Compound 32 via compound 85:

Ethyl aluminum dichloride (104.5 mL, 192 mmol, 1.8 M in toluene) was added to a solution of methyl propiolate (13.58 mL, 153 mmol) in DCM (100 mL) at 0° C. under inert atmosphere. The resulting solution was stirred for 15 min and then compound 30 (22 g, 64.3 mmol) was added. After stirring for an additional 20 min at 0° C., the temperature was raised to 25° C. and held there for a further 18 h. At this point the reaction was determined to be complete by TLC, and the mixture was poured into cold (0° C.) water (200 mL). The phases were separated and the aqueous layer was extracted with DCM (150 mL). The organic layers were combined and washed sequentially with water (200 mL) and saturated brine solution (100 mL). It was then dried over anhydrous Na₂SO₄ (40 g) and filtered. The filtrate was concentrated under vacuum and the resulting solid was purified by slurring in methanol (280 mL) to provide compound 85 (17.5 g 68%) as a white solid.

TLC: p-anisaldehyde charring, R$_f$ for 85=0.32 and R$_f$ for 30=0.5.

TLC mobile phase: 10% EtOAc in hexanes.

¹H NMR (500 MHz, CDCl₃): δ=6.92-6.926 (q, J=7.5, 15.5 Hz, 1H), 5.80-5.83 (d, J=16 Hz, 1H), 5.37-5.43 (m, 2H), 4.73-4.75 (m, 1H), 3.73 (s, 3H), 3.02-3.04 (t, J=6.5 Hz, 1H), 2.15-2.23 (m, 3H), 2.05-2.08 (m, 3H), 2.01 (s, 3H), 1.48-1.99 (m, 8H), 1.24-1.34 (m, 2H), 1.20-1.21 (d, J=5 Hz, 3H), 1.11-1.17 (m, 1H), 1.07 (s, 3H), 0.67 (s, 3H).

¹³C NMR (125 MHz, CDCl₃): δ=170.5, 167.2, 155.0, 153.7, 141.6, 124.0, 118.8, 118.7, 74.6, 53.9, 51.3, 45.7, 41.7, 38.8, 37.1, 35.5, 35.3, 34.6, 33.7, 31.8, 29.5, 27.7, 26.5, 26.5, 21.3, 19.7, 15.7.

Mass (m/z)=444.0 [M⁺+18].

IR (KBr)=3443, 3030, 2930,1719,1650,1247, 1359, 1032, 1170 cm⁻¹.

m.p.=114-116° C. (from methanol)

[α]$_D$=+102 (c=1% in CHCl₃).

ELSD Purity: 99.7%, Retention time=19.57, (Inertsil ODS 3V 250×4.6 mm, 5 um), ACN: 0.1% TFA in water (90:10).

To a solution of compound 85 (17.5 g, 41 mmol) in EtOAc (350 mL) was added PtO₂ (4.37 g), and the resulting slurry was hydrogenated in a Parr apparatus (70 psi) for 14-16 h. At this point the reaction was determined to be complete by TLC. The mixture was filtered through a small plug of CELITE® and the solvent was removed under vacuum, affording compound 32 (17.0 g, 96.0%) as a white solid. The above product was used in the next step without further purification.

TLC: p-anisaldehyde charring, R$_f$ for 32=0.32 and R$_f$ for 85=0.30.

TLC mobile phase: 10%—EtOAc in hexanes.

¹H NMR (500 MHz, CDCl₃): δ=5.31 (s, 1H), 4.73 (m, 1H), 3.66 (s, 3H), 2.03-2.37 (m, 7H), 2.01 (s, 3H), 1.09-1.98 (m, 18H), 1.06 (s, 3H), 0.91-0.92 (d, J=6.0 Hz, 3H), 0.59 (s, 3H).

¹³C NMR (125 MHz, CDCl₃): δ=174.6, 170.5, 139.8, 119.5, 74.8, 56.0, 53.3, 51.4, 41.9, 41.7, 40.9, 38.5, 36.4, 35.4, 35.2, 33.8, 31.0, 30.9, 29.5, 28.2, 27.8, 26.8, 26.7, 25.2, 21.4, 17.9, 11.5

Mass (m/z)=448.2 [M⁺+18].

IR (KBr)=3435, 3039, 2941, 1729, 1448, 1435, 1252, 1022 cm⁻¹.

m.p.=122.1-123.9° C. (from EtOAc).

[α]$_D$=+56 (c=1% in CHCl₃)

ELSD Purity: 97.7%: Retention time=14.57 (ZORBAX SB C-18 150×4.6 mm, 5 um, ACN: 0.1% TFA in water (90:10)

Conversion of Compound 32 to Compound 24:

To a solution of compound 32 (20 g) in ethyl acetate (200 mL) was added 70% TBHP in water (200 mL) reaction solution was cool to 0° C., was slowly added 10% Sodium hypochlorite for about 6-7 h at 0-5° C., stir for 2-3 h at same temp. Upon complete disappearance of compound 32 by TLC (eluent=20% EtOAc in hexanes), separate the organic layer and the aqueous layer extracted with ethyl acetate (60 mL). the combined organic layer was washed with water (2×400 mL) followed by treated with 20% sodium sulfite sol (220 mL) at 50-55° C. for 2 h, separate two layers, organic layer was treated with pyridinium chlorochromate (10.9 g) for 6-8 h at 25-30° C. Upon complete disappearance of allylicalcohol by TLC (eluent=20% EtOAc in hexanes), the organic layers were washed with hot water (4×500 mL) followed by saturated brine solution (100 mL). Organic layer was evaporated under vacuum at 45-50° C. The resulting crude material was purified by stirring it with 20% aqueous methanol (40 mL) at 5-10° C. for 1 h filtered; the cake was washed with 20% aqueous methanol (20 mL) and then dried under vacuum at 45-50° C., which provided compound 24 (13 g) as a pale yellow solid.

TLC: p-Anisaldehyde charring, R$_f$ for compound 24=0.28 and R$_f$ for compound 32=0.52. Eluent=20% EtOAc in hexanes.

¹H NMR (500 MHz, CDCl₃): δ=5.71 (s, 1H), 4.75-4.71 (m, 1H), 3.66 (s, 3H), 2.42-2.37 (m, 3H), 2.31-2.02 (m, 2H), 2.0 (s, 3H), 1.98-1.67 (m, 9H), 1.56-1.24 (m, 9H), 1.19 (s, 3H), 1.02-1.01 (d, J=6.5 Hz, 3H), 0.90 (s, 3H).

¹³C NMR (500 MHz, CDCl₃): δ=204.9, 174.5, 170.4, 163.8, 123.6, 73.7, 53.4, 53.0, 51.3, 47.2, 41.7, 39.8, 37.7, 35.2, 35.0, 33.9, 31.4, 30.5, 29.6, 27.6, 27.3, 26.4, 26.1, 24.1, 21.2, 19.4, 10.6.

Mass (m/z)=445.0 [M⁺+1], 462.0 [M⁺+18].

IR=3437, 3045, 2946, 2870, 1729, 1680, 1252, 1168, 1020, cm⁻¹.

m.p.=141-142° C.

[α]$_D$=+102 (c=1% in CHCl₃).

HPLC/RI Purity: 96.2%.

Conversion of Compound 24 to Compound 33:

The hydrogenation of compound 24 on 10.0 g scale using dry 10% Pd/C (15 wt %) in ethyl acetate (20 parts) was added and applied about 50 psi hydrogen pressure and temperature raised to 70° C. After reaching temperature 70° C., observed increase of hydrogen pressure to about 60 psi, at these conditions maintained for 60 h. After 60 hours 0.6% of compound 24 and 2.75% of allylic alcohol were still observed, so further stirred for additional 12 h (observed 0.16% of allylic alcohol and 0.05% of compound 24). After work-up, the reaction provided 9.5 g of residue.

Another hydrogenation reaction on 25 g of compound 24 with above conditions for 76 h provided 24.5 g of residue.

Method A

10% Pd/C (900 mg) was added to a solution of compound 24 (2.0 g, 4.5 mmol) in EtOAc (150 mL) and the resulting slurry was hydrogenated in a Parr apparatus (50 psi) at 50° C. for 16 h. At this point the reaction was determined to be complete by TLC. The mixture was filtered through a small plug of CELITE® and the solvent was removed under vacuum, providing compound 33 (1.6 g, 80% yield) as a white solid.

TLC: p-anisaldehyde charring, $R_f$ for 33=0.36 and $R_f$ for 25=0.32.

TLC mobile phase: 20%—EtOAc in hexanes.

$^1$H NMR (500 MHz, CDCl$_3$): δ=4.67-4.71 (m, 1H), 3.66 (s, 3H), 2.45-2.50 (t, J=15 Hz, 2H), 2.22-2.40 (m, 1H), 2.01 (s, 3H), 1.69-1.96 (m, 9H), 1.55 (s, 4H), 1.25-1.50 (m, 8H), 1.07-1.19 (m, 2H), 1.01 (s, 6H), 0.84-0.85 (d, J=7.0 Hz, 3H).

$^{13}$C NMR (125 MHz, CDCl$_3$): δ=214.4, 174.5, 170.4, 73.6, 58.5, 57.4, 51.3, 46.4, 43.9, 41.2, 38.0, 35.6, 35.5, 35.2, 34.8, 32.0, 31.2, 30.4, 27.4, 26.8, 26.2, 25.9, 24.2, 22.6, 21.2, 18.5, 11.6,

Mass (m/z)=447.0 [M$^+$+1], 464.0 [M$^+$+18].

IR (KBr)=3445, 2953, 2868, 1731, 1698, 1257, 1029 cm$^{-1}$.

m.p.=142.2-144.4° C. (from EtOAc/hexanes mixture).

$[α]_D$=+92 (c=1% in CHCl$_3$).

ELSD Purity: 96.6%: Retention time=9.93 (Inertsil ODS 3V, 250×4.6 mm, 5 um, ACN: 0.1% TFA in water (90:10)

Method B

A slurry of 10% Pd/C (9 g in 180 mL of ethyl acetate) was added to a solution of compound 24 (36 g, 81 mmol) in EtOAc (720 mL) and the resulting slurry was treated with hydrogen gas (50 psi) at 45-50° C. for 16 h. (A total of 1080 mL of solvent may be used). At this point the reaction was determined to be complete by HPLC (NMT 1% of compound 24). The mixture was filtered through CELITE® (10 g) and washed with ethyl acetate (900 mL). The filtrate was concentrated to 50% of its volume via vacuum distillation below 50° C. To the concentrated solution was added pyridinium chlorochromate (20.8 g) at 25-35° C. and the mixture was stirred for 2 h at 25-35° C., when the reaction completed by HPLC (allylic alcohol content is NMT 1%).

The following process can be conducted if compound 24 content is more than 5%. Filter the reaction mass through CELITE® (10 g) and wash with ethyl acetate (360 mL). Wash the filtrate with water (3×460 mL) and then with saturated brine (360 mL). Dry the organic phase over sodium sulphate (180 g), filter and wash with ethyl acetate (180 mL). Concentrate the volume by 50% via vacuum distillation below 50° C. Transfer the solution to a clean and dry autoclave. Add slurry of 10% palladium on carbon (9 g in 180 mL of ethyl acetate). Pressurize to 50 psi with hydrogen and stir the reaction mixture at 45-50° C. for 16 h.

Upon complete consumption of compound 24 by HPLC (the content of compound 24 being NMT 1%), the reaction mixture was filtered through CELITE® (10 g) and the cake was washed with ethyl acetate (900 mL). The solvent was concentrated to dryness via vacuum distillation below 50° C. Methanol (150 mL) was added and concentrated to dryness via vacuum distillation below 50° C. Methanol (72 mL) was added to the residue and the mixture was stirred for 15-20 min at 10-15° C., filtered and the cake was washed with methanol (36 mL). The white solid was dried in a hot air drier at 45-50° C. for 8 h to LOD being NMT 1% to provide compound 33 (30 g, 83.1% yield).

Conversion of Compound 33 to Compound 34:

Method A

A THF solution of lithium tri-tert-butoxyaluminum hydride (1 M, 22.4 mL, 22.4 mmol) was added drop wise to a solution of compound 33 (2.5 g, 5.6 mmol) in THF (25 mL) at ambient temperature. After stirring for an additional 4-5 h, the reaction was determined to be complete by TLC. The reaction was quenched by adding aqueous HCl (1 M, 10 mL) and the mixture was diluted with EtOAc (30 mL). The phases were separated and the organic phase was washed sequentially with water (15 mL) and saturated brine solution (10 mL). The organic phase was then dried over anhydrous Na$_2$SO$_4$ (3 g) and filtered. The filtrate was concentrated under vacuum and the resulting solid was purified by column chromatography [29 mm (W)×500 mm (L), 60-120 mesh silica, 50 g], eluting with EtOAc/hexane (2:8) [5 mL fractions, monitored by TLC with p-anisaldehyde charring]. The fractions containing the product were combined and concentrated under vacuum to provide compound 34 (2.3 g, 91%) as a white solid.

TLC: p-anisaldehyde charring, $R_f$ for 34=0.45 and $R_f$ for 33=0.55.

TLC mobile phase: 30%—EtOAc in hexanes.

$^1$H NMR (500 MHz, CDCl$_3$): δ=4.68-4.73 (m, 1H), 3.98 (s, 1H), 3.66 (s, 3H), 2.34-2.40 (m, 1H), 2.21-2.26 (m, 1H), 2.01 (s, 3H), 1.75-1.89 (m, 6H), 1.39-1.68 (m, 16H), 1.00-1.38 (m, 3H), 0.96-0.97 (d, J=5.5 Hz, 3H), 0.93 (s, 3H), 0.68 (s, 3H).

$^{13}$C NMR (125 MHz, CDCl$_3$): δ=174.5, 170.5, 74.1, 72.9, 51.3, 48.1, 47.2, 46.4, 41.7, 35.8, 34.9, 34.7, 34.0, 33.5, 32.0, 30.9, 30.8, 28.6, 27.3, 26.8, 26.3, 25.9, 23.4, 22.9, 21.3, 17.2, 12.6

Mass (m/z)=449.0 [M$^+$+1], 466.0 [M$^+$+18].

IR (KBr)=3621, 2938, 2866, 1742, 1730, 1262, 1162, 1041, cm$^{-1}$.

m.p=104.2-107.7° C. (from EtOAc).

$[α]_D$=+56 (c=1% in CHCl$_3$).

ELSD Purity: 97.0%: Retention time=12.75 (Inertsil ODS 3V, 250×4.6 mm, 5 um, ACN: Water (60:40)

Method B

A THF solution of lithium tri-tert-butoxyaluminum hydride (1 M, 107.6 mL, 107.6 mmol) was added over 1 h to a solution of compound 33 (30.0 g, 67 mmol) in dry THF (300 mL) at 0-5° C. After stirring for an additional 4 h at 5-10° C., the reaction was determined to be complete by HPLC (NMT 1% of compound 33). The reaction was cooled to 0-5° C. and quenched by adding 4N HCl (473 mL). The phases were separated. The aqueous layer was extracted with DCM (2×225 mL) and the combined organic phase was washed sequentially with water (300 mL) and saturated brine solution (300 mL). The organic phase was then was concentrated to dryness by vacuum distillation below 50° C. Methanol (150 mL) was added to the residue and concentrated to dryness by vacuum distillation below 50° C. Water (450 mL) was then added to the residue and the mixture was stirred for 15-20 min., filtered and the cake was washed with water (240 mL). The white solid was dried in a hot air drier at 35-40° C. for 6 h to provide compound 34 (30 g, 99.6%).

Conversion of Compound 34 to crude DCA:

Method A

A solution of LiOH (187 mg, 4.4 mmol) in H$_2$O (2.0 mL) was added to a solution of compound 34 (500 mg, 1.11 mmol) in THF (8 mL) and MeOH (8 mL). The resulting mixture was stirred for 3-4 h at 50° C. Upon complete disappearance of the starting material by TLC, the reaction mixture was concentrated under vacuum. A mixture of water (10 mL) and 3 N HCl (1 mL) were combined and cooled to 0° C. and then added to the crude product. After stirring for 1 h at 0° C., the precipitated solids were filtered and then washed with water (10 mL) and hexane (20 mL). Drying under vacuum at room temperature provided deoxycholic acid (DCA, 400 mg, 91% yield) as a white solid.

TLC: p-anisaldehyde charring, $R_f$ for DCA=0.32 and $R_f$ for 2.1a=0.82.

TLC mobile phase: 10%—Methanol in DCM.

$^1$H NMR (500 MHz, DMSO): δ=11.92 (s, 1H), 4.44 (s, 1H), 4.19 (s, 1H), 3.77 (s, 1H), 3.35-3.36 (m, 1H), 2.19-2.21 (m, 1H), 2.08-2.10 (m, 1H), 1.73-1.80 (m, 4H), 1.43-1.63 (m, 6H), 1.15-1.35 (m, 12H), 0.98-1.05 (m, 2H), 0.89-0.90 (d, J=6.0 Hz, 3H), 0.83 (s, 3H), 0.58 (s, 3H).

$^{13}$C NMR (125 MHz, DMSO): δ=174.8, 71.0, 69.9, 47.4, 46.1, 46.0, 41.6, 36.3, 35.6, 35.1, 34.9, 33.8, 32.9, 30.8, 30.7, 30.2, 28.6, 27.1, 27.0, 26.1, 23.5, 23.0, 16.9, 12.4.

Mass (m/z)=393 [M$^+$, +1].

IR=3363, 2933, 2863, 1694, 1453, 1372, 1042, cm$^{-1}$.

m.p.=171.4-173.6° C. (from ethanol); 174-176° C. (Alfa Aesar) and 171-174° C. (Aldrich)

$[α]_D$=+47 (c=1% in EtOH), +540 (c=2% in ethanol) [Alfa Aesar]

ELSD Purity: 99.7%: Retention time=5.25 (Inertsil ODS 3V, 250×4.6 mm, 5 um, ACN: 0.1% TFA in water (90:10).

Method B

A 20% solution of NaOH (40 g, 270 mmol) in H$_2$O (54 mL) was added to a solution of compound 34 (30 g, 67 mmol) in THF (120 mL) and MeOH (120 mL) at 0-5° C. The resulting mixture was stirred for 4 h at 25-35° C. Upon completion of reaction by HPLC (NMT 0.5% of compound 34 and intermediates), the solvent was removed via vacuum distillation below 50° C. The residue was dissolve in water (300 mL) and washed with DCM (2×150 mL). The pH of aqueous layer was adjusted to 1-2 with 2N HCl (~173 mL). The solids were filtered, washed thoroughly with water (3 L) and dried by a hot air drier at 70-75° C. until the moisture content is less than 2% to provide deoxycholic acid (DCA, 26 g, 99% yield) as a white solid.

Example 9

Deoxycholic Acid (DCA) Purification

1. Solvent Selection

Two solvent systems were explored for further purification of DCA:

10% Hexanes in EtOAc

DCM

The following experiments have been conducted and the experimental results are tabulated below.

| No. | Batch Size (g) | Solvent | Output (g) | Purity by HPLC |
|---|---|---|---|---|
| 1 | 136 | 10% Hexanes in EtOAC | 100 | 95% HPLC purity by RI detection |
| 2 | 9.5 | DCM* | 6.8 | >99% HPLC purity by RI detection |
| 3 | 4.0 | DCM* | 3.0 | >99% HPLC purity by RI detection |

*The DCA to be purified was dissolved in a mixture of methanol and DCM and then the methanol was removed by azeotropic distillation. The amount of methanol required to dissolve the crude DCA depends on how pure it is to begin with. Typical crude material was ~75% pure and could be dissolved at reflux using 10% methanol-DCA (by volume) using ~20 mL per gram. With purer DCA, the percentage of methanol had to be increased to 15%.

Effective purification was achieved by crystallization of the product from DCM following dissolution in a mixture of methanol and DCM and azeotropic removal of the methanol via atmospheric distillation.

2. Solvent Quantity

Experiments have been conducted using different solvent volumes and the experimental results are tabulated below.

| No. | Batch Size (g) | Solvent quantity | Output (g) | Purity by HPLC |
|---|---|---|---|---|
| 1 | 4.0 | 25 vol | 3.0 | 99.3% HPLC purity by RI detection |
| 2 | 5.0 | 15 vol | 3.56 | 99.3% HPLC purity by RI detection |
| 3 | 5.0 | 20 vol | 3.4 | 99.3% HPLC purity by RI detection |
| 4 | 100 | 15 vol | 70 | 99.3% HPLC purity by RI detection |
| 5 | 47 | 15 vol | 44 | 99.5% HPLC purity by RI detection |

Excellent recoveries and product quality were obtained at all solvent levels.

3. Isolation Temperature

The following experiments have been conducted by varying the isolation temperature and the results are tabulated below:

| No. | Batch Size (g) | Temp (° C.) | Output (g) | Purity by HPLC |
|---|---|---|---|---|
| 1 | 5.0 | 10-15 | 3.0 | 99.0% HPLC purity by RI detection. |
| 2 | 100 | 25-30 | 70 | 99.3% HPLC purity by RI detection. |
| 3 | 47 | 25-30 | 44 | 99.5% HPLC purity by RI detection. |

Higher quality product was obtained when isolation is done at 25-30° C. as compared to 10-15° C.

Purification of DCA in 100 g Scale

The final purification procedure for this step is given below:

| No. | Raw Material | Qty | Unit | M. Wt. | Mole | Mole ratio |
|---|---|---|---|---|---|---|
| 1 | Crude DCA | 100 | g | 392 | 0.255 | 1.0 |
| 2 | Dichloromethane | 5.0 | L | — | — | 50 V |
| 3 | Methanol | 250 | mL | — | — | 2.5 V |
| 4 | NaOH | 12.23 | g | 40 | 0.3058 | 1.2 |
| 5 | 2N HCl | 204 | mL | — | — | 2.04 V |
| 6 | Demineralised (D.M.)Water | 10 | L | — | — | 100 V |

Crude DCA (110 g) was dissolved in 10% methanol in DCM (2.5 L) at reflux temperature. To this clear solution 2.5 L of dichloromethane was added at reflux temperature and then about 3.0 L of solvent was distilled at atmospheric pressure (GC analysis of reaction mass supernatant revealed the presence of about 3% of methanol). The reaction slurry was cooled to 20-25° C. and then stirred for 3-4 h. The mixture was filtered and the solids were washed with DCM (300 mL). The product was dried in a hot air oven at 50-55° C. for 6-8 h.

The above dried DCA was added to water (1.0 L) and then 10% sodium hydroxide solution (122 mL) was added resulting in a clear solution. This solution was filtered through 5μ filter paper. The filtrate was diluted with water (2.0 L), and the pH was adjusted to 1-2 with 2N HCl solution (204 mL). The precipitated solids were stirred for 1 h, filtered and the solids were washed with additional water (7.0 L). After drying in a hot air oven at 70-75° C. for 16-20 h, purified DCA (~66 g with more than 99% purity by HPLC RI detection) was obtained as a white solid.

TLC: p-Anisaldehyde charring, $R_f$ for DCA=0.32 and $R_f$ for compound 34=0.82. Eluent=10% methanol in DCM.

$^1$H NMR (500 MHz, DMSO): δ=11.92 (s, 1H), 4.44 (s, 1H), 4.19 (s, 1H), 3.77 (s, 1H), 3.36-3.35 (m, 1H), 2.21-2.19 (m, 1H), 2.10-2.08 (m, 1H), 1.80-1.73 (m, 4H), 1.63-1.43 (m, 6H), 1.35-1.15 (m, 12H), 1.05-0.98 (m, 2H), 0.90-0.89 (d, J=6.0 Hz, 3H), 0.83 (s, 3H), 0.58 (s, 3H).

$^{13}$C NMR (125 MHz, DMSO): δ=174.8, 71.0, 69.9, 47.4, 46.1, 46.0, 41.6, 36.3, 35.6, 35.1, 34.9, 33.8, 32.9, 30.8, 30.7, 30.2, 28.6, 27.1, 27.0, 26.1, 23.5, 23.0, 16.9, 12.4.

Mass (m/z)=393 [M$^+$, +1].

IR=3363, 2933, 2863, 1694, 1453, 1372, 1042, cm$^{-1}$.

m.p.=171.4-173.6° C. (from ethanol); 174-176° C. (Alfa Aesar) and 171-174° C. (Aldrich).

Recrystallization of Deoxycholic Acid (DCA)

DCA obtained from Method B (26 g) above, was charged into a clean and dry flask. Methanol (65 mL) and DCM (585 mL) were added. The mixture was heated to reflux to obtain a clear solution. DCM (650 mL) was charged to the solution and the solvent was distilled atmospherically until 780 mL of solvent was collected. The mixture was assayed by GC to determine the solvent composition. If the methanol content is more than 2%, add DCM (200 mL) and distill atmospherically until 200 mL of distillate have been collected. (Check for the methanol content by GC). The reaction mixture was cooled over 1-2 h to 20-25° C. and stirred at this temperature for 3-4 h. The product was filtered and washed with DCM (81 mL), dried in a hot air drier at 50-55° C. for 8 h. The purity was determined by HPLC. If single max impurity is more than 0.1%, the above process is repeated.

The dried material from the above was charged in to a clean flask. Water (190 mL) was added and followed by 10% aqueous NaOH (3.18 g in 31.8 mL of water). The solution was filtered through 5μ filter paper and the filtrate was diluted with additional water (380 mL). The pH was adjusted to 1-2 with 2 N HCl (53 mL). The resulting solids was filtered, washed thoroughly with water (1.9 L), and dried in a hot air drier at 70-75° C. until the water content is below 1% to give DCA as a white solid (17 g, % of recovery: 65).

Example 10

Alternate Method of Synthesis and Purification of DCA from Compound 33

Step 1a—Hydrogenation of methyl 3α-acetoxy-12-oxo-5β-chol-9(11)-en-24-oate (24)

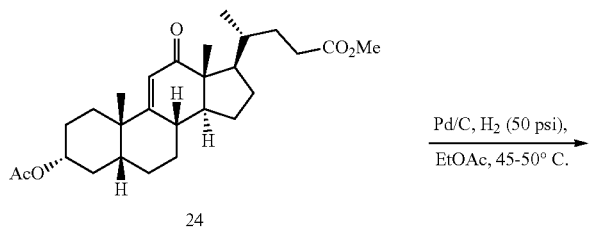

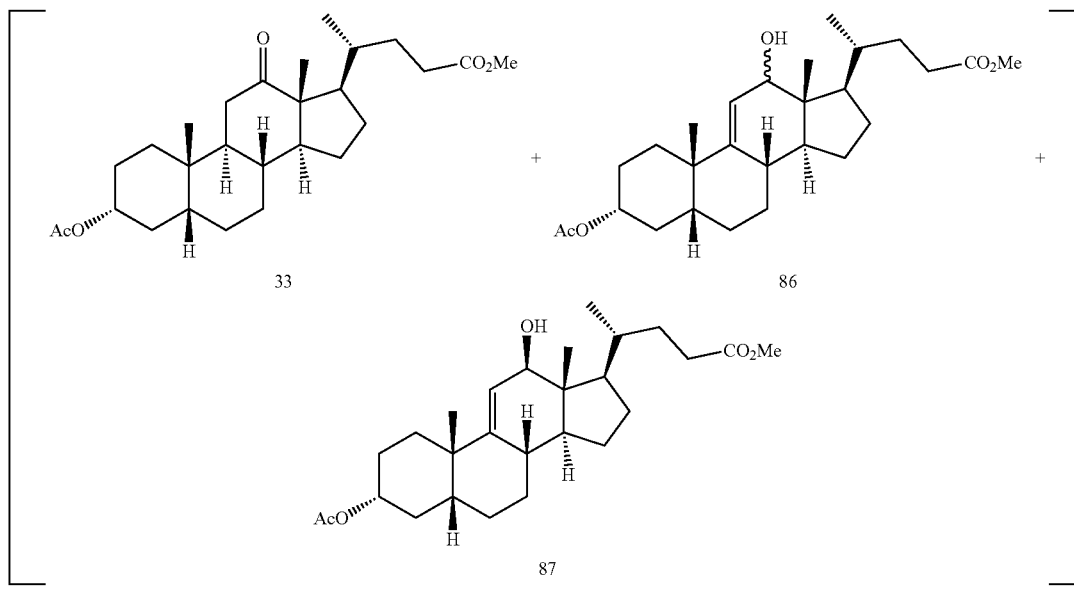

Dry Pd/C (75.0 g, 25 wt %) was added to 24 (300.0 g, 0.7 mol) in EtOAc (7.5 L, 25 vol). The reaction mixture was heated to 45° 50° C. and pressurized to 50 psi of $H_2$. HPLC analysis after 21 hours indicated <1.0% area under the curve (AUC) of 24 remained; 4.6% AUC of the allylic alcohol impurity 86 and 11.1% AUC of the 87 formed. The reaction mixture was cooled to 30° 35° C., filtered over HYFLO® (a flux calcined diatomaceous earth filter aid) (300 g) and washed with EtOAc (7.5 L) to remove the catalyst. The resulting filtrate was concentrated to about 6 L and taken forward without further manipulation (67.8% AUC by HPLC, 5.5% AUC of the allylic alcohol impurity 86 and 13.0% AUC of 87).

Step 1b/c—Oxidation of allylic alcohol 86 and 87 and rehydrogenation of 24 to methyl 3α-acetoxy-12-oxo-5β-cholan-24-oate (33)

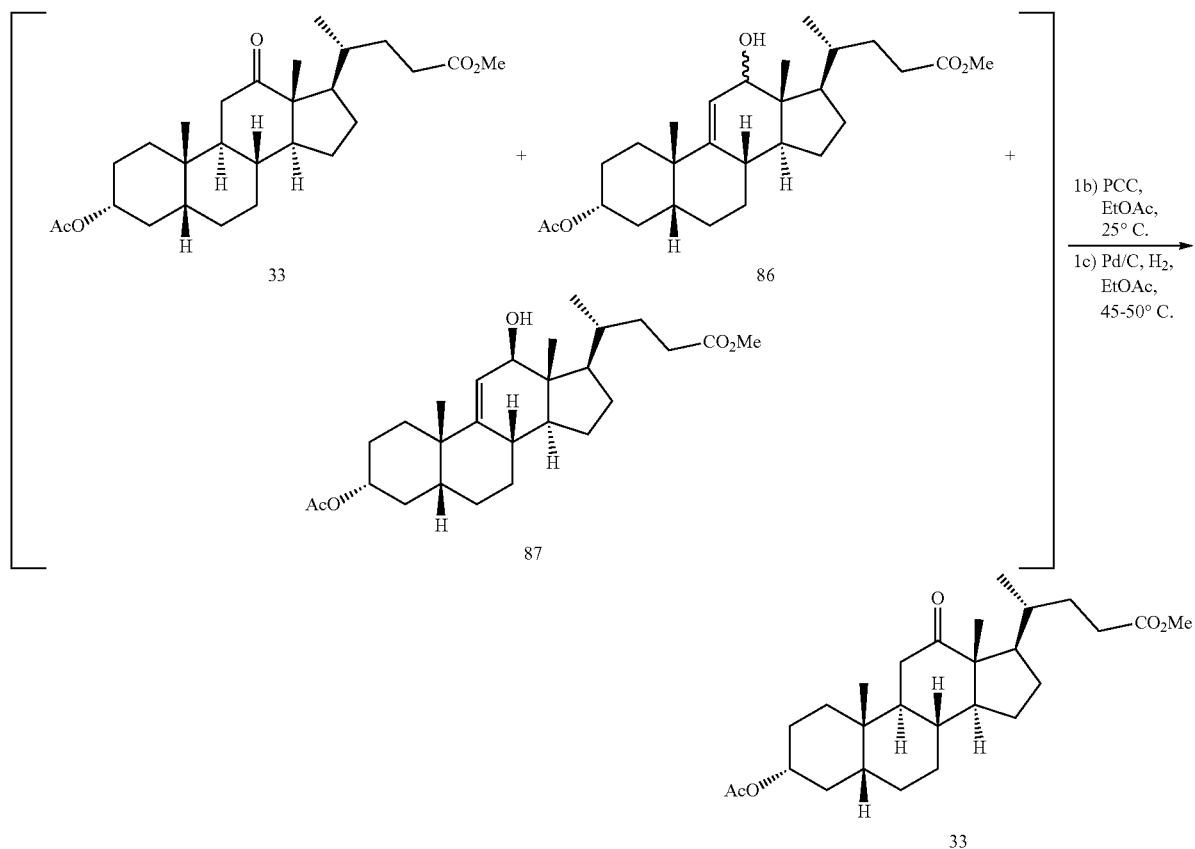

Step 1b—PCC Oxidation of Allylic Alcohol 86 and 87

A slurry of PCC (149.1 g, 1.03 equiv.) in EtOAc (1.5 L) was added to the 33 solution from above at 20°-25° C. The reaction was allowed to proceed for 3.5 hours where HPLC analysis showed that <1% AUC of the allylic alcohol 86 and <1% AUC of 87 remained. The reaction mixture was filtered over HYFLO® (a flux calcined diatomaceous earth filter aid) (300 g) and washed with EtOAc (3.0 L). The EtOAc filtrate was washed with deionized (DI) water (2×3.6 L) and brine (3.6 L), filtered over HYFLO® (300 g) and washed with EtOAc (3.0 L). The resulting filtrate was concentrated to ~7.5 L and taken forward without further manipulation (77.7% AUC by HPLC containing 5.3% AUC of 24).

Step 1c—Rehydrogenation of 24 to 33

Powder activated carbon DARCO® (60 g, 20 wt %) was added to the crude 33 solution from above containing 24. The resulting slurry was heated to 450-50° C. for 4 hours, cooled to 300-35° C. and filtered over CELITE®. The filter cake was washed with EtOAc (7.5 L), concentrated to ~7.5 L and added to dry Pd/C (60.0 g, 20 wt %). The reaction mixture was heated to 450-50° C. and pressurized to 50 psi of $H_2$ for 6 hours. HPLC analysis indicated <1.0% AUC of 24 remained; 1.1% AUC of 86 impurity and <1.0% AUC of 87 formed. The reaction was deemed complete and cooled to 300-35° C., filtered over CELITE® and washed with EtOAc (7.5 L). The EtOAc filtrate was concentrated to ~5 volumes and azeotroped with MeOH (2×4.5 L) back down to ~5 volumes. The resulting slurry was diluted with DI water (2.4 L) and maintained at 20-25° C. The slurry was filtered, washed with DI water (2×600 mL) and dried under vacuum at 40°-50° C. to yield 266 g (88%) of 33 (66.2% AUC by HPLC).

Step 2—Synthesis of 34

A solution of 33 (245 g, 0.5 mol) in THF (2.5 L) was cooled to 0°-5° C. and 1 M solution of Li(t-BuO)$_3$AlH (822.9 mL, 1.5 equiv.) was added while maintaining the temperature below 5° C. The reaction mixture was stirred at 50-10° C. for 22 hours. Reaction may be complete in 2-4 hours. HPLC analysis indicated that the reaction was complete with <1% of 33 remaining. The reaction was quenched with 4 M HCl (3.7 L) while maintaining the temperature below 20° C. The reaction mixture was extracted with $CH_2Cl_2$ (2×2.5 L) and the combined organic phases were washed with DI water (2×2.5 L). The $CH_2Cl_2$ phase was concentrated to afford 300 g (122%) of 34 (73.5% AUC by HPLC). $^1$H NMR analysis indicated that 9.7 wt % of THF and 0.8 wt % of $CH_2Cl_2$ remained.

Step 3—Synthesis of DCA

A NaOH solution (87.6 g, 4 equiv.) in DI water (438.6 mL) was added to a solution of 34 (245 g, 0.5 mol) in MeOH (980 mL) and THF (475 mL) at 0°-5° C. The reaction mixture was allowed to warm to 200-25° C. HPLC analysis showed that the reaction was complete after 1 hour with <0.5% 34 and <0.5% of the hydrolysis intermediates remaining. The reaction was diluted with DI water (2.5 L) and concentrated to ~10 volumes. The aqueous solution was washed with $CH_2Cl_2$ (2×1.3 L) and adjusted to pH 1.7-2.0 using 2 M HCl (1.6 L). A white slurry formed and was stirred at 200-25° C. for 1 hour. The slurry was filtered, washed with DI water (7×1 L) and dried under vacuum to yield 195 g (91%) of DCA (82.2% AUC by HPLC).

Step 4—Purification of DCA

A solution of DCA obtained above (190 g, 0.48 mol) in MeOH (475 mL) and $CH_2Cl_2$ (4275 mL) was heated to 35°-40° C. The MeOH/$CH_2Cl_2$ was distilled out of the mixture while $CH_2Cl_2$ (4740 mL) was added matching the rate of distillation. Analysis of the solvent composition by $^1$H NMR indicated 4.5 mol % of MeOH remained relative to $CH_2Cl_2$. The slurry was allowed to cool to 200-25° C. and held for 16 hours. The solids were isolated by filtration, washed with $CH_2Cl_2$ (600 mL) and dried under vacuum to yield 104 g (55%) of DCA (>99% AUC by HPLC-RID and 98.7% AUC by HPLC-CAD).

The recrystallization was repeated by heating a mixture of DCA (103 g, 0.3 mol) in MeOH (359 mL) and $CH_2Cl_2$ (1751 mL) to 35°-40° C. The MeOH/$CH_2Cl_2$ was distilled out of the mixture while $CH_2Cl_2$ (3760 mL) was added matching the rate of distillation. Analysis of the solvent composition by $^1$H NMR indicated 4.7 mol % of MeOH remained relative to $CH_2Cl_2$. The slurry was allowed to cool to 200-25° C. After 1 hour, the solids were isolated by filtration, washed with $CH_2Cl_2$ (309 mL) and dried under vacuum to afford 82 g (79%) of DCA (>99% AUC by HPLC-RID and 99.3% AUC by HPLC-CAD).

To assess the effect of additional purification and reprocessing, the product was recrystallized a third time prior to the normal final water isolation step. The above sample of DCA (80 g, 0.2 mol) in MeOH (240 mL) and $CH_2Cl_2$ (1400 mL) was heated to 35°-40° C. The MeOH/$CH_2Cl_2$ was distilled out of the mixture while $CH_2Cl_2$ (2000 mL) was added matching the rate of distillation. Analysis of the solvent composition by $^1$H NMR indicated 6.7 mol % of MeOH remained relative to $CH_2Cl_2$. The slurry was allowed to cool to 20°-25° C. After 1 hour, the solids were isolated by filtration, washed with $CH_2Cl_2$ (240 mL) and dried under vacuum to afford 72 g (89%) of DCA (99.7% AUC by HPLC-CAD).

The sample was slurried in DI water (840 mL) and diluted with a solution of NaOH (14.0 g) in DI water (140 mL). The resulting solution was filtered over CELITE® and washed with DI water (1.4 L). The filtrate was adjusted to pH 1.6 with 2 M HCl (~300 mL) resulting in a white precipitate which was held for 1 hour at 200-25° C. The product was isolated by filtration, washed with DI water (9.0 L) and dried under vacuum to afford 63 g (87%) of DCA (99.7% AUC by HPLC-CAD).

Example 11

A manufacturing process for deoxycholic acid key starting material compound 24 has been modified and made suitable for large scale production. The manufacturing process is safe, economical, environmentally-friendly and produces high quality final product that consistently meets specifications.

The manufacturing process involves:
Preparation of the Key Starting Material (i.e. Methyl 3α-acetoxy-12-oxo-5β-chol-9(11)-en-24-oate) compound 24.

The Key Starting Material is prepared in eight chemical steps from 9-α-hydroxyandrost-4-en-3,17-dione (9-HAD). Since some of the intermediates are not isolated, this part of the process corresponds to Stage-I to Stage-V. The structural assignments for all intermediates are consistent with NMR and Mass Spectral data. The detailed procedures for the final process along with the spectral data of the product from each step are provided in the Process section.

A schedule of impurities along with their status (isolated, identified, not observed, etc.), a list of raw materials, and a description of critical process parameters are all provided in the final sections of the report.

Based on the results of the process modification and the demonstration batch, the manufacturing process is suitable for its intended purpose.

Scheme 1-synthetic scheme starting from 9α-Hydroxyandrostenedione

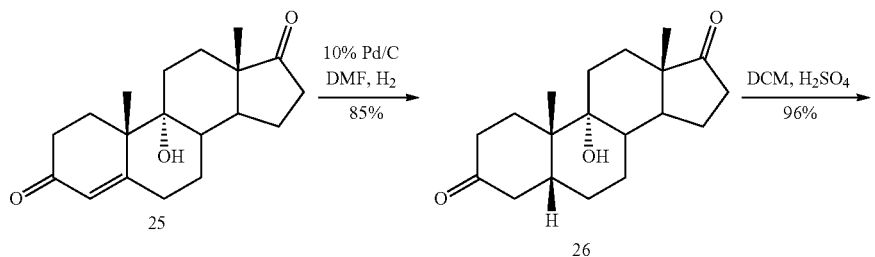

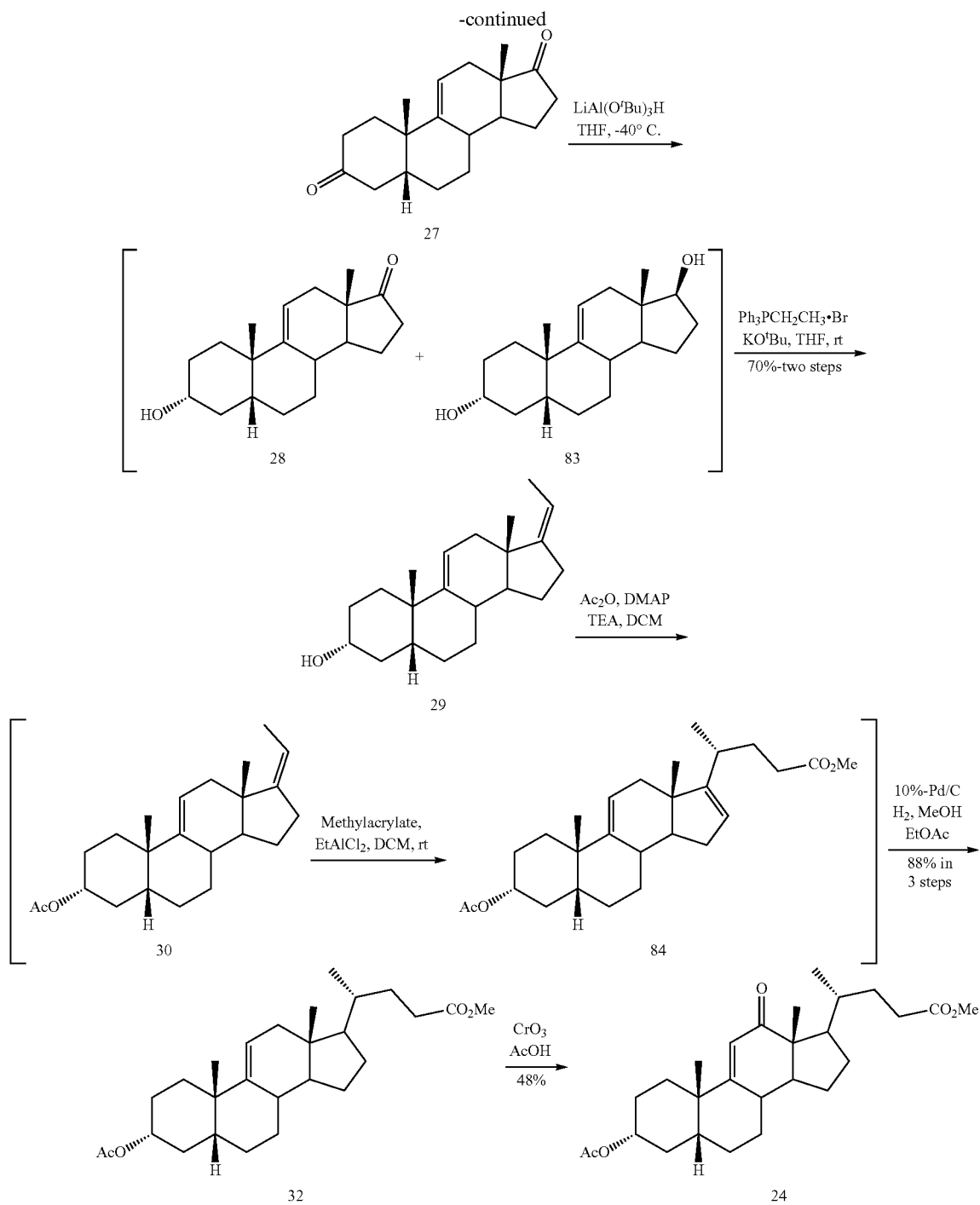

Modification of the Final Process

Drawbacks of the Initial Runs of the Proposed Process Steps

The process for the preparation of DCA was worked reasonably well on the initial run through the proposed route and we were able to prepare multi-gram quantities of synthetic DCA with pretty high purity, but disadvantages they are key starting material purity, yield and Wittig stage column chromatography not feasible for plant scale these things are successfully avoided by using crystallization methods in aqueous methanol, allylic oxidation reaction also improved good yield and purity of compound 24, the initial experimental procedure and results for each step are given below.

Modification of each step of the new process modifications was undertaken. These modification studies are described in this section. Attempts were made to combine steps to minimize work-ups and isolations, resulting in an increase in efficiency. The resulting process has a total of eight stages.—five steps are involved to prepare the regulatory starting material (key starting material, compound 24)

and three for its conversion to DCA. There is also one additional stage for the final purification.

Modification Study for Step 1

Chemical name of product: 9α-Hydroxy-5β-androstane-3,17-dione

Synthetic Scheme:

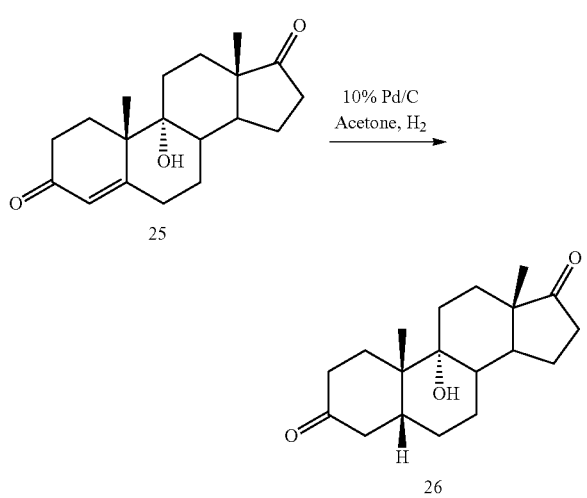

Modification Plan for Step 1
  Selection of solvent
  Solvent quantity
  Reaction time
  Catalyst quantity Selection of Solvent The following solvents were studied in the modification of this step:
  N,N-Dimethylformamide (DMF)
  Acetone
  Aqueous Acetone
  Dichloromethane (DCM)
  Methanol (MeOH)
  Ethanol (EtOH)
  Isopropyl alcohol (IPA)
  n-Butanol
  Tetrahydrofuran (THF)
  Methyl tert-butylether (MTBE)
  1,4-Dioxane
  Ethyl acetate (EtOAc)

The following experiments have been conducted using the above solvents and the results are tabulated below.

| S. No. | Input (g) | Solvent | Output (g) | Remarks |
|---|---|---|---|---|
| 1 | 1.0 | DMF | 0.9 | 5β-product: 85.8% by HPLC-RI |
|  |  |  |  | 5α-product: 8.6% |
| 2 | 0.5 | Acetone | 0.45 | 5β-product: 88.5% |
|  |  |  |  | 5α-product: 7.8% |
| 3 | 0.3 | IPA | 0.25 | 5β-product: 81.5% |
|  |  |  |  | 5α-product: 11.8% |
| 4 | 0.3 | Ethanol | 0.25 | 5β-product: 68.6% |
|  |  |  |  | 5α-product: 14.3% |
| 5 | 0.3 | 3% Aq acetone | 0.25 | 5β-product: 86.9% |
|  |  |  |  | 5α-product: 8.5% |
| 6 | 0.3 | DCM | 0.25 | 5β-product: 47.2% |
|  |  |  |  | 5α-product: 32.7% |

-continued

| S. No. | Input (g) | Solvent | Output (g) | Remarks |
|---|---|---|---|---|
| 7 | 0.3 | EtOAc | 0.25 | 5β-product: 78.7% |
|  |  |  |  | 5α-product: 13.2% |
| 8 | 0.3 | MeOH | 0.25 | Observed 3-methoxy 3,9- single bond |
| 9 | 0.3 | Hexane | 0.25 | 5β-product: 50.5% |
|  |  |  |  | 5α-product: 12.9% |
| 10 | 0.3 | n-Butanol | 0.25 | 5β-product: 58.1% |
|  |  |  |  | 5α-product: 34.9% |
| 11 | 0.3 | THF | 0.25 | 5β-product: 77.7% |
|  |  |  |  | 5α-product: 13.9% |
| 12 | 0.3 | MTBE | 0.25 | 5β-product: 57.5% |
|  |  |  |  | 5α-product: 34.0% |
| 13 | 5.0 | 1,4-Dioxane | 4.5 | 5β-product: 43.8% |
|  |  |  |  | 5α-product: 1.1%, rx not completed. |

Remarks:

When dichloromethane, methanol or ethyl acetate was used as a solvent in the hydrogenation of 25, complete consumption of the starting material was observed (by TLC). After isolation of the product and analysis by HPLC-RI, both 5α- and 5β-isomers of compound 26 were formed in an about 1:1 ratio.

When acetone was used as a solvent in the hydrogenation of 25, complete consumption of the starting material was observed (by TLC). After isolation of the product and analysis by HPLC-RI, almost exclusive formation of the 5β-isomer of compound 26 and less than 10% formation of 5α-isomer was observed.

Conclusion:

Based on the above experimental results, acetone was chosen as the preferred solvent, providing more than 90% selectivity and more than 85% yield in this challenging step.

Solvent Quantity

The reaction has been carried out with different volumes of Acetone to determine the preferred solvent quantity. The following experiments have been conducted and the results are tabulated below:

| S. No. | Input (g) | Solvent Volume (mL per g) | Output (g) | Remarks |
|---|---|---|---|---|
| 1 | 5.0 | 20 | 4.0 | Level of 5α = 8.0% |
| 2 | 0.5 | 22 | 0.4 | Level of 5α = 7.4% |
| 3 | 10.0 | 24 | 8.5 | Level of 5α = 8.5% |
| 4 | 150.0 | 24 | 129 | Level of 5α = 8.5% |

Remarks:

Yields and quality of the product are similar at all concentrations.

The quality of the product was monitored by HPLC (RI detection), NMR and MASS.

Conclusion:

Since the yield and product quality were essentially the same at all concentrations, 24 mL/g was chosen as this would be the most productive, less volume also starting material not soluble.

Reaction Time

The following experiments have been conducted to determine the most suitable reaction time and the results are tabulated below.

| S. No. | Input | Time | Output | Remarks |
|---|---|---|---|---|
| 1 | 10 g | 5 hr | 8.63 g | 25 was completely consumed |
| 2 | 10 g | 12 hr | 8.32 g | 25 was completely consumed |
| 3 | 0.3 g | 3 hr | — | 25 was not completely consumed |
| 4 | 50 g | 5 hr | 43.3 g | 25 was completely consumed |

Conclusion:
Based on the experimental results, the reaction time was set at 4-5 h (at 25-35° C.).

Catalyst Quantity

In order to modify the Pd/C quantity, the following experiments have been conducted and experimental results are tabulated below. The catalyst used in every case was 50% Wet palladium-on-carbon.

| S. No. | Exp. No. | Batch Size (g) | Catalyst Qty (g) | Output (g) | Remarks |
|---|---|---|---|---|---|
| 1 | BDA-09-004-I-024 | 0.3 | 0.021 (7%) | — | 25 was not completely consumed |
| 2 | BDA-09-004-I-025 | 1.0 | 0.1 (10%) | 0.9 | 25 was completely consumed |
| 3 | BDA-09-004-I-026 | 0.3 | 0.036 (12%) | 0.9 | 25 was completely consumed |
| 4 | BDA-09-005-I-03 | 0.3 | 0.024 (8%) | 0.25 | 25 was completely consumed |

Remarks:

When the experiments are conducted with 7 wt % of catalyst, the reaction was incomplete even after 5 h of reaction time.

Conclusion:

At least 8% by weight of catalyst should be used to reliably obtain complete consumption of the starting material.

Final Modified Process for Step 1:

The final modified process for this step is given below.

Raw Material Input Details:

| S.No. | Raw materials | Qty. | Unit | M. Wt. | Moles | Mole ratio |
|---|---|---|---|---|---|---|
| 1 | 9α-Hydroxyandrost-4-ene-3,17-dione | 150.0 | g | 302 | 0.496 | 1.0 |
| 2 | 10% Pd/C (50% wet) | 12.0 | g | — | — | 8 wt % |
| 3 | Acetone | 4050 | mL | — | — | 27.0 V |
| 4 | Dichloromethane | 1500 | mL | — | — | 15 V |
| 5 | CELITE | 20 | g | — | — | — |

Experimental Procedure:

To a solution of 9α-Hydroxyandrost-4-ene-3,17-dione (150.0 g) in Acetone (3600 mL) was added 10% of Pd/C (12 g, 8 wt %, 50% wet) and the resulting slurry was hydrogenated in autoclave (50 psi) for 5 h at 25-25° C. Upon complete disappearance of the starting material, as evidenced by TLC (30% EtOAc in DCM), the crude reaction mixture was filtered through a CELITE® bed (20 g) and washed with dichloromethane (1500 mL). The filtrate was removed under vacuum and the crude product (145.0 g) was obtained as a white solid. This crude product was combined with (145.0 g) acetone (300 mL.) at 0° C., stirred for 1 h, then filtered and washed with chilled acetone (150 mL) and dried under vacuum at 50° C. This provided compound 26 (129 g, 85%) as a white solid.

TLC: p-Anisaldehyde charring. $R_f$ for compound 26=0.48 and $R_f$ for compound 25=0.3. Eluent was 30% EtOAc in DCM.

$^1$H NMR (500 MHz, CDCl$_3$): δ=2.40-2.37 (m, 1H), 2.11-.2.02 (m, 2H), 1.91-1.31 (m, 19H), 0.96 (s, 3H), 0.84 (s, 3H).

$^{13}$C NMR (125 MHz, CDCl$_3$): δ=221.0, 95.7, 80.1, 47.0, 43.6, 38.6, 38.5, 37.1, 35.9, 33.41, 32.9, 32.0, 27.9, 26.9, 21.5, 20.2, 20.0, 12.6.

Mass (m/z)=305.0[M$^+$+1], 322.0 [M$^+$+18].

IR (KBr)=3443, 2938, 1722, 1449, 1331, 1138 cm$^{-1}$.

m.p=213-216° C. (from acetone).

[α]$_D$=+116 (c=1% in CHCl$_3$).

HPLC/RI Purity: 99.0%.

Modification Studies for Step 2

Chemical name of Product: 5β-Androst-9(11)-ene-3,17-dione

Synthetic Scheme:

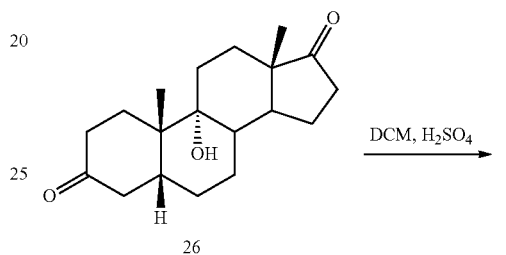

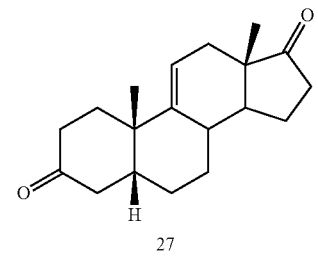

Modification plan for Step 2

Selection of reagent

Selection of Reagent

The following experiments have been conducted and the results are tabulated below.

| S. No. | Batch Size (g) | Reagent | Output (g) | Remarks |
|---|---|---|---|---|
| 1 | 0.1 | Resin (H+) | — | compound 26 was not completed |
| 2 | 0.1 | Resin (H+) | — | compound 26 was not completed |
| 3 | 0.2 | Resin (H+) | — | compound 26 was not completed |
| 4 | 108 | H$_2$SO$_4$ | — | compound 26 was completed |
| 5 | 0.2 | H$_3$PO$_4$ | — | compound 26 was not completed |
| 6 | 0.2 | 25% Aq H$_2$SO$_4$ | — | compound 26 was completed |

Conclusion:

sulfuric acid was chosen as the preferred reagent for elimination, in acidic resin reaction was not completed.

Final modified process for Step 2:

The final modified process for this step is given below:

Ref. Exp. No: BDA-09-008-II-02

| S.No. | Raw materials | Qty. | Unit | M. Wt. | Mole | Mole ratio |
|---|---|---|---|---|---|---|
| 1 | compound 26 | 121 | g | 304 | 0.3979 | 1.0 |
| 2 | Sulfuric acid | 19.1 | mL | 98 | 0.3579 | 0.9 |
| 3 | Dichloromethane | 1815 | mL | — | — | 15 V |
| 4 | Water | 800 | mL | — | — | 6.6 V |
| 5 | Sodium bicarbonate | 600 | mL | — | — | 5.0 V |
| 6 | Brine solution | 200 | mL | — | — | 1.65 V |

Experimental Procedure:

To a solution of compound 26 (121 g) in DCM (1815 mL) was added sulfuric acid (19.1 mL) over 15 minutes under an inert atmosphere at 5-10° C. The temperature was raised to 25-35° C., and the mixture was stirred for 2 h. At this point the reaction was determined to be complete (TLC, 30% EtOAc in DCM). The mixture was washed with water (600 mL) and then washed with 10% aqueous NaHCO$_3$ solution (600 mL). The organic layer was again washed with water (200 mL) followed by saturated brine solution (200 mL). The solvent was then distilled under vacuum, providing compound 27 (108.2 g, 95%) as an off-white solid. The crude product was used in the next step without further purification.

TLC: p-Anisaldehyde charring, R$_f$ for compound 27=0.76 and R$_f$ for compound 25=0.44. Eluent was 30% EtOAc in DCM.

$^1$H NMR (500 MHz, CDCl$_3$): δ=5.61 (s, 1H), 2.57-2.47 (m, 2H), 2.42-2.24 (m, 4H), 2.20-2.05 (m, 3H), 1.99-1.86 (m, 2H), 1.85-1.84 (d, J=6 Hz 1H), 1.63-1.57 (m, 5H), 1.40-1.37 (d, J=13.5 Hz, 1H) 1.28-1.25 (dd, J=4.0, 13.5 Hz, 1H), 1.17 (s, 3H) 0.85 (s, 3H).

$^{13}$C NMR (125 MHz, CDCl$_3$): δ=221.3, 212.8, 140.1, 118.5, 48.5, 45.9, 44.3, 43.5, 39.0, 38.0, 37.3, 36.1, 35.8, 33.3, 28.8, 26.0, 25.5, 22.5, 13.9.

Mass (m/z)=287 [M$^+$+1], 304 [M$^+$+18].

IR (KBr)=3450, 2913, 1737, 1707, 1413, 1403, 1207 cm$^{-1}$.

m.p.=143.4-145.9° C. (from DCM).

[α]$_D$=+142 (c=1% in CHCl$_3$).

HPLC/RI Purity: 96.7%.

Modification Studies for Step 3

Chemical name of product: (Z)-3α-Acetoxy-5β-preg-9(11), 17(20)-diene (compound 30)

Synthetic Scheme:

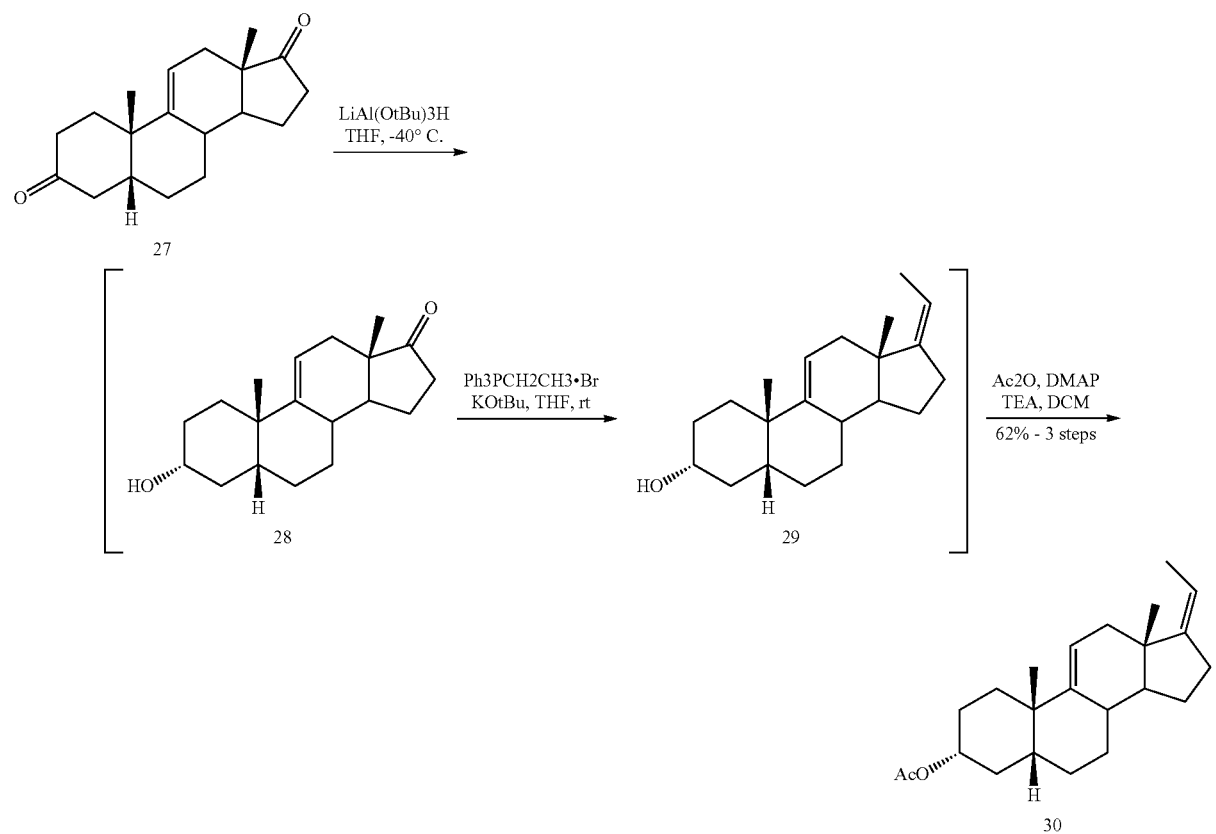

Final Modified Process for Step 3:

The final modified procedure for this step is given below:

Modification Plan for Step 3

Solvent quantity

Solvent Quantity

In order to evaluate the MTBE solvent quantity, the following experiments have been conducted and the results are tabulated below.

| S. No. | Batch Size (g) | Solvent Quantity | Output (g) | Remarks |
|---|---|---|---|---|
| 1 | 10.4 | 104 mL | 6.8 | 10 volume reaction was completed |
| 2 | 10.4 | 156 mL | 6.7 | 15 volume reaction was completed |
| 3 | 43.5 | 528 mL | 29 | 12 volume reaction was completed |

Conclusion:

This reaction works equally well at 12 mL of solvent per gram of substrate. Because of the greater throughput at 12 mL per gram, this was selected as the preferred amount.

Purification Solvent Selection:

Several solvent systems were explored for this final purification. They are:

Methanol
Aqueous Methanol
Ethanol
Isopropyl alcohol
Acetone

The following experiments have been conducted and the experimental results are tabulated below.

| S. No. | Batch Size (g) | Solvent Quantity | Output (g) | Purity by HPLC |
|---|---|---|---|---|
| 1 | 10.4 | Methanol | 6.8 | 95.8% HPLC purity by RI detection |
| 2 | 2.0 | 1% Aq methanol | 1.3 | 94% HPLC purity by RI detection |
| 3 | 2.0 | 2% Aq methanol | 1.39 | 96% HPLC purity by RI detection |
| 4 | 2.0 | IPA | 0.81 | 80.3% HPLC purity by RI detection |
| 5 | 2.0 | Ethanol | 0.9 | 97% HPLC purity by RI detection |
| 6 | 2.0 | Acetone | 0.36 | 97% HPLC purity by RI detection |
| 7 | 5.0 | 2% Aq methanol | 3.68 | 94.3% HPLC purity by RI detection |
| 8 | 11.0 | 2% Aq methanol | 8.2 | 95% HPLC purity by RI detection |

Conclusion:

Extremely effective purification, purity and yield were achieved by crystallization of the product from 2% Aq methanol.

Solvent Quantity

Experiments have been conducted using different solvent volumes and the experimental results are tabulated below.

| S.No. | Batch Size (g) | Solvent quantity | Output (g) | Purity by HPLC |
|---|---|---|---|---|
| 1 | 2.0 | 2 vol | 1.3 | 94% HPLC purity by RI detection |
| 2 | 5.0 | 4 vol | 3.45 | 97.4% HPLC purity by RI detection |
| 3 | 11.0 | 4 vol | 8.2 | 95.1% HPLC purity by RI detection |

Conclusion:

Excellent recoveries and product quality were seen at all solvent levels, so 4 volumes were selected as this is the most productive.

Isolation Temperature

The following experiments have been conducted by varying the isolation temperature and the results are tabulated below

| S.No. | Batch Size (g) | Temp (° C.) | Output (g) | Remarks |
|---|---|---|---|---|
| 1 | 5.0 | 25-30 | 3.68 | 95% HPLC purity by RI detection |
| 2 | 11.0 | 15-20 | 8.2 | 95.1% HPLC purity by RI detection |
| 3 | 11.0 | 10-15 | 8.3 | 94% HPLC purity by RI detection |
| 4 | 11.0 | 15-20 | 8.2 | 95% HPLC purity by RI detection |

Conclusion:

Isolation of the product at 15-20° C., provided good quality and yield.

Final Modified Process for Step 3:

The final modified procedure for this step is given below:

| S.No. | Raw material | Qty | Unit | M. Wt. | Mole | Mole ratio |
|---|---|---|---|---|---|---|
| 1 | compound 27 | 108 | g | 286 | 0.377 | 1.0 |
| 2 | Lithium tri-tert-butoxyaluminum hydride | 700 | mL | — | 0.489 | 1.3 |
| 3 | THF | 1080 | mL | — | — | 10 V |
| 4 | Dichloromethane | 648 | mL | — | — | 10 V |
| 5 | Water | 648 | mL | — | — | 6.0 V |
| 6 | 2N HCl | 648 | mL | — | — | 6.0 V |
| 7 | Brine solution | 540 | mL | — | — | 5.0 V |
| 8 | THF | 756 | mL | — | — | 7.0 V |
| 9 | Potassium tert-butoxide (1.0M in THF) | 1086 | mL | — | 1.085 | 3.0 |
| 10 | Ethyltriphenylphosphonium bromide | 417 | g | 371.26 | 1.12 | 2.9 |
| 11 | MTBE | 4104 | mL | — | — | 38 V |
| 12 | Water | 1080 | mL | — | — | 10 V |
| 13 | Brine solution | 540 | mL | — | — | 5 V |
| 14 | Acetic anhydride | 53.5 | mL | 102 | 0.566 | 1.5 |
| 15 | MTBE | 216 | mL | — | — | 2 V |
| 16 | Triethylamine | 105.2 | mL | 101 | 0.755 | 2.0 |
| 17 | 4-(N,N-Dimethyl-amino)pyridine | 4.6 | g | 122 | 0.037 | 0.1 |
| 18 | Water | 1080 | mL | — | — | 10 V |
| 19 | Brine solution | 324 | mL | — | — | 3 V |

Experimental Procedure:

To a solution of compound 27 (108.0 g) in THF (1080 mL) was added lithium tri-tert-butoxyaluminum hydride (700 mL) at −40 to −45° C. under an inert atmosphere. The resulting reaction mixture was stirred for 2 h at −40 to −45° C. Upon completion of the reaction, as evidenced by TLC (30% EtOAc in DCM), the reaction mixture was quenched by the addition of 2N HCl solution. The phases were separated and the resulting aqueous layer was extracted with dichloromethane (648 mL). The organic fractions were combined and washed with water (648 mL), followed by saturated brine solution (540 mL). The organic layer was evaporated under vacuum which afforded compound 28, dissolved in THF (540 mL).

To a solution of ethyltriphenylphosphonium bromide (417 g) in THF (216 mL) was added potassium tert-butoxide (1086 mL, 1 M solution in THF) drop wise over 20 min under nitrogen at 25-35° C. The resulting dark red reaction mixture was stirred for an additional 1 h at the same temperature. The above solution of compound 28 was added slowly in 30-40 minutes to the above suspension at 25-35° C. The reaction mixture was stirred for an additional 3-5 h, leading to complete consumption of the starting material (as evidenced by TLC; 30% EtOAc in DCM). The reaction mixture was quenched with into ice water (1.080 L). The aqueous layer was extracted with MTBE (2×540 mL) and the combined organic extracts were washed with saturated brine solution (540 mL) organic layer was concentrated under vacuum and the crude material was purified by using MTBE (2×540 mL) filtered, take filtrate distilled off solvent 25% under vacuum. To a solution of compound 29 was cool to 25° C. added triethylamine (105.2 mL), DMAP (4.5 g) and acetic anhydride (53.5 mL) at 25-35° C. under nitrogen. After stirring for 2 hr at 25-35° C., the reaction was determined to be complete by TLC (10% EtOAc in hexanes). The reaction mixture was washed with water (1080 mL) followed by brine solution (324 mL). The organic layer was concentrated under vacuum to afford crude compound 30 (225 g), the residue was re-crystallized in 2% aq methanol provided 85 g of pure compound 30 (63.5% yield with 96% HPLC-RI purity).

TLC: p-Anisaldehyde charring, $R_f$ for compound 30=0.5 and $R_f$ for compound 29=0.15. Eluent=10% EtOAc in hexanes.

$^1$H NMR (500 MHz, $CDCl_3$): δ=5.38 (s, 1H), 5.20-5.18 (d, J=6.5 Hz, 1H), 4.76-4.72 (m, 1H), 2.40-2.35 (m, 3H), 2.25-2.22 (m, 1H), 2.09-2.03 (m, 3H), 2.01 (s, 3H), 1.98-1.49 (m, 10H), 1.41-1.31 (m, 2H), 1.27-1.16 (m, 3H), 1.07 (s, 3H), 0.79 (s, 3H).

$^{13}$C NMR (125 MHz, $CDCl_3$): δ=170.5, 150.0, 140.4, 119.6, 114.3, 74.7, 53.5, 42.0, 41.7, 39.6, 38.6, 35.6, 35.3, 33.8, 31.9, 29.5, 27.8, 26.7, 26.6, 25.5, 21.3, 16.9, 13.2

Mass (m/z)=342.9 [M$^+$+1], 360 [M$^+$+18].

IR ($CHCl_3$)=3440, 3035, 1730, 1451, 1367, 1258, 1028 cm$^{-1}$.

Mp=93.9-97.8° C.

$[α]_D$=+109 (c=1% in $CHCl_3$).

HPLC/RI Purity: 96.0%.

Modification Studies for Step 4

Chemical name of product: Methyl 3α-acetoxy-5β-chola-9(11), 16-dien-24-oate (compound 84)

Synthetic Scheme:

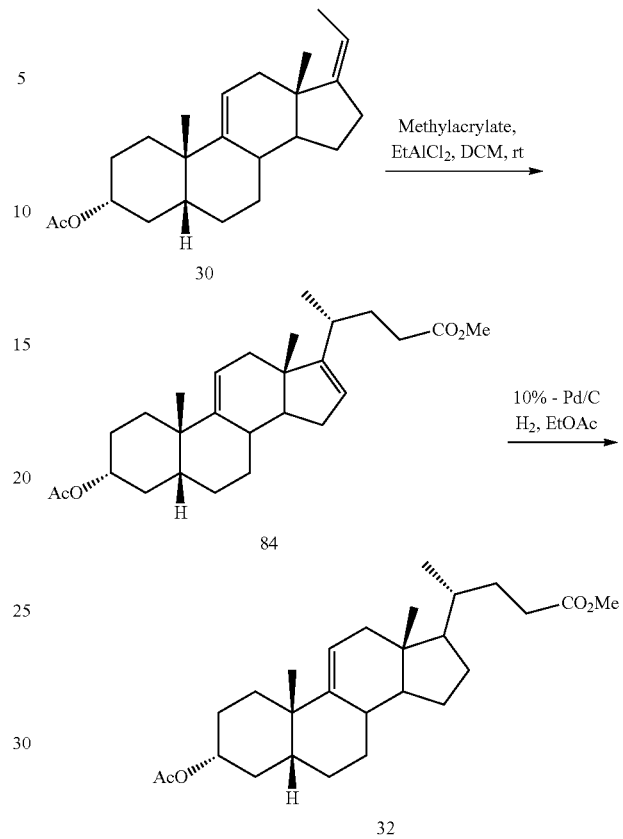

Modification Plan for Step 6
  Selection of Lewis Acid
  Lewis Acid Quantity
  Catalyst selection
  Catalyst Quantity
Selection of Lewis Acid In order to examine alternative Lewis acids as a catalyst in this step, the following experiments have been conducted and the results are tabulated below:

| S.No. | Batch Size(g) | Reagent | Output (g) | Remarks |
|---|---|---|---|---|
| 1 | 0.1 | $SnCl_4$ | — | No reaction-only is starting material. |
| 2 | 0.1 | $ZnCl_2$ | — | No reaction-only is starting material. |
| 3 | 0.3 | $SnCl_4$ | — | No reaction-only is starting material. |

Lewis Acid Quantity:

Ethyl aluminum dichloride was found to be effective for this step. We studied mole ratios of ethyl aluminum dichloride and the results are tabulated below:

| S.No. | Batch Size(g) | Lewis acid (Equiv) | Output (g) | Remarks |
|---|---|---|---|---|
| 1 | 0.2 | 2.0 | — | Observed 10% of starting material. |
| 2 | 0.2 | 2.5 | — | Observed 10% of starting material. |
| 3 | 27 | 3.0 | 30.0 | Observed absence of starting material. |

Conclusion:

Reaction worked well with 3.0 equiv of Ethyl aluminum dichloride.

Catalyst Selection

Platinum oxide had been used initially as a catalyst in this step. Palladium-on-carbon is less expensive and is also a typical hydrogenation catalyst, so this was also explored. The following experiments have been conducted and the results are tabulated below:

| S.No. | Batch Size(g) | Catalyst | Output (g) | Remarks |
|---|---|---|---|---|
| 1 | 2.0 | Pd/C (50% wet) | — | Reaction was completed. |
| 2 | 5.0 | Pd/C (50% wet) | — | Reaction was not completed. |
| 3 | 43.0 | Pd/C (dry) | 45.0 | Reaction was completed. |

Conclusion:

50% wet palladium/carbon worked on small scale in ethyl acetate media, using commercial dry palladium catalyst.

Final Modification Process for Step 4:

The final medication procedure for this step is given below:

| S.No. | Raw Material | Qty | Unit | M. Wt. | Mole | Mole ratio |
|---|---|---|---|---|---|---|
| 1 | compound 30 | 56 | g | 342 | 0.163 | 1.0 |
| 2 | Dichloromethane | 1120 | mL | — | — | 20 V |
| 3 | Methyl acrylate | 35.13 | mL | 86 | 0.389 | 2.38 |
| 4 | Ethyl aluminum dichloride (1.8M in toluene) | 272.9 | mL | — | 0.491 | 3.0 |
| 5 | Water | 1680 | mL | — | — | 30 V |
| 6 | Brine solution | 560 | mL | — | — | 10 V |
| 7 | Methanol | 336 | mL | — | — | 6.0 V |
| 8 | Ethyl acetate | 1650 | mL | — | — | 29.5 V |
| 9 | 10% Palladium on carbon | 6.7 | g | — | — | 12 wt % |
| 10 | CELITE | 25 | g | — | — | — |

Experimental Procedure:

To a solution of compound 30 (56 g) in DCM (560 mL) was added methyl acrylate (35.13 mL) at 0-5° C. under an inert atmosphere stirring for 60 min, solution was cool to 0-5° C., ethylaluminum dichloride (272.9 mL; 1.8 M in toluene), was added over period of 60 min. The temperature was then raised to 25-35° C. and the mixture was stirred for ~18 hr. At this point analysis by TLC (10% EtOAc in hexanes) showed the reaction to be complete, so the mixture was poured into ice cold water (1120 mL). The phases were separated and the aqueous layer was extracted with DCM (2×255 mL). The organic layers were combined and washed sequentially with water (560 mL) and brine solution (560 mL), the organic layer was evaporated under vacuum, which provided compound 84 (66 g) as an oil.

To a solution of compound 84 in ethyl acetate (550 mL), Pd/C (6.7 g) slurry in ethyl acetate (110 mL) was added at 25-35° C. The resulting slurry was stirred under −70 psi hydrogen pressure for ~16 h. The progress of the reaction was monitored by HPLC. The catalyst was filtered on a CELITE® bed (25 g) and the cake was washed with ethyl acetate (990 mL). The filtrate was evaporated under vacuum, which provided compound 32 (59 g, 85%) as a solid.

TLC: p-Anisaldehyde charring, $R_f$ for compound 32=0.32 and $R_f$ for compound 84=0.30 Eluent=10% EtOAc in hexanes.

$^1$H NMR (500 MHz, CDCl$_3$): δ=5.31 (s, 1H), 4.73 (m, 1H), 3.66 (s, 3H), 2.37-2.03 (m, 7H), 2.01 (s, 3H), 1.98-1.09 (m, 18H), 1.06 (s, 3H), 0.92-0.91 (d, J=6.0 Hz, 3H), 0.59 (s, 3H).

$^{13}$C NMR (125 MHz, CDCl$_3$): δ=174.6, 170.5, 139.8, 119.5, 74.8, 56.0, 53.3, 51.4, 41.9, 41.7, 40.9, 38.5, 36.4, 35.4, 35.2, 33.8, 31.0, 30.9, 29.5, 28.2, 27.8, 26.8, 26.7, 25.2, 21.4, 17.9, 11.5

Mass (m/z)=448.2 [M$^+$+18].

IR (KBr)=3435, 3039, 2941, 1729, 1448, 1435, 1252, 1022 cm$^{-1}$.

m.p.=122.1-123.9° C.

[α]$_D$=+56 (c=1% in CHCl$_3$).

HPLC/RI Purity: 93.0%.

Modification Study for Step 5

Chemical name of product: Methyl 3α-acetoxy-12-oxo-5β-chol-9(11)-en-24-oate (compound 24)

Synthetic Scheme:

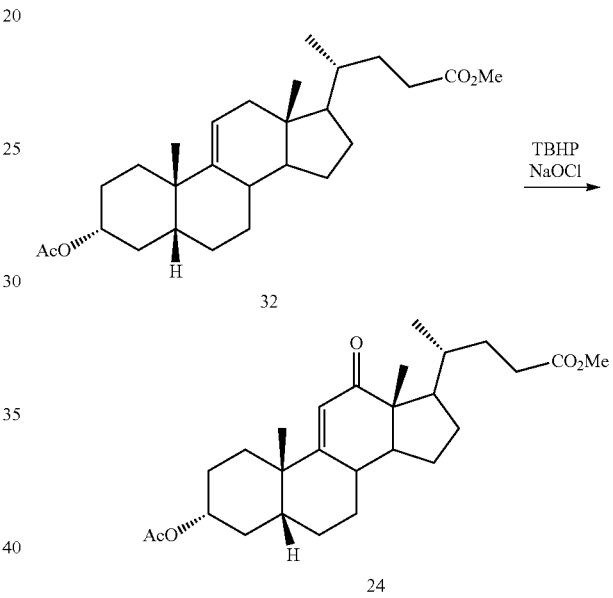

Modification Plan for Step 8
  Selection of reagent
  Reagent stoichiometry
  Solvent selection
  Solvent quantity
  Reaction temperature
  Reaction time
  Product isolation solvent
  Product recrystalisation
Reagent Selection The reaction was tried with a large number of alternative oxidizing agents. The following experiments were conducted and the results are tabulated below.

| S.No. | Batch Size(g) | Reagent | Output (g) | Remarks |
|---|---|---|---|---|
| 1 | 0.5 | NBS | — | Reaction was not completed. |
| 2 | 0.2 | Br$_2$ | — | Reaction was not completed. |
| 3 | 0.2 | DDHT | — | Reaction was not completed. |
| 4 | 0.2 | HBr | — | Reaction was not completed. |
| 5 | 1.0 | DDHT/AIBN | — | Reaction was not completed. |
| 6 | 0.1 | NBS/ Benzoylperoxide | — | Reaction was not completed. |

-continued

| S.No. | Batch Size(g) | Reagent | Output (g) | Remarks |
|---|---|---|---|---|
| 7 | 0.1 | DDHT/Benzoylperoxide | — | Reaction was not completed. |
| 8 | 0.2 | $SeO_2$/NMO | — | Reaction was not completed. |
| 9 | 0.2 | $SeO_2$/TBHP | — | Reaction was not completed. |
| 10 | 0.1 | $SeO_2$ | — | Reaction was not completed. |
| 11 | 0.1 | $Br_2$/AcOH | — | Reaction was not completed. |
| 12 | 0.1 | $Br_2$/AcOH | — | Reaction was not completed. |
| 13 | 0.2 | $CrO_3$/Pyridine | — | Reaction was not completed. |
| 14 | 0.1 | 6% Aq $CrO_3$ | — | Reaction was completed. |
| 15 | 0.2 | $CrO_3$/DMP | — | Reaction was not completed. |
| 16 | 0.5 | TBHP,CuI/NaOCl | — | Reaction was not completed. |
| 17 | 2.0 | TBHP/NaOCl | — | Reaction was completed. |
| 18 | 5.0 | TBHP/NaOCl | 2.0 | Reaction was completed. |
| 19 | 0.2 | $CrO_3$/Styrene | — | Reaction was not completed. |
| 20 | 0.2 | $CrO_3$/DMB | — | Reaction was not completed. |
| 21 | 1.0 | TBHP/NaOCl | 0.4 | Reaction was completed. |
| 22 | 2.0 | TBHP/NaOCl | 0.8 | Reaction was completed. |
| 23 | 10.0 | TBHP/NaOCl | 4.5 | Reaction was completed. |
| 24 | 5.0 | TBHP/$Ca(OCl)_2$ | 4.5 | Reaction was completed. |
| 25 | 20.0 | TBHP/NaOCl | 13.0 | Reaction was completed. |
| 26 | 20.0 | TBHP/NaOCl | 12.8 | Reaction was completed. |

Note: DDHT:Dibromo dimethylhydantoin, DMP: Dimethylpyrazole, DMB: 3,3-Dimethyl 1-butene
TBHP—tert-Butyl hydro peroxide Several other reagents such as CrO3/TBHP, NaClO2/TBHP, and the like were also tried.

Conclusion:

As to TBHP/NaOCl, it is noted that the alternative oxidants other than chromium trioxide did not work well. Accordingly, TBHP/NaOCl were selected as the oxidizing reagent.

Solvent Selection

During the runs of this step, acetic acid was used as solvent. The following solvents were selected as alternatives and the results were compared.
Dichloromethane
Ethyl acetate
Water Numerous other solvents have been tried with the different oxidation conditions. Some of the other solvents are ACN, acetone, and AcOH but others could be incorporated.

The following experiments were conducted and the results are tabulated below.

| S.No. | Batch Size (g) | Solvent | Output (g) | Remarks |
|---|---|---|---|---|
| 1 | 1.0 | DCM | — | Starting material was not consumed |
| 2 | 0.5 | Water | — | Starting material was not consumed |
| 3 | 1.0 | EtOAc | 0.4 | Reaction was completed. |
| 4 | 2.0 | EtOAc | 0.8 | Reaction was completed. |

Conclusion:

The results were better when EtOAc was used as the solvent as compared to DCM. Therefore, ethyl acetate was chosen as the preferred solvent.

Solvent Quantity 20 volumes of Ethyl acetate were used in the initial runs of this step. The following experiments were conducted to see if less solvent could be used. The results are tabulated below.

| S.No. | Batch Size (g) | Solvent Quantity | Solvent Ratio | Output (g) | Remarks |
|---|---|---|---|---|---|
| 1 | 2.0 | 10 mL | 5 V | 0.8 | Reaction was completed |
| 2 | 10.0 | 200 mL | 20 V | 4.5 | Reaction was completed |
| 3 | 20.0 | 200 mL | 10 V | 13.0 | Reaction was completed |
| 4 | 20.0 | 200 mL | 10 V | 12.8 | Reaction was completed |

Conclusion:

10 volumes of solvent were chosen as the preferred amount.

Reagent Stoichiometry

The initial runs of this step were carried out with less equivalents of TBHP. The following experiments have been conducted to modify this amount of this reagent and results are tabulated below.

| S.No. | Batch Size(g) | Mole Ratio | Output (g) | Remarks |
|---|---|---|---|---|
| 1 | 0.2 | 10 | — | Reaction was not completed |
| 2 | 1.0 | 20 | — | Reaction was not completed |
| 3 | 1.0 | 25 | — | Reaction was not completed |
| 4 | 1.0 | 30 | — | Reaction was not completed |
| 5 | 20.0 | 34 | 13.0 | Reaction was completed |
| 6 | 20.0 | 34 | 12.8 | Reaction was completed |

Conclusion:

The reaction went to completion with 34 equivalents of reagent, but was incomplete in the two experiments where less was used. Therefore, 34 equivalents were selected as the preferred amount.

Reagent Stoichiometry

The initial runs of this step were carried out with less equivalents of NaOCl. The following experiments have been conducted to modify this amount of this reagent and results are tabulated below.

| S.No. | Batch Size(g) | Mole Ratio | Output (g) | Remarks |
|---|---|---|---|---|
| 1 | 1.0 | 3.0 | — | Reaction was not completed |
| 2 | 0.2 | 5.0 | — | Reaction was not completed |
| 3 | 5.0 | 5.0 | — | Reaction was not completed |
| 4 | 1.0 | 10.0 | 0.4 | Reaction was completed |
| 5 | 5.0 | 7.0 | 2.0 | Reaction was not completed |
| 6 | 5.0 | 7.0 | 2.2 | Reaction was not completed |

Conclusion:

The reaction went to completion with 7.0 equivalents of reagent, but was incomplete in the two experiments where less was used. Therefore, 7.0 equivalents were selected as the preferred amount.

Reaction Temperature

In order to modify the reaction temperature, the following experiments have been conducted and the results are tabulated below.

| S.No. | Batch Size (g) | Temperature | Output (g) | Remarks |
|---|---|---|---|---|
| 1 | 5.0 | 25-30° C. | 2.0 | Reaction was completed |
| 2 | 5.0 | 10-15° C. | 2.2 | Reaction was completed |
| 3 | 20.0 | 0-5° C. | 13.0 | Reaction was completed |
| 4 | 20.0 | 0-5° C. | 12.8 | Reaction was completed |

Conclusion:

The reaction worked at all temperatures between 0 and 5° C., so a range of 0-10° C. was chosen as the reaction is expected to be more selective at lower temperature and the yields were observed to be higher.

Reaction Time

During the initial runs, the reaction was carried out at 0-5° C. (for 24 hr). In order to ascertain whether to modify the reaction time, the following experiments were conducted and the results are tabulated below.

| S.No. | Batch Size (g) | Time. | Output (g) | Remarks |
|---|---|---|---|---|
| 1 | 1.0 | 24 | 0.4 | Reaction was completed |
| 2 | 20.0 | 8.0 | 13.0 | Reaction was completed |
| 3 | 20.0 | 8.0 | 12.8 | Reaction was completed |

Conclusion:

The reaction appears to complete at 0-5° C. in 8 h, so this was chosen as the preferred reaction time.

Product isolation Solvent Selection:

Two solvent systems were explored for this final purification. They are:

Methanol

Aqueous Methanol

The following experiments have been conducted and the experimental results are tabulated below.

| S.No. | Experiment Number | Batch Size (g) | Solvent | Output (g) | Purity by HPLC |
|---|---|---|---|---|---|
| 1 | BDA-09-009-V-05 | 20.0 | Methanol | 10.0 | 95.6% HPLC purity by RI detection |
| 2 | BDA-09-009-V-017 | 50.0 | 20% Aq methanol | 31.9 | 95.2% HPLC purity by RI detection |
| 3 | BDA-10-003-V-01 | 60.0 | 20% Aq methanol | 38.0 | 91.2% HPLC purity by RI detection |
| 4 | BDA-10-003-V-06A | 13.0 | 30% Aq methanol | 10.5 | 81.8% HPLC purity by RI detection |
| 5 | BDA-10-003-V-06B | 13.0 | 40% Aq methanol | 11.0 | 80.3% HPLC purity by RI detection |
| 6 | BDA-10-003-V-06C | 13.0 | 50% Aq methanol | 11.0 | 80.4% HPLC purity by RI detection |

Conclusion:

Extremely effective purification, purity & yield were achieved by isolation of the product from 20% Aq methanol. Alternatively, column purification with silica gel and a gradient solvent system (EtOAc/hexanes) is used.

Purification Solvent Selection:

Two solvent systems were explored for this final purification. They are:

Methanol

Aqueous Methanol

The following experiments have been conducted and the experimental results are tabulated below.

| S.No. | Batch Size (g) | Solvent | Output (g) | Purity by HPLC |
|---|---|---|---|---|
| 1 | 10.0 | Methanol | 8.0 | 93.6% HPLC purity by RI detection |
| 2 | 18.0 | 13% Aq methanol | 15.5 | 93.8% HPLC purity by RI detection |
| 3 | 25.0 | Methanol | 10.0 | 91.9% HPLC purity by RI detection |
| 4 | 20.0 | 13% Aq methanol | 17.0 | 93.8% HPLC purity by RI detection |
| 5 | 20.0 | 13% Aq methanol | 17.0 | 93.3% HPLC purity by RI detection |

Conclusion:

Extremely effective purification, purity & yield were achieved by recrystallization of the product from 13% Aq methanol. Alternatively, column purification with silica gel and a gradient solvent system (EtOAc/hexanes) is used.

Final Modified Process for Step 8:

The final modified procedure for this step is given below.

| S. No. | Raw Material | Qty | Unit | M. Wt. | Mole | Mole ratio |
|---|---|---|---|---|---|---|
| 1 | compound 32 | 20.0 | g | 430 | 0.046 | 1.0 |
| 2 | 10% Sodiumhypochlorite | 220 | mL | 74.5 | 0.322 | 7.0 |
| 3 | 70% TBHP in water | 200 | mL | 90 | 1.56 | 34.0 |
| 4 | Ethyl acetate | 300 | mL | — | — | 15 V |
| 5 | Pyridiniumchlorochromate | 10.9 | g | 215.5 | 0.056 | 1.1 |
| 6 | Methanol | 140 | mL | — | — | 7.0 V |
| 7 | Water | 2000 | mL | — | — | 100 V |
| 8 | Brine solution | 100 | mL | — | — | 5.0 V |

Experimental Procedure:

To a solution of compound 32 (20 g) in ethyl acetate (200 mL) was added 70% TBHP in water (200 mL) reaction solution was cool to 0° C., was slowly added 10% Sodium hypochlorite for about 6-7 h at 0-5° C., stir for 2-3 h at same temp. Upon complete disappearance of compound 32 by TLC (eluent=20% EtOAc in hexanes), separate the organic layer and the aqueous layer extracted with ethyl acetate (60 mL). the combined organic layer was washed with water (2×400 mL) followed by treated with 20% sodium sulfite sol (220 mL) at 50-55° C. for 2 h, separate two layers, organic layer was treated with pyridinium chlorochromate (10.9 g) for 6-8 h at 25-30° C. Upon complete disappearance of allylicalcohol by TLC (eluent=20% EtOAc in hexanes), the organic layers were washed with hot water (4×500 mL) followed by saturated brine solution (100 mL). Organic layer was evaporated under vacuum at 45-50° C. The resulting crude material was purified by stirring it with 20% aqueous methanol (40 mL) at 5-10° C. for 1 h filtered; the cake was washed with 20% aqueous methanol (20 mL) and then dried under vacuum at 45-50° C. The organic layer was concentrated and absorbed onto silica (1.5 equiv.). Separately a silica gel (hexanes) column was prepared with 7 equiv. of silica and the resulting product containing mixture was loaded onto the column. The product was then eluted with a hexane/EtOAc gradient mixture to yield column fractions containing compound 24. Each fraction was sampled and tested for purity. All fractions with the desired purity were combined and concentrated in vacuo. The resulting mixture was then precipitated from hexanes and then dried under vacuum at 45-50° C., which provided compound 24 (13 g) as a pale yellow solid.

TLC: p-Anisaldehyde charring, $R_f$ for compound 24=0.28 and $R_f$ for compound 32=0.52. Eluent=20% EtOAc in hexanes.

$^1$H NMR (500 MHz, CDCl$_3$): δ=5.71 (s, 1H), 4.75-4.71 (m, 1H), 3.66 (s, 3H), 2.42-2.37 (m, 3H), 2.31-2.02 (m, 2H), 2.0 (s, 3H), 1.98-1.67 (m, 9H), 1.56-1.24 (m, 9H), 1.19 (s, 3H), 1.02-1.01 (d, J=6.5 Hz, 3H), 0.90 (s, 3H).

$^{13}$C NMR (500 MHz, CDCl$_3$): δ=204.9, 174.5, 170.4, 163.8, 123.6, 73.7, 53.4, 53.0, 51.3, 47.2, 41.7, 39.8, 37.7, 35.2, 35.0, 33.9, 31.4, 30.5, 29.6, 27.6, 27.3, 26.4, 26.1, 24.1, 21.2, 19.4, 10.6.

Mass (m/z)=445.0 [M$^+$+1], 462.0 [M$^+$+18].

IR=3437, 3045, 2946, 2870, 1729, 1680, 1252, 1168, 1020, cm$^{-1}$.

m.p.=141-142° C.

[α]$_D$=+102 (c=1% in CHCl$_3$).

HPLC/RI Purity: 96.2%.

Scheme 3 - The Final Synthesis from 25

SUMMARY
Stage-I: 9α-Hydroxy-5β-androstane-3,17-dione
Stage-II: 5β-Androst-9(11)-ene 3,17-dione
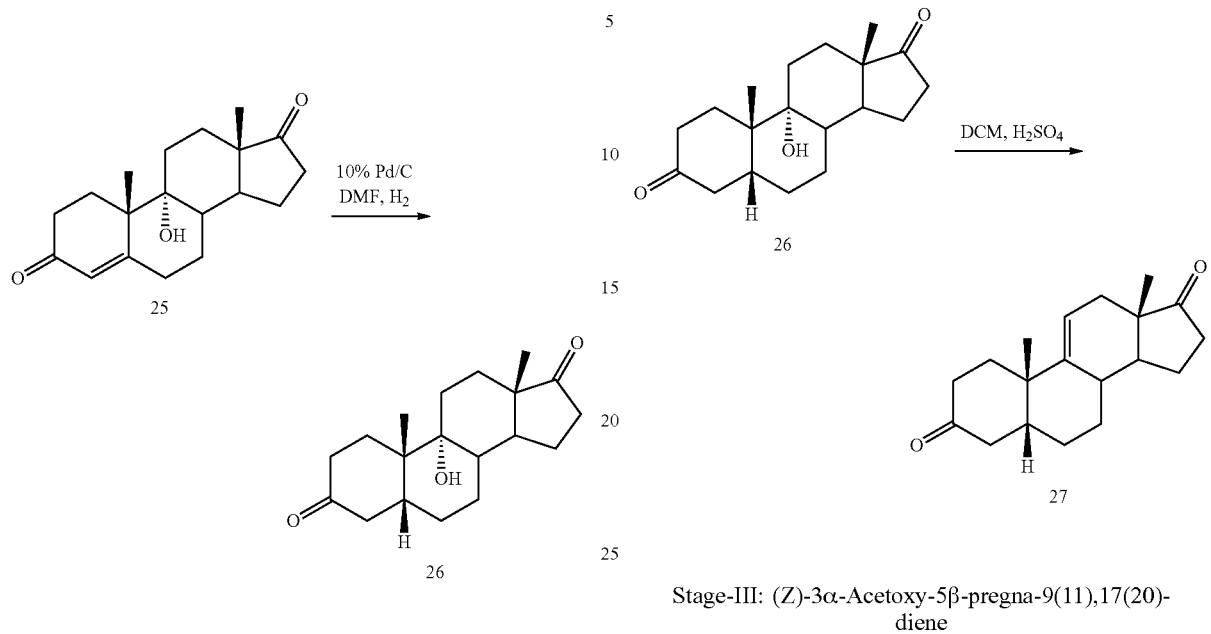
Stage-III: (Z)-3α-Acetoxy-5β-pregna-9(11),17(20)-diene
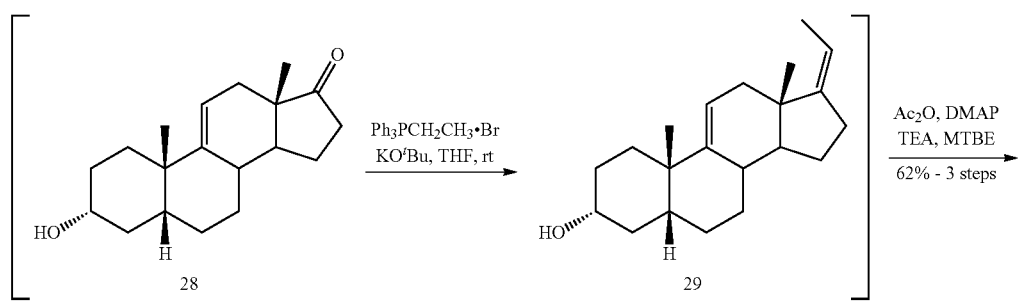
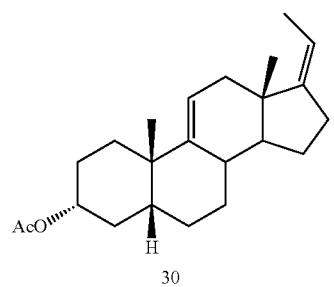

Stage-IV: Methyl 3α-acetoxy-5β-chol-9(11)-en-24-oate

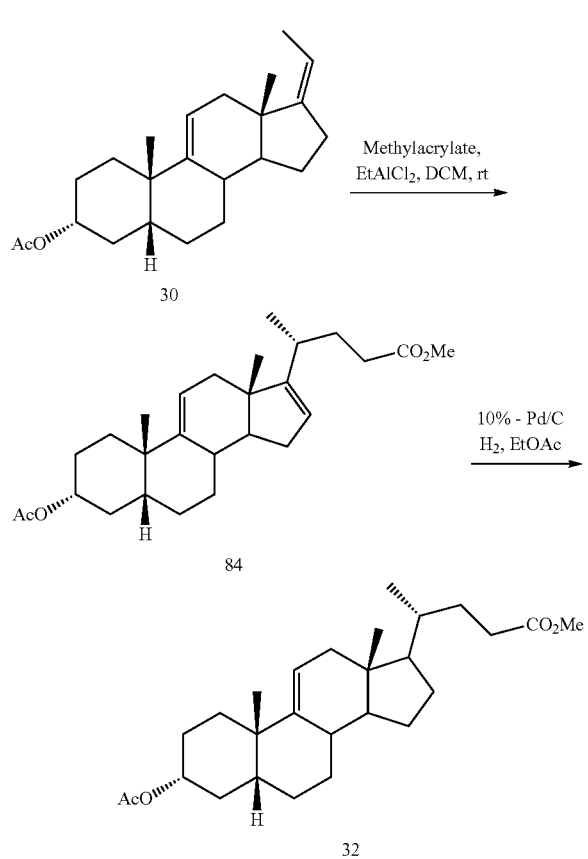

Stage-V: Methyl 3α-acetoxy-12-oxo-5β-chol-9(11)-en-24-oate

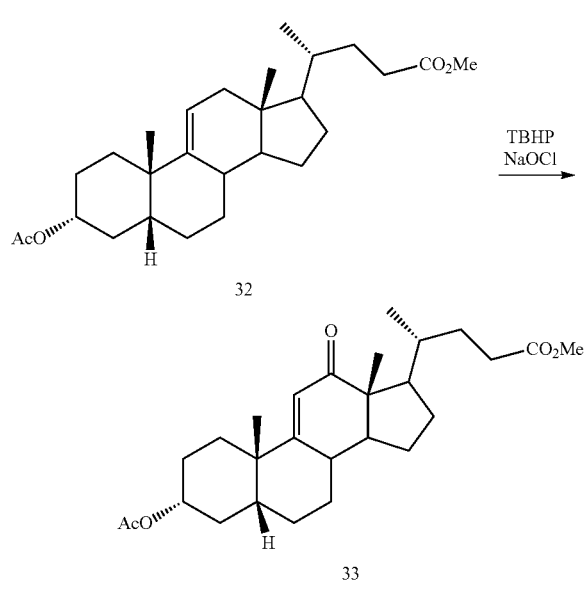

Stage-I: 9α-Hydroxy 5β-androstane-3,17-dione

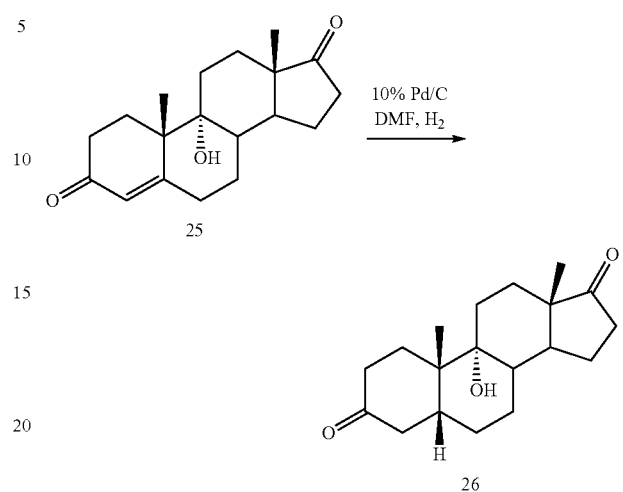

Raw Materials:

| S. No. | Raw Material | Qty | Unit | Mol. Wt. | Mole | Mole Ratio |
|---|---|---|---|---|---|---|
| 1 | 9α-Hydroxyandrostene-dione(9-HAD) | 100.0 | g | 302.4 | 0.330 | 1.0 |
| 2 | 10% Pd/C (wet) | 8.0 | g | — | — | 8.0 wt % |
| 3 | Acetone | 3000 | mL | — | — | 30.0 V |
| 4 | Dichloromethane | 1200 | mL | — | — | 12.0 V |
| 5 | CELITE | 20 | g | — | — | — |

Experimental Procedure:
01. Charge Acetone (2200 mL) into a clean and dry autoclave.
02. Charge 9-HAD (100 g) into the same autoclave.
03. Stir reaction mixture at 25° C. (RT) and add slurry of Pd/C (8.0 g) in acetone (200 mL).
04. After inerting with nitrogen, pressurize with hydrogen gas to 60 psi.
05. Stir the reaction mixture at 25-35° C. (RT) and 60 psi for 4-5 h.
06. Check for completion by HPLC (30% EtOAc in DCM; NMT 0.5% of 25).
07. Dilute the reaction mixture with dichloromethane (300 mL).
08. Filter through a CELITE® bed (20 g) and wash the CELITE® with dichloromethane (900 mL).
09. Concentrate the filtrate via vacuum distillation of all the solvent at below 45° C.
10. Charge acetone (300 mL) and completely remove the solvent under vacuum at below 65° C.
11. Charge acetone (200 mL) and cool to 0-5° C.
12. Maintain the resulting slurry for 2 h at 0-5° C., and then filter.
13. Wash the wet cake with chilled (0-10° C.) acetone (100 mL).
14. Dry the resulting white solid in a hot air oven at 45-50° C. until the LOD is NMT 1%.
Wet weight: 105 g
Dry weight: 86 g
Yield: 85.4%
LOD <1.0%

Melting range: 218-219.7° C.
SOR: +126.4 (c=1% in CHCl₃).
HPLC/RI Purity: 99.0%.
NOTE: Alternative process for Hydrogenation.
Raw materials:

| No. | Raw Material | Qty | Unit | Mol. Wt. | Mole | Mole Ratio |
|---|---|---|---|---|---|---|
| 1 | 9α-Hydroxyandrostenedione (9-HAD) | 100.0 | g | 302 | 0.331 | 1.0 |
| 2 | 10% Pd/C (dry) | 7.0 | g | — | — | 7.0 wt % |
| 3 | N,N-Dimethylformamide | 700 | mL | — | — | 7.0 V |
| 4 | Dichloromethane | 1200 | mL | — | — | 12.0 V |
| 5 | Acetone | 600 | mL | — | — | 6.0 V |
| 6 | CELITE | 20 | g | — | — | — |

Experimental Procedure:
15. Charge DMF (500 mL) into a clean and dry autoclave.
16. Charge 9-HAD (100 g) into the same autoclave.
17. Stir reaction mixture at 25° C. (RT) and add slurry of Pd/C (7.0 g) in DMF (200 mL).
18. After inerting with nitrogen, pressurize with hydrogen gas to 60 psi.
19. Stir the reaction mixture at 25-35° C. (RT) and 60 psi for 3 h.
20. Check for completion by TLC (30% EtOAc in DCM; NMT 2% of 25).
21. Dilute the reaction mixture with dichloromethane (300 mL).
22. Filter through a CELITE® bed (20 g) and wash the CELITE® with dichloromethane (900 mL).
23. Concentrate the filtrate via vacuum distillation of all the solvent at below 65° C.
24. Charge acetone (300 mL) and completely remove the solvent under vacuum at below 65° C.
25. Charge acetone (200 mL) and cool to 0-5° C.
26. Maintain the resulting slurry for 2 h at 0-5° C., and then filter.
27. Wash the wet cake with chilled (0-10° C.) acetone (100 mL).
28. Dry the resulting white solid in a hot air oven at 45-50° C. until the LOD is NMT 1%.
Wet weight: 105 g
Dry weight: 88 g
Yield: 87.4%
LOD <1.0%
Melting range: 218-219.7° C.
SOR: +126.4 (c=1% in CHCl₃)

Stage-II: 5β-Androst-9(11)-ene-3, 17-dione

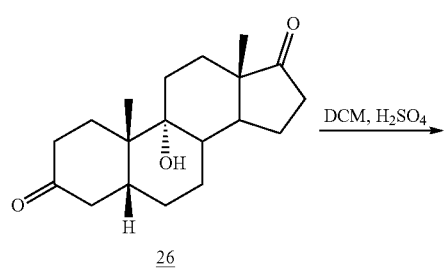

26

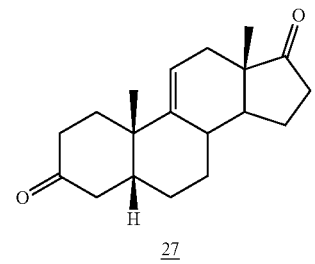

27

Raw Materials:

| S. No. | Raw Material | Qty | Unit | Mol. Wt. | Mole | Mole Ratio |
|---|---|---|---|---|---|---|
| 1 | Stage-I Product | 85.0 | g | 304 | 0.279 | 1.0 |
| 2 | Sulfuric acid | 13.5 | mL | 98 | 0.251 | 0.9 |
| 3 | Dichloromethane | 1530 | mL | — | — | 18.0 V |
| 4 | Hexanes | 340 | mL | — | — | 4 V |
| 5 | Water | 1700 | mL | — | — | 20.0 V |
| 6 | Sodium bicarbonate | 425 | mL | — | — | 5.0 V |
| 7 | Saturated Brine solution | 425 | mL | — | — | 5.0 V |

Experimental Procedure:
01. Charge dichloromethane (1275 mL) and the Stage-I product into a clean and dry flask.
02. Cool the mixture to 10° C. and then add sulfuric acid (13.5 mL) slowly over 15 min at 10-15° C.
03. Reaction solution temp raise to 25-35° C. and stir for 2 h at 25-35° C.
04. Check for completion by TLC (30% EtOAc in DCM; NMT 1% of Stage-I product).
05. Wash the reaction mixture with water (300 mL).
06. Back extract the aqueous layer with DCM (2×212 mL), and then combine the organic layers.
07. Wash the organic layer with saturated sodium bicarbonate solution (425 mL)
08. Wash the organic layer with water (550 mL) followed by brine solution (425 mL).
07. Distill out the solvent completely under vacuum at less than 45° C.
08. Add hexanes (340 mL) and distill out the solvent completely under vacuum at less than 50° C.
09. Add water (616 mL), stir for 15 min at RT, then filter and wash the cake with water (255 mL).
10. Dry the white solid in a hot air drier at 55-60° C. until the moisture content is NMT 0.5%.
Wet weight: ~190 g.
Dry weight: 76 g
Yield: 95%
Moisture <0.5%
Melting range: 148.5-150.1° C.
SOR: +144.4 (c=1% in CHCl₃).
HPLC/RI Purity: 96.0%.

Stage-III: (Z)-3α-Acetoxy-5β-preg-9(11), 17(20)-diene (compound 30)

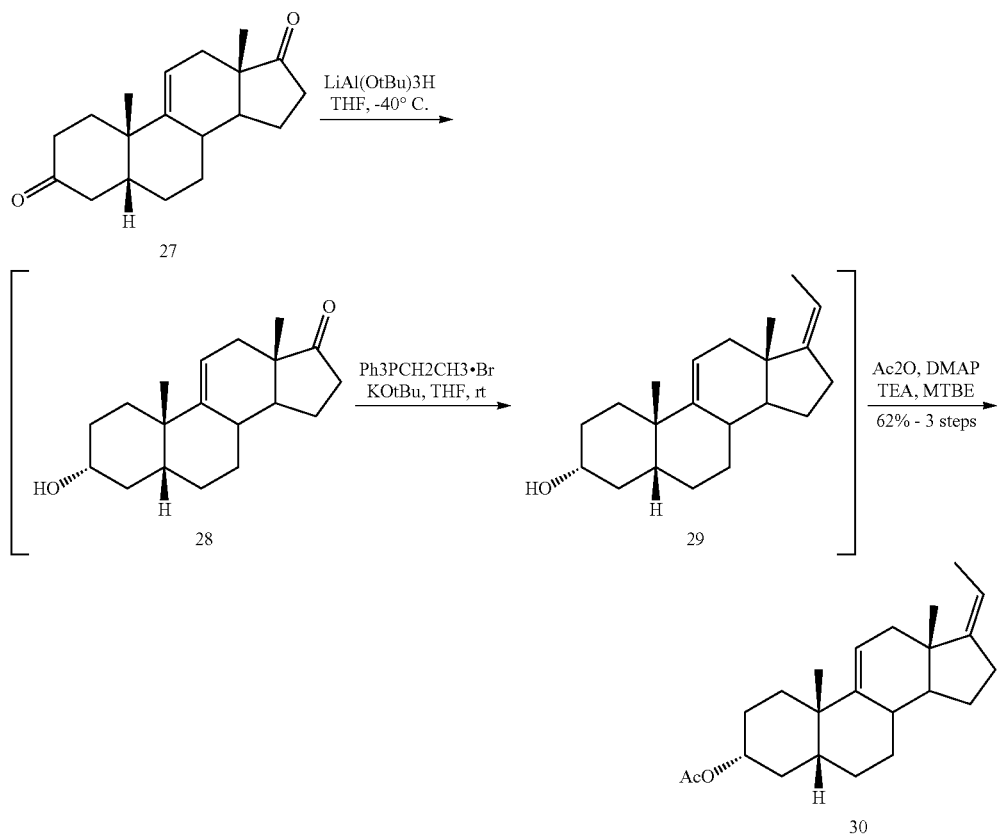

Raw Materials:

| S. No. | Raw material | Qty | Unit | M. Wt. | Mole | Mole ratio |
|---|---|---|---|---|---|---|
| 1 | compound 27 | 76 | g | 286.2 | 0.265 | 1.0 |
| 2 | Lithium tri-tert-butoxyaluminum hydride | 319 | mL | 254.2 | 0.489 | 1.2 |
| 3 | THF | 760 | mL | — | — | 10 V |
| 4 | Dichloromethane | 380 | mL | — | — | 6 V |
| 5 | Water | 456 | mL | — | — | 6.0 V |
| 6 | 2N HCl | 456 | mL | — | — | 6.0 V |
| 7 | Brine solution | 380 | mL | — | — | 5.0 V |
| 8 | THF | 532 | mL | — | — | 8.0 V |
| 9 | Potassium tert-butoxide (1.0M in THF) | 768 | mL | — | 0.797 | 2.9 |
| 10 | Ethyltriphenylphosphonium bromide | 295.4 | g | 371.26 | 0.795 | 3.0 |
| 11 | MTBE | 2280 | mL | — | — | 30 V |
| 12 | Water | 760 | mL | — | — | 10 V |
| 13 | Brine solution | 380 | mL | — | — | 5 V |
| 14 | Acetic anhydride | 37.6 | mL | 102 | 0.398 | 1.5 |
| 15 | MTBE | 216 | mL | — | — | 5 V |
| 16 | Triethylamine | 73.9 | mL | 101 | 0.530 | 2.0 |
| 17 | 4-(N,N-Dimethylamino)pyridine (DMAP) | 3.23 | g | 122 | 0.026 | 0.1 |
| 18 | Water | 796 | mL | — | — | 10 V |
| 19 | Brine solution | 380 | mL | — | — | 5 V |
| 20 | Methanol | 380 | mL | — | — | 5 V |
| 21 | 2% Aqueous methanol | 380 | mL | — | — | 5 V |

Experimental Procedure:

01. Charge dry THF (760 mL) and Stage-II Product (76 g) under nitrogen into a clean and dry flask.
02. Cool to −35 to −45° C. and then add a solution of lithium tri-tert-butoxyaluminum hydride at −35 to −45° C. over 1 h.
03. Stir the reaction mixture for 2-3 h at −35 to −45° C.
04. Monitor the reaction by HPLC (30% EtOAc in DCM; NMT 3% of Stage-II Product).
05. Add 2N HCl solution (474 mL) to the reaction mixture, maintaining the temperature at <0° C.
06. Separate the layers and back extract the aqueous layer twice with dichloromethane (2×380 mL) 07. Wash the combined organic layers with water (380 mL) and then with brine solution (380 mL).
08. Completely remove the solvents by atmospheric distillation at less than 60° C.
09. Check the residue for water content. If it is >0.5%, add DCM (156 mL) and distill atmospherically again at less than 60° C.
10. Dissolve the residue in dry THF (380 mL), and keep the solution under a nitrogen atmosphere.
    this is the Stage IIIA Product.
11. Charge ethyltriphenylphosphonium bromide (295 g) and dry THF (250 mL) into a clean and dry flask under nitrogen.
12. Add a solution of potassium tert-butoxide (1M in THF, 769 mL) over 10 min and then stir the Resulting red-colored solution for 1 h at 25-35° C.

13. Add the THF solution from step 10 over ½ h and then stir for an additional 3 h at 25-35° C.
14. Check for completion by TLC (30% EtOAc in DCM; NMT 1% of Stage-IIIA Product).
15. Add ice water (780 mL) to the reaction mixture at 25-35° C. (exothermic by 5-8° C.).
16. Separate the layers and back extract the aqueous phase with MTBE (2×380 mL).
17. Combine the organic layers and wash with water (380 mL) and then brine (380 mL).
18. Distill out the solvents completely under vacuum and below 50° C.
19. Add MTBE (264 mL) and distill out completely under vacuum at below 50° C.
20. Add MTBE (380 mL) again and stir for 2 h at 25-35° C.
21. Filter the unwanted salts, wash them with MTBE (380 mL) and combine the filtrates.
22. Distill out the solvents completely under vacuum and below 50° C.
23. Add fresh MTBE (380 mL) and then distill it out completely under vacuum.
24. Add MTBE (380 mL) again and stir for 2 h at 25-35° C.
25. Filter the unwanted salts, wash them with MTBE (380 mL) and combine the filtrates distilled under vacuum up to 20%, add fresh MTBE (180 mL).
26. Charge filtrate (760 mL) Stage-IIIB Product into a clean and dry flask.
27. Charge DMAP (3.2 g).
28. Add triethylamine (73.8 mL).
29. Add acetic anhydride (37.58 mL) slowly at 25-35° C. over 15 min.
30. Stir the reaction mixture for 2-3 h at 25-35° C.
31. Check for completion by TLC (10% EtOAc in hexane; NMT 1% of Stage-IIIB Product).
32. Wash the reaction mixture with water (760 mL) and then aqueous layer extract with MTBE (380 mL) combined organic layer wash with saturated brine solution (380 mL).
33. Concentrate organic layer by completely atmospheric distillation below 50° C.
34. Charge methanol (152 mL) and completely remove the solvent under vacuum at below 50° C.
35. Charge 2% aqueous methanol (304 mL) and heat to 60-65° C.
36. Maintain the resulting clear solution for 1 h at 60-65° C., then slowly cool to 15-20° C. maintain for 2 h at same temp and then filter.
37. Wash the wet cake with chilled (10-15° C.) 2% aqueous methanol (76 mL).
38. Dry the resulting white solid in a hot air oven at 45-50° C. until the LOD is NMT 1%.

Wet weight: ~70 g.
Dry weight: 55 g
Yield: 63%
Moisture <0.5%
HPLC/RI Purity: 95.0%.

Stage-IV: Methyl 3α-acetoxy-5β-chol-9(11)-en-24-oate

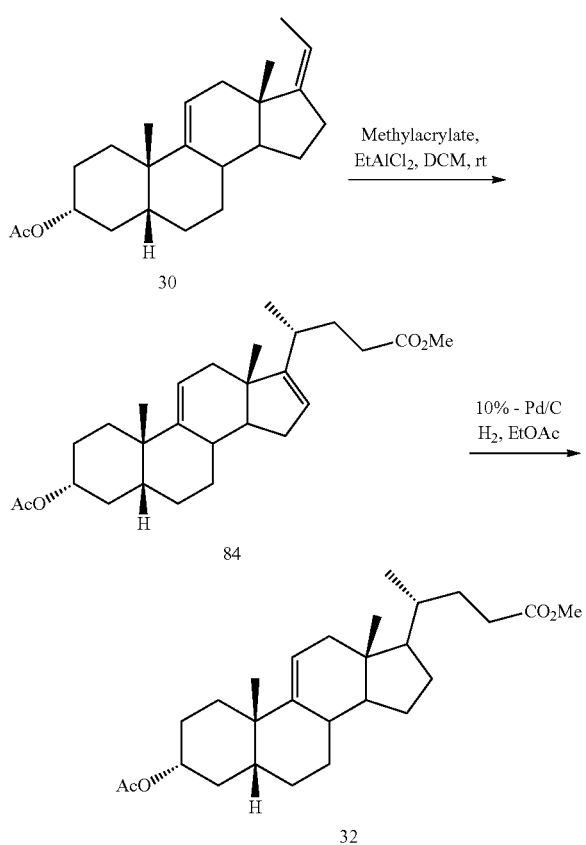

Raw Materials:

| S.No. | Raw Material | Qty | Unit | Mol. Wt. | Mole | Mole Ratio |
|---|---|---|---|---|---|---|
| 1 | Stage-III Product | 102 | g | 342 | 0.298 | 1.0 |
| 2 | Methyl acrylate | 61.0 | mL | 86 | 0.67 | 2.38 |
| 3 | Ethyl aluminum dichloride (1.8M in toluene) | 496 | mL | 126.98 | 0.893 | 3.0 |
| 4 | Dichloromethane | 1500 | mL | — | — | 15 V |
| 5 | Saturated bicarbonate sol | 1000 | mL | — | — | 10 V |
| 6 | Ethyl acetate | 1800 | mL | — | — | 18 V |
| 7 | Silica gel (# 60-120) | 300 | g | — | — | 3.0 |
| 8 | Hexane | 1000 | mL | — | — | 10.0 V |
| 9 | 10% Ethyl acetate in Hexane | 3000 | mL | — | — | 30 V |
| 10 | 10% Pd/carbon (50% water wet) | 12 | g | — | — | 12 wt % |
| 11 | Methanol | 600 | mL | — | — | 6.0 V |
| 12 | 3% Aqueous methanol | 400 | mL | — | — | 4.0 V |
| 13 | Water | 3000 | mL | — | — | 30 V |
| 14 | Saturated brine solution | 1000 | mL | — | — | 10.0 V |
| 15 | CELITE | 30 | g | — | — | — |

Experimental Procedure:

01. Charge dichloromethane (1000 mL) and stage-III product (102 g) cool the reaction mass to 0° C.
02. Add methyl acrylate (61 mL) over ½ h at 0-5° C.
03. Stir for 1 h at 0-5° C. and then add a solution of ethylaluminum dichloride (1.8 M, in toluene, 496 mL) over 1 h at 0-5° C. (Caution: This reagent reacts violently with water).
04. Stir for ½ h at 0-5° C. and raise the temperature to 25-35° C. and stir for 16 h.
05. Check for completion by TLC (10% EtOAc in hexane; NMT 5% of Stage-III Product).
06. Pour the reaction mass slowly in 10-15 min into ice water (2000 mL) and separate the phases.
07. Extract the aqueous layer with DCM (500 mL).
08. Combine the organic phases and wash with water (1000 mL) followed by saturated bicarbonate solution (1000 mL) and then brine solution (1000 mL).
09. Concentrate the organic phase to dryness under vacuum below 50° C. This is Stage IVA Product.
10. Residue dissolved in hexane (1000 mL) passed through silica bed buchnor funnel, bed wash with 10% ethyl acetate in hexane (3000 mL).
11. Collect total filtrate to dryness under vacuum below 50° C. This is Stage IVA Product.
12. After unloading the flask, rinse with 40% methanol in ethyl acetate (800 mL) and save this rinse for the next step.
13. Charge Stage IVA Product in 40% methanol in ethyl acetate rinse (200 mL) from above to a dry autoclave.
14. Charge slurry of 10% palladium on carbon (12 g in 200 mL of ethyl acetate).
15. Pressurize with hydrogen (70 psi) and stir the mixture for 16 h at 25-35° C.
16. Check for completion by HPLC (NMT 1% Stage IVA Product).
17. Filter the reaction mixture through CELITE® (30 g) and wash the cake with ethyl acetate (1000 mL).
18. Concentrate the filtrate to dryness via vacuum distillation below 60° C.
19. Add methanol (200 mL) and concentrate to dryness via vacuum distillation below 60° C.
20. Add 3% aqueous methanol (300 mL), stir for 15 min at 0-5° C., filter and wash the cake with 3% aqueous methanol (100 mL),
21. Dry the white solid in a hot air drier at 50-55° C. until the moisture content is NMT 0.5%.

Wet weight: ~80 g

Dry weight: 60 g

Yield: 85%

Moisture <0.5%

Melting range: 131.7-133.1° C.

SOR: +57.4 (c=1% in CHCl$_3$).

HPLC/RI Purity: 93.0%.

Stage-V: Methyl 3α-acetoxy-12-oxo-5β-chola-9(11)-en-24-oate

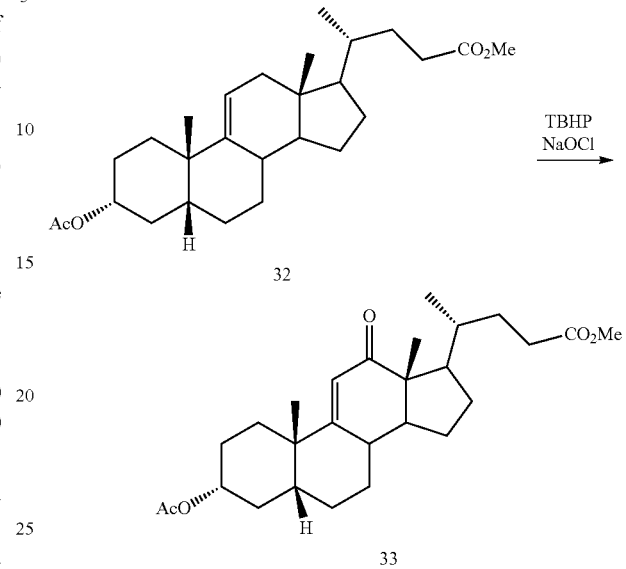

Raw Materials:

| S. No. | Raw Material | Qty | Unit | Mol. Wt. | Mole | Mole Ratio |
|---|---|---|---|---|---|---|
| 1 | Stage-IV Product | 60 | g | 430 | 0.139 | 1.0 |
| 2 | 70% TBHP in water | 610 | mL | 99.99 | 5.06 | 34.0 |
| 3 | 10% Sodium hypochlorite | 660 | mL | 74.5 | 1.036 | 7.0 |
| 4 | Pyridiniumchlorochromate | 32.8 | g | 215 | 0.1636 | 1.1 |
| 5 | Ethyl acetate | 900 | mL | — | — | 15 V |
| 6 | 20% aqueous methanol lot1 & 2 | 210 | mL | — | — | 3.5 V |
| 7 | 20% Sodium sulfite | 600 | mL | — | — | 10 V |
| 8 | Methanol lot1 | 240 | mL | — | — | 4.0 V |
| 9 | Water | 6000 | mL | — | — | 100 V |
| 10 | Saturated brine solution | 300 | mL | — | — | 5.0 V |
| 11 | Methanol lot2 | 383 | mL | — | — | 6.4 V |
| 12 | Water | 57 | mL | — | — | 0.95 V |
| 13 | 13% aqueous methanol | 40 | mL | — | — | 0.66 V |

Experimental Procedure:

01. Charge ethyl acetate (600 mL) and Stage-IV Product (60 g) into a clean and dry flask.
02. Stir for 10 min at 25-35° C.
03. Add 70% TBHP in water (610 mL) at 25-35° C., and then cool to at 0-5° C.
04. Add 10% sodium hypochlorite (660 mL) over 7 h at 0-5° C.
05. Stir the reaction mixture for 3 h at 0-5° C.
06. Check for completion by HPLC-RI (20% EtOAc in hexane; NMT 1% of Stage IV Product).
07. Separate the organic layer, aqueous layer extract with ethyl acetate (300 mL).
08. Combined organic layer wash with water (2×600 mL).
09. Charge ethyl acetate layer and 20% aqueous sodium sulfite (600 mL) maintain for 2 h at 55° C.
10. Separate the organic layer wash with water (2×600 mL).
11. Charge organic layer into R.B. flask charge PCC (32.8 g) at 25-30° C.
12. Stir the reaction mixture for 6-8 h at 25-30° C.
13. Check for completion by HPLC-RI (20% EtOAc in hexane; NMT 2% of Allylicalcohol).

14. Charge DM water (1200 mL) and stir for 15 min, separate organic layer.
15. Organic layer wash with DM water (3×600 mL), and brine solution (300 mL).
16. Completely remove the solvent under vacuum distillation below 50° C.
17. Add methanol (240 mL) and completely remove the solvent via vacuum distillation below 50° C.
18. Add 20% aqueous methanol (180 mL) and then cool to 0-5° C.
19. Stir for 2 h at 0-5° C., filter and wash the cake with chilled (0-5° C.) 20% aqueous methanol (30 mL).
20. Dry the solid in a hot air drier at 50-55° C. for 8 h, crude weight ~38 g.
21. Charge crude 38 g of stage-V material into a fresh and dry RBF 22. Charge methanol 383 mL.
23. Reflux the reaction mass to get the clear solution.
24. Add DM water drop wise 57 mL under reflux and continue the reflux for 30 min (observed solids precipitation).
25. Cool the reaction mass slowly to 20-25° C., then 10-15° C. and stir for 1 h.
26. Filter, suck dry & wash with 13% Aq methanol (40 mL).
27. Dry the compound under hot air oven at 60-65° C. until LOD: <0.5%.
   Wet weight: 38 g.
   Dry weight: 32 g.
   Yield: 51.6%.
   Melting range: 142-143.1° C.
   SOR: +102.4 (c=1% in Acetone).
   HPLC/RI Purity: 94.0%.
05. List of Raw Materials and Solvents The following list of raw materials and solvents are based on the details of the process described above.

| No. | Raw Materials |
|---|---|
| 01 | 9α-Hydroxyandrostenedione (Key starting material) |
| 02 | 10% Pd/C |
| 03 | Sulfuric acid |
| 04 | Lithium tri-tert-butoxyaluminum hydride |
| 05 | Potassium tert-butoxide |
| 06 | Ethyltriphenylphosphonium bromide |
| 07 | Acetic anhydride |
| 08 | Triethylamine |
| 09 | 4-(Dimethylamino)pyridine |
| 10 | Methyl acrylate |
| 11 | Ethylaluminum dichloride |
| 12 | 70% tert-Butylhydroperoxide |
| 13 | 10% Sodium hypochlorite |
| 14 | Sodium hydroxide |
| 15 | Pyridinium chlorochromate |

| No. | Solvents |
|---|---|
| 01 | Acetone |
| 02 | Dichloromethane |
| 03 | Methanol |
| 04 | Methyltertbutylether |
| 05 | Ethyl acetate |
| 06 | Tetrahydrofuran |
| 07 | Hexane |

06. Critical Parameters

During Process Modification, the following steps are identified as critical parameters, which may show significant affect on quality or yield.

Stage III

Operation:

Addition of lithium tri-tert-butoxyaluminum hydride solution under a nitrogen atmosphere to the compound at −40 to −45° C.

Explanation:

Control of the stoichiometry of the reducing agent, lithium tri-tert-butoxyaluminum hydride, is critical to a favorable outcome in this step. If too little reducing agent is used, the reaction will be incomplete. If too much is used, more of the by-product, compound 83, will be formed.

The control of the stoichiometry is made more challenging since the reducing agent is moisture sensitive. Therefore, it is important to use anhydrous solvents and for the reaction to be carried out under a nitrogen atmosphere. If moisture is allowed to contaminate the reaction, some of the lithium tri-tert-butoxyaluminum hydride will be quenched.

Operation:

Addition of potassium tert-butoxide solution under nitrogen atmosphere to the compound at 25 to 35° C.

Explanation:

A strong base is required for this reaction. Potassium tert-butoxide is a sufficiently strong base and works well. If it is exposed to water, the base is quenched and instead forms potassium hydroxide, which is not a strong enough base to cause the desired reaction. For this reason, it is important to use anhydrous solvents and to carry this reaction out under a nitrogen atmosphere.

Stage IV

Operation:

Addition of Ethylaluminum dichloride solution under nitrogen atmosphere at 0 to 5° C.

Explanation:

Ethylaluminum dichloride is a uniquely good catalyst for this reaction. Other, less expensive catalysts have been tried, but the reaction does not work well with these. Water will react with ethylaluminum dichloride and destroy its ability to catalyze this reaction. For this reason, it is important to use anhydrous solvents and a nitrogen atmosphere for this reaction. If the reaction is exposed to even small amounts of water, it does not work.

Stage V

Operation:

Addition of Sodium hypochlorite should be required 6-7 h, the temperature must be controlled to below 5° C.

Justification:

Temperatures above 5° C. give poorer results in this reaction, and it is possible for the temperature to climb above this limit during the addition of sodium hypochlorite.

Therefore, it is important to add the sodium hypochlorite at a rate that is slow enough that it still allows for good temperature and time control. This may prove to be an even bigger problem on large scale.

07. Cleaning Procedure

Study has been carried out on deoxycholic acid intermediates for establishing cleaning procedure. It is concluded that, deoxycholic acid intermediates are freely soluble in dichloromethane followed by water & methanol.

08. Impurities in DCA—Intermediates:

During the course of process development, a number of impurities were isolated and identified, or in some cases suspected impurities were synthesized independently. A list of such compounds along with the data that is available for each compound is given in the table below.

| Stage Number | Impurity Common Name | Impurity structure | Data available |
|---|---|---|---|
| I | 5 α-compound-26 | 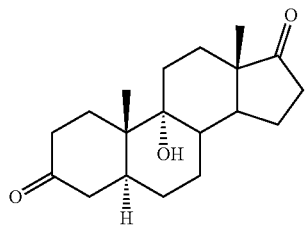 | 1H NMR, Mass, HPLC-RI, MR, SOR |
| II | 5 α-compound-27 | 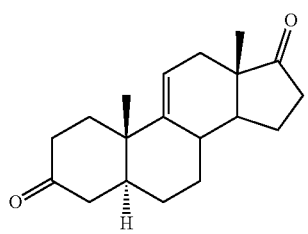 [SMILES: C[C@]12CC=C3C(CC[C@H]4CC(=O)CC[C@]34C)C1CCC2=O] | 1H NMR, Mass, HPLC-RI |
| III | compound-83 | 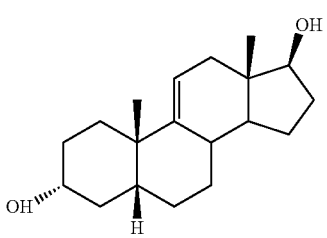 [SMILES: C[C@]12CC=C3C(CC[C@@H]4C[C@H](O)CC[C@]34C)C1CC[C@@H]2O] | 1H NMR, Mass, HPLC-RI, |
| III | Di-Wittig compound | 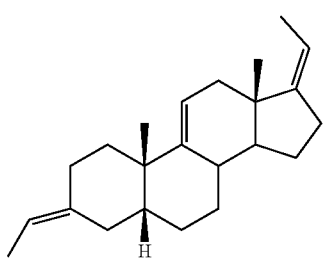 [SMILES: C/C=C1/CC[C@]2(C)C3=CC[C@]4(C)/C(=C\C)CCC4C3CC[C@@H]2C1] | 1H NMR, Mass, HPLC-RI |
| III | Di Acetyl compound | 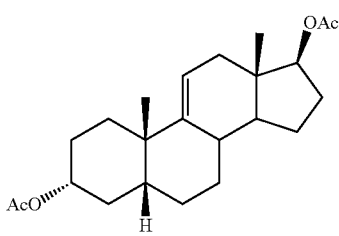 [SMILES: CC(=O)O[C@@H]1CC[C@]2(C)C3=CC[C@@]4(C)C(CC[C@@H]4OC(C)=O)C3CC[C@@H]2C1] | 1H NMR, HPLC-RI |
| IV | 8,9-Ene 17-ethyl compound | 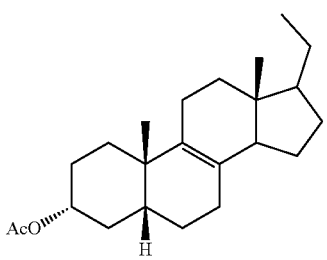 [SMILES: CCC1CCC2C3=C(CC[C@]12C)[C@@]1(C)CC[C@@H](OC(C)=O)C[C@H]1CC3] | 1H NMR, Mass, HPLC-RI |

| Stage Number | Impurity Common Name | Impurity structure | Data available |
|---|---|---|---|
| IV | 8,9-Ene | | 1H NMR, Mass, HPLC-RI |
| V | Allylicalcohol | | 1H NMR, Mass, HPLC-RI |
| V | 12-tert-butylperoxycompound | | 1H NMR, Mass, HPLC-RI |

Example 12

A manufacturing process for the synthesis of deoxycholic acid from compound 24 as shown in Scheme 2 has been made suitable for large scale production. The manufacturing process is safe, economical, environmentally-friendly and produces high quality final product that consistently meets specifications.

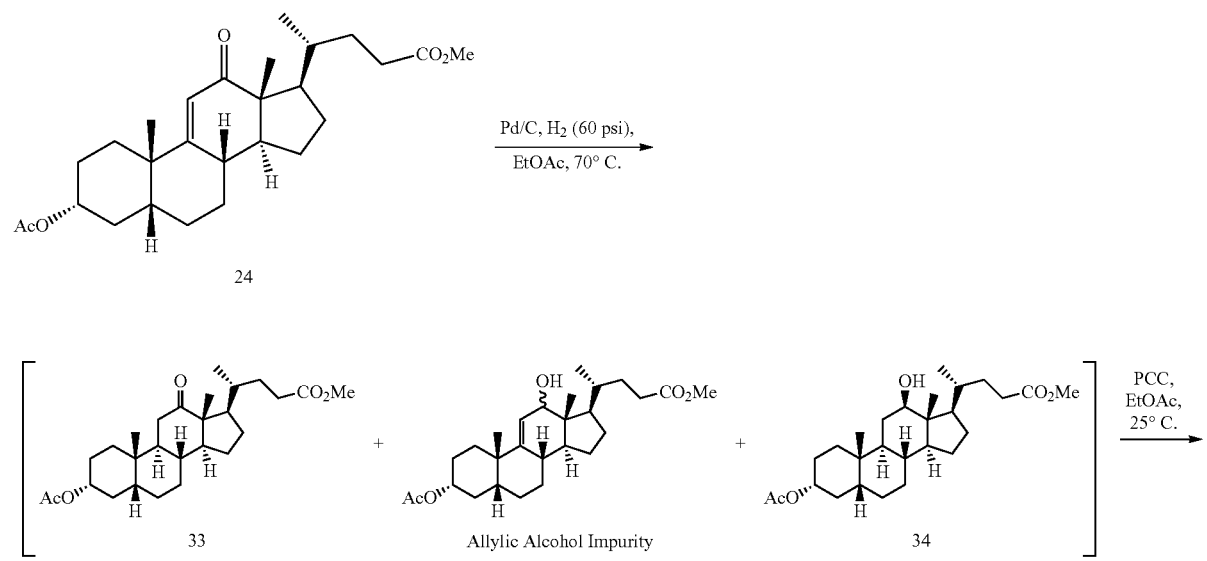

-continued

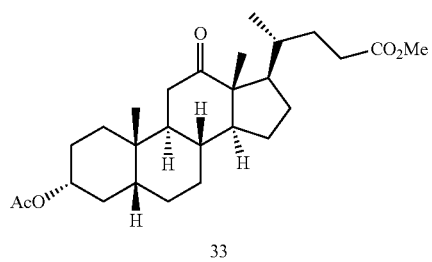

33

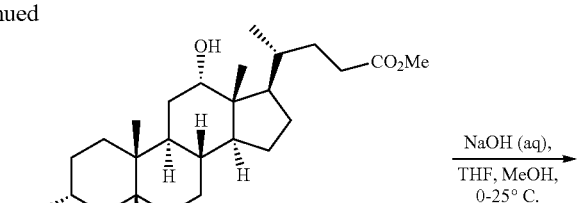

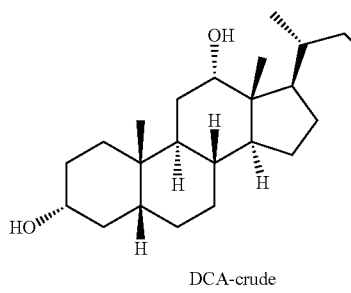

DCA-crude

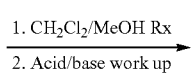

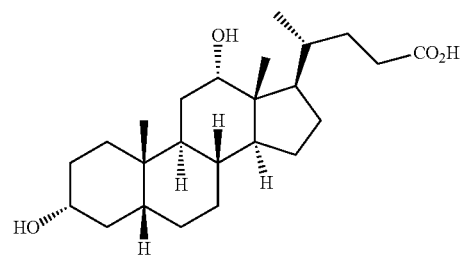

DCA

Preparation of Compound 33

The formation of compound 33 was conducted on 40 gram scale. To 10.0 g (25 wt %) of dry 10% palladium on carbon (Pd/C) was added compound 24 (40.0 g, 90.0 mmol, 98.2% AUC by HPLC) followed by 600 mL of ethyl acetate (EtOAc). The reaction mixture was pressurized to 60 psi of hydrogen ($H_2$) and allowed to react at 70° C. HPLC analysis after 13 hours indicated <1% AUC by HPLC of compound 24 remained, <1% AUC of the allylic alcohol had formed and 14.5% AUC of the diastereomer of compound 24 34 had formed. The reaction was deemed complete, cooled to 30-35° C. and filtered over CELITE® The CELITE® cake was washed with EtOAc (400 mL) and the resulting filtrate was concentrated to ~25 volumes and taken forward without further manipulation.

The PCC oxidation was conducted using the sample of compound 33 in EtOAc (25 vol) from above. To a sample of compound 33 (90.0 mmol) in EtOAc (25 vol) was added PCC (19.4 g, 1.0 equiv, Aldrich lot #S37874-058). The reaction mixture was maintained at 20-25° C. for 25 hours. HPLC analysis indicated 1.1% AUC of the diastereomer of compound 34. The reaction mixture was deemed complete, diluted with DI water (400 mL) and filtered over CELITE®. The filter cake was washed with EtOAc (2×200 mL). The resulting filtrate was washed with DI water (2×400 mL) and treated with DARCO® KB-G (8.0 g). The mixture was heated to 45-50° C. for 4 hours and then cooled to 20-25° C. The slurry was filtered over CELITE® and the filter cake was washed with EtOAc (2×200 mL). The EtOAc filtrate was concentrated to ~5 volumes and azeotroped with MeOH (2×600 mL) back down to ~5 volumes. The resulting slurry was assayed by $^1$H NMR to indicate 6.4 mol % of EtOAc remained. The slurry was diluted with DI water (320 mL) and maintained at 20-25° C. for 1 hour. The slurry was filtered, washed with DI water (2×200 mL) and dried under vacuum at 35-45° C. to afford 27.4 g (68%) of compound 33 (97.9% AUC by HPLC containing 0.8% AUC of the diastereomer of compound 34). KF analysis indicated 0.02 wt % water. The lower than expected yield was most likely attributed to the elevated level of EtOAc present during the precipitation Preparation of Compound 34

A 10 gram portion of the above sample of compound 33 was taken forward to the formation of compound 34 implementing the following isolation conditions. To a solution of compound 33 (10.0 g, 22.4 mmol) in 60 mL of tetrahydrofuran (THF) at 4-6° C. was added 33.6 mL (1.5 equiv, Aldrich lot #00419TH) of 1 M lithium tri-tert-butoxyaluminum hydride (Li(t-BuO)$_3$AlH) in THF maintaining the temperature below 6° C. HPLC analysis after 18 hours indicated <1% AUC of compound 33 remained and 5.5% AUC of the diastereomer of compound 34 had formed. The reaction was deemed complete and quenched with 4 M HCl (150 mL) maintaining the temperature below 20° C. The reaction mixture was extracted with heptane (2×100 mL). The combined organic phases were washed with 1 M HCl (100 mL) and DI water (2×100 mL). The clear solution was distilled down to ~10 volumes and azeotroped with heptane (2×100 mL) down to ~10 volumes. Some scaling was observed and the sample was diluted with heptane (100 mL) and MTBE (2.5 mL). The sample was then heated to dissolution at 70-75° C. and allowed to cool step-wise down to −52° C. over a period of 1 hour when solids precipitated. The thin slurry was held at 52° C. for 1 hour, 48° C. for 1 hour and 42° C. for 1 hour before the heat was turned off and the slurry was allowed to slowly cool to 20-25° C. overnight. The slurry was filtered, washed with heptane (2×25 mL) and dried under vacuum at 35-45° C. to afford 6.8 g (68%) of compound 34 (96.0% AUC containing 2.8% AUC of the diastereomer of compound 34) as white solids. Some scaling was observed in the flask after the filtration. The solids were dissolved in $CH_2Cl_2$ and concentrated to afford 1.3 g (13%) of compound 34 (96.5% AUC containing 1.9% AUC of the diastereomer of compound 34). The mother liquor and washes were concentrated to afford 1.6 g (16%) of compound 34.

Due to the lower than expected yield from the precipitation, the procedure was repeated using 100% heptane instead of 1.25% MTBE/heptane. A sample of compound 34 (10 g, 22.4 mmol, 93.4% AUC by HPLC) was diluted with heptane (200 mL) and heated to dissolution at 80-85° C. The solution was allowed to slowly cool down to −65° C. over a period of 1 hour when solids precipitated. The thin slurry was held at 65° C. for 1 hour and cooled in 5° C. increments down to 30° C. over a period of 2 hours. The slurry was filtered at 30° C., washed with heptane (2×25 mL) and dried under vacuum at 35-45° C. to afford 7.5 g (75% recovery) of compound 34 (95.7% AUC containing 0.1% AUC of the diastereomer of compound 34) as white solids. Some scaling was observed in the flask after the filtration. HPLC analysis are in progress for the reactor rinse and mother liquor Preparation of DCA-Crude A sample of aqueous DCA-crude (340 mL) was washed with 2-MeTHF (2×340 mL). The aqueous phase was assayed by HPLC to indicate 0.1% AUC of the unknown impurity with RRT=1.12. The aqueous phase was diluted with 2-MeTHF (340 mL) and adjusted to pH=1.7-2.0 using 4 M HCl (60 mL). The phases were separated and the 2-MeTHF phase was washed with DI water (2×400 mL). The 2-MeTHF phase was concentrated to ~5 volumes and azeotroped back down to ~5 volumes with heptane (3×320 mL). The 5 volume slurry was assayed by $^1$H NMR to indicate 2.0 mol % of 2-MeTHF remained relative to heptane. The slurry was diluted with heptane (320 mL) and held at 20-25° C. for 1 hour. The slurry was filtered, washed with heptane (2×150 mL) and dried under vacuum at 35-45° C. to afford 24.2 g (96%) of DCA-crude (95.7% AUC containing 0.4% AUC of the diastereomer of DCA-crude, 1.8% AUC of the unknown impurity with RRT=0.5 and 0.04% AUC of the unknown impurity with RRT=1.12,)

Preparation of DCA

A series of slurry purifications of DCA-crude were attempted on 2.0 g to assess the purity and recovery. Samples of DCA-crude (2.0 g, 5.1 mmol) were diluted with 25 volumes of MeOH/CH$_2$Cl$_2$ (See Table 1) and the resulting slurries were held at specific temperatures (See Table 1) for 1 hour. The slurries were allowed cool to specific temperatures (See Table 1) and filtered. The filter cakes were washed with CH$_2$Cl$_2$ (2×3 vol) and dried under vacuum at 35-40° C. overnight to afford DCA (See Table 1). The results are summarized in Table 1 below

TABLE 1

Results for DCA

| Entry | mol % MeOH relative to CH$_2$Cl$_2$ | Slurry temp (° C.) | Filtration temp (° C.) | Amt, recovery | DCA Results HPLC results % AUC) DCA | Diast. of DCA | Impurities (RRT) 0.5 | 1.12 |
|---|---|---|---|---|---|---|---|---|
| 1 | 2 | 35-37 | 28-30 | 1.3 g, 65% | 99.00 | ND | 0.87 | ND |
| 2 | 1 | 35-37 | 28-30 | 1.7 g, 85% | 98.95 | ND | 0.92 | ND |
| 3 | 1 | 20-25 | 20-25 | 1.7 g, 85% | 99.15 | ND | 0.74 | ND |
| 4 | 0.5 | 20-25 | 20-25 | 1.8 g, 90% | 98.92 | ND | 0.86 | ND |
| 5 | 0 | 20-25 | 20-25 | 1.7 g, 85% | 99.02 | ND | 0.70 | ND |

The results from entries 1-3 indicated that conducting the slurry purification at 20-25° C. with 1 mol % of MeOH provided better recovery and comparable results to conducting the slurry at 35-37° C. with 2 mol % of MeOH. The samples of DCA were analyzed by $^1$H NMR to indicate <1 wt % of CH$_2$Cl$_2$ was present after drying.

What is claimed is:

1. A process for preparing a 12-keto compound 3:

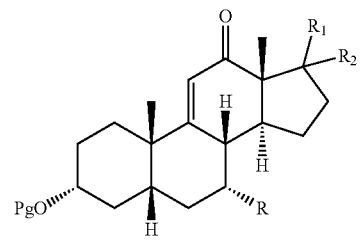

the process comprising:

contacting Δ-9,11-ene compound 4:

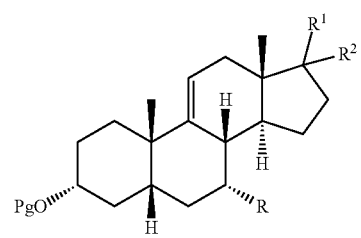

with an alkylhydroperoxide of the formula $(R^3)(R^4)(R^5)C$—O—OH in the presence of a co-oxidant to prepare a compound of formula 1:

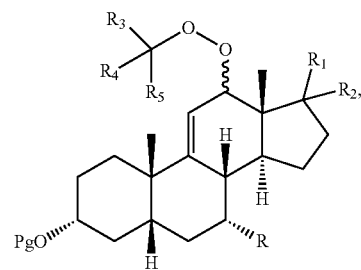

wherein:

Pg is a hydroxyl protecting group;

R is hydrogen, hydroxyl, or —OPg;

$R^1$ is the 17-side chain of a bile acid selected from the group consisting of cholic acid, deoxycholic acid, taurocholic acid, and glycocholic acid, wherein the carboxyl functionality of said side chain is optionally esterified with a $C_1$-$C_6$ alkyl group, and $R^2$ is hydrogen, or $R^1$ and $R^2$ together with the carbon atom attached thereto form a keto or a keto protecting group; and each of $R^3$, $R^4$, and $R^5$ is independently $C_1$-$C_3$ alkyl;

converting the compound of formula 1 to compound 2:

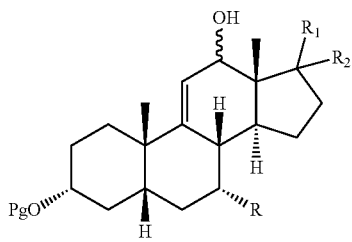

under reducing conditions; and contacting compound 2 with an oxidizing agent to prepare the 12-keto compound 3.

2. The process of claim 1, wherein compound 4 is contacted with more than one equivalent of tert-butyl hydroperoxide and in the presence of CuI.

3. The process of claim 1, wherein the co-oxidant is selected from the group consisting of aqueous sodium hypochlorite, palladium on carbon, $Pd(OCOCF_3)_2$, $Pd(OAc)_2$ and CuI.

4. The process of claim 1, wherein the compound of formula 1 is selected from the group consisting of compounds 42, 43, 44, 45 and 46:

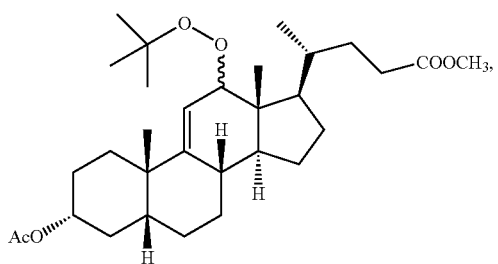

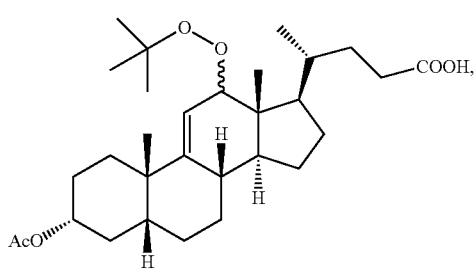

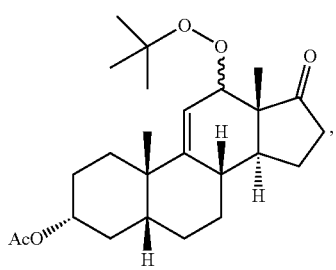

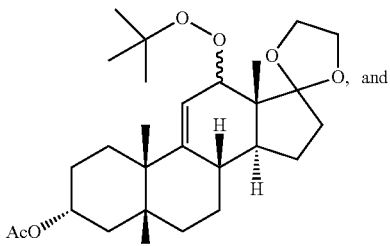

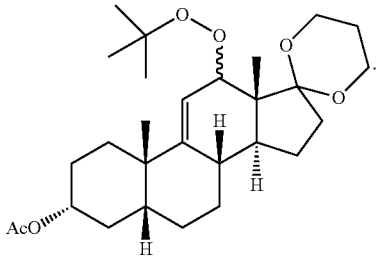

5. The process of claim 1, wherein $R^1$ is selected from the group consisting of

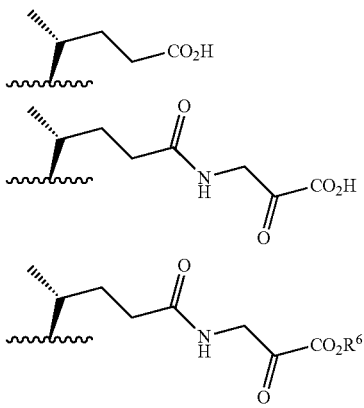

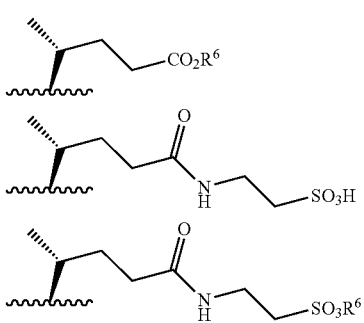

wherein $R^6$ is lower alkyl and ⁓ represents the point of connection to the 17-position of steroidal scaffold.

6. The process of claim 1, wherein $R^1$ and $R^2$ together with the carbon atom attached thereto form a keto group.

7. The process of claim 1, wherein $R^1$ and $R^2$ together with the carbon atom attached thereto form:

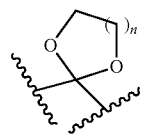
wherein n is 1, 2, or 3 and the wavy line ∿ represents the point of connection to the rest of the molecule.
8. The process of claim 1, wherein R is hydrogen.
9. The process of claim 1, wherein the reducing conditions comprise contact with aqueous sodium sulfite.
10. The process of claim 1, wherein the oxidizing agent is pyridinium chlorochromate.
\* \* \* \* \*